United States Patent
Semba et al.

(10) Patent No.: US 12,036,204 B2
(45) Date of Patent: *Jul. 16, 2024

(54) PHARMACEUTICAL COMPOSITION FOR TREATING TUMOR

(71) Applicants: Eisai R&D Management Co., Ltd., Tokyo (JP); Ono Pharmaceutical Co., Ltd., Osaka (JP)

(72) Inventors: Taro Semba, Tsukuba (JP); Yasuhiro Funahashi, Tokyo (JP); Takuya Suzuki, Tokyo (JP)

(73) Assignees: EISAI R&D MANAGEMENT CO., LTD., Tokyo (JP); ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/563,162

(22) Filed: Dec. 28, 2021

(65) Prior Publication Data

US 2022/0117933 A1 Apr. 21, 2022

Related U.S. Application Data

(63) Continuation-in-part of application No. PCT/JP2020/028663, filed on Jul. 27, 2020, which is a continuation-in-part of application No. 16/835,719, filed on Mar. 31, 2020, now Pat. No. 11,083,705.

(30) Foreign Application Priority Data

Jul. 26, 2019 (JP) ................. 2019-138041

(51) Int. Cl.
*A61K 31/357* (2006.01)
*A61K 39/395* (2006.01)
*A61P 35/00* (2006.01)

(52) U.S. Cl.
CPC ........ *A61K 31/357* (2013.01); *A61K 39/3955* (2013.01); *A61P 35/00* (2018.01)

(58) Field of Classification Search
CPC .... A61K 31/357; A61K 39/3955; A61P 35/00
USPC .................................................... 424/133.1
See application file for complete search history.

(56) References Cited

U.S. PATENT DOCUMENTS

| | | | |
|---|---|---|---|
| 5,192,549 A | 3/1993 | Barenolz et al. | |
| 5,316,771 A | 5/1994 | Barenholz et al. | |
| 5,571,534 A | 11/1996 | Jalonen et al. | |
| 5,736,155 A | 4/1998 | Bally et al. | |
| 5,759,573 A | 6/1998 | Kim | |
| 5,821,349 A | 10/1998 | Djedaini-Pilard et al. | |
| 6,051,251 A | 4/2000 | Zalipsky et al. | |
| 6,214,865 B1 | 4/2001 | Littlefield et al. | |
| 6,469,182 B1 | 10/2002 | Littlefield et al. | |
| 6,653,341 B1 | 11/2003 | Littlefield et al. | |
| 6,747,011 B1 | 6/2004 | Zhang | |
| 7,488,802 B2 | 2/2009 | Collins et al. | |
| 7,521,051 B2 | 4/2009 | Collins et al. | |
| 7,982,060 B2 | 7/2011 | Austad et al. | |
| 8,008,449 B2 | 8/2011 | Korman et al. | |
| 8,093,410 B2 | 1/2012 | Chase et al. | |
| 8,168,757 B2 | 5/2012 | Finnefrock et al. | |
| 8,350,067 B2 | 1/2013 | Endo et al. | |
| 8,354,509 B2 | 1/2013 | Carven et al. | |
| 8,383,796 B2 | 2/2013 | Korman et al. | |
| 9,968,583 B2 | 5/2018 | Kikuchi et al. | |
| 10,945,990 B2 | 3/2021 | Matsui et al. | |
| 11,071,713 B2 | 7/2021 | Kikuchi et al. | |
| 11,083,705 B2 | 8/2021 | Semba et al. | |
| 2002/0131995 A1 | 9/2002 | Szoka | |
| 2004/0156889 A1 | 8/2004 | Hu et al. | |
| 2005/0118249 A1 | 6/2005 | Webb et al. | |
| 2005/0118250 A1 | 6/2005 | Tardi et al. | |
| 2006/0008909 A1 | 1/2006 | Cullis et al. | |
| 2006/0104984 A1 | 5/2006 | Littlefield et al. | |
| 2006/0147511 A1 | 7/2006 | Panzer et al. | |
| 2007/0112176 A1 | 5/2007 | Seiki et al. | |
| 2007/0116753 A1 | 5/2007 | Hong et al. | |
| 2007/0155696 A1 | 7/2007 | Ishihara et al. | |
| 2007/0244187 A1 | 10/2007 | Austad et al. | |
| 2009/0196913 A1 | 8/2009 | Huang et al. | |
| 2009/0196918 A1 | 8/2009 | Joguparthi et al. | |
| 2010/0247629 A1 | 9/2010 | Gabizon et al. | |
| 2011/0018419 A1 | 1/2011 | Suzuki et al. | |
| 2011/0184190 A1 | 7/2011 | Endo et al. | |
| 2011/0262524 A1 | 10/2011 | Bally et al. | |
| 2011/0271358 A1 | 11/2011 | Freeman et al. | |
| 2012/0058178 A1 | 3/2012 | Kikuchi et al. | |
| 2012/0128757 A1 | 5/2012 | Kikuchi et al. | |

(Continued)

FOREIGN PATENT DOCUMENTS

| CA | 2673924 A | 7/2008 |
|---|---|---|
| CA | 2673924 A1 | 7/2008 |

(Continued)

OTHER PUBLICATIONS

Topalian et al. (N Engl J Med. Jun. 28, 2012, 366(26):2443-54).*
BMS-936558_ Nivolumab-NCBI-MeSH (2010, pp. 1-2).*
Excerpted file history of U.S. Appl. No. 13/260,864: Issue fee payment (dated Apr. 9, 2018); Supplemental Notice of Allowability (dated Jan. 24, 2018); Corrected Filing Receipt (dated Jan. 17, 2018); Notice of Allowance and Issue Fee Due (dated Jan. 8, 2018). Final and Non Final Office actions in United States Patent Application No. 13/260,864, dated Nov. 10, 2015 and Oct. 14, 2015 respectively, 20 pages.
Final Office Action in U.S. Appl. No. 14/061,426, dated Mar. 26, 2021, 19 pages.

(Continued)

*Primary Examiner* — Yan Xiao
(74) *Attorney, Agent, or Firm* — Morgan, Lewis & Bockius LLP

(57) ABSTRACT

A combined administration of a liposomal composition comprising Eribulin or a pharmaceutically acceptable salt thereof and a PD-1 antagonist exhibits unexpected antitumor effect.

18 Claims, 6 Drawing Sheets

(56) References Cited

U.S. PATENT DOCUMENTS

| | | |
|---|---|---|
| 2014/0044777 A1 | 2/2014 | Kikuchi et al. |
| 2014/0212479 A1 | 7/2014 | Zeinelden |
| 2014/0248263 A1 | 9/2014 | Andersen et al. |
| 2015/0005343 A1 | 1/2015 | Nomoto et al. |
| 2015/0210769 A1 | 7/2015 | Freeman et al. |
| 2015/0246033 A1 | 9/2015 | Flynn et al. |
| 2016/0296633 A1 | 10/2016 | Goldenberg et al. |
| 2016/0338954 A1 | 11/2016 | Brinker et al. |
| 2017/0020817 A1 | 1/2017 | Singh |
| 2017/0071903 A1 | 3/2017 | Funahashi et al. |
| 2018/0071247 A1 | 3/2018 | Matsui et al. |
| 2019/0010232 A1 | 1/2019 | Kalos et al. |
| 2019/0111022 A1 | 4/2019 | Asano et al. |
| 2019/0263927 A1 | 8/2019 | Olivo |
| 2021/0023047 A1 | 1/2021 | Semba et al. |
| 2021/0177802 A1 | 6/2021 | Semba et al. |
| 2022/0389110 A1 | 12/2022 | Jure-Kunkel et al. |

FOREIGN PATENT DOCUMENTS

| | | |
|---|---|---|
| CN | 101209243 A | 7/2008 |
| CN | 103562406 A | 2/2014 |
| CN | 105640935 A | 6/2016 |
| CN | 107207580 A | 9/2017 |
| EP | 1332755 A1 | 8/2003 |
| EP | 1921086 A1 | 5/2008 |
| EP | 2123260 A1 | 11/2009 |
| EP | 2415464 A1 | 2/2012 |
| JP | H07-501813 A | 2/1995 |
| JP | H08-509230 A | 10/1996 |
| JP | 2002-518384 A | 6/2002 |
| JP | 2004-516247 A | 6/2004 |
| JP | 2005-509000 A | 4/2005 |
| JP | 2006-513189 A | 4/2006 |
| JP | 2006-340714 A | 12/2006 |
| JP | 2010-514708 A | 5/2010 |
| JP | 5551683 B2 | 5/2014 |
| JP | 5551683 B2 | 7/2014 |
| JP | 2018-508516 A | 3/2018 |
| RU | 2405601 C1 | 10/2010 |
| RU | 2476216 C1 | 2/2013 |
| WO | 93/11757 A1 | 6/1993 |
| WO | 94/23697 A1 | 10/1994 |
| WO | 93/11757 A1 | 6/1996 |
| WO | 99/65894 A1 | 12/1999 |
| WO | 02/32399 A1 | 4/2002 |
| WO | 03/041681 A2 | 5/2003 |
| WO | 2004/004771 A1 | 1/2004 |
| WO | 2004/056875 A1 | 7/2004 |
| WO | 2004/058140 A2 | 7/2004 |
| WO | 2004/072286 A1 | 8/2004 |
| WO | 2005/046643 A2 | 5/2005 |
| WO | 2005/118565 A1 | 12/2005 |
| WO | 2006/037230 A1 | 4/2006 |
| WO | 2007/026869 A1 | 3/2007 |
| WO | 2007/061874 A2 | 5/2007 |
| WO | 2008/080367 A1 | 7/2008 |
| WO | 2008/156712 A1 | 12/2008 |
| WO | 2010/027827 A2 | 3/2010 |
| WO | 2010/077634 A1 | 7/2010 |
| WO | 2010/113983 A1 | 10/2010 |
| WO | 2010/113984 A1 | 10/2010 |
| WO | 2011/066342 A1 | 6/2011 |
| WO | 2011/066342 A2 | 6/2011 |
| WO | 2011/094339 A1 | 8/2011 |
| WO | 2012/1190777 A1 | 9/2012 |
| WO | 2012/135408 A1 | 10/2012 |
| WO | 2013/019906 A1 | 2/2013 |
| WO | 2013/019906 A9 | 2/2013 |
| WO | 2014/087230 A1 | 6/2014 |
| WO | 2014/159562 A1 | 10/2014 |
| WO | 2014/193898 A1 | 12/2014 |
| WO | 2014/199294 A1 | 12/2014 |
| WO | 2014/208774 A1 | 12/2014 |
| WO | 2015/063302 A2 | 5/2015 |
| WO | 2015/112900 A1 | 7/2015 |
| WO | 2015/134399 A1 | 9/2015 |
| WO | 2015/134605 A1 | 9/2015 |
| WO | 2015/183961 A1 | 12/2015 |
| WO | 2015/184145 A1 | 12/2015 |
| WO | 2015/184145 A8 | 12/2015 |
| WO | 2016/130839 A1 | 8/2016 |
| WO | 2016/141209 A1 | 9/2016 |
| WO | 2017/188350 A1 | 11/2017 |
| WO | 2018/071792 A1 | 4/2018 |

OTHER PUBLICATIONS

Final Office Action in U.S. Appl. No. 16/090,360, dated Apr. 2, 2021, 7 pages.

Final Rejection in Algerian Patent Application No. 110640, dated Aug. 18, 2013, 2 pages.

FormuMax Scientific Inc., "Doxoves-Liposome Doxorubicin Compared to Doxil," Doxoves-Liposomal Doxorubicin, 1995, 1-4, XP002684032, [Retrieved on Sep. 24, 2012], retrieved from: URL <www.liposomeexpert.com/categories/Drug-Loaded-Liposomes>.

Furnishing of Prescribed Information and Voluntary Amendment and Payment of Fee for Grant in Singaporean Patent Application No. 201106388-0, dated Mar. 26, 2014, 17 pages.

Gao et al., "Overexpression of PD-L1 Significantly Associates with Tumor Aggressiveness and Postoperative Recurrence in Human Hepatocellular Carcinoma," Clin. Cancer Res., 2009, 15(3):971-979.

Ghebeh et al. "FOXP3$^+$ Tregs and B7-HI$^+$ /PD-1$^+$ T lymphocytes co-infiltrate the tumor tissues of high-risk breast cancer patients: Implication for immunotherapy," BMC Cancer, 2008, 8:57.

Ghebeh et al., "The B7-H1 (PD-L1) T Lymphocyte-Inhibitory Molecule is Expressed in Breast Cancer Patients with Infiltrating Ductal Carcinoma: Correlation with Important High-Risk Prognostic Factors," Neoplasia, 2006, 8(3):190-198.

Hagiwara et al., "Preparation and pharmaceutical evaluation of liposomes entrapping salicylic acid/γ-cyclodextrin conjugate," Chem. Pharm. Bull., 2006, 54(1):26-32.

Hamanishi et al., "Programmed cell death 1 ligand 1 and tumor-infiltrating CD8$^+$ T lymphocytes are prognostic factors of human ovarian cancer," PNAS, 2007, 104(9):3360-3365.

Hearing Notice in Indian Patent Application No. 6850/DELNP/2011, dated Aug. 17, 2017, 3 pages.

Hino et al., "Tumor Cell Expression of Programmed Cell Death-1 Ligand 1 is a Prognostic Factor for Malignant Melanoma," Cancer, 2010, 116(7):1757-1766.

Inman et al., "PD-L1 (B7-H1) Expression by Urothelial Carcinoma of the Bladder and BCG-Induced Granulomata," Cancer, 2007, 109(8):1499-1505.

Intimation Notification in Indian Patent Application No. 6850/DELNP/2011, dated Aug. 23, 2018, 1 page.

IUPAC Goldbook, "Onium Compunds," Entry, [Retrieved on Mar. 9, 2016], retrieved from: URL<http://goldbook.iupac.org/O04291.html>, 2 pages.

Jordan et al., "The primary antimitotic mechanism of action of the synthetic halichondrin E/389 is suppression of microtubule growth," Molecular Cancer Therapeutics, 2005, 4(7):1086-1095.

Kazmi et al., "Real-world 1-year survival analysis of patients with metastatic breast cancer with liver or lung visceral metastasis treated with eribulin, gemcitabine," Poster Display, Abstract No. 366P, displayed Sep. 29, 2019, European Society for Medical Oncology (ESMO) 2019 Congress, Barcelona, Spain, 1 page.

Lasic et al., "Gelation of liposome interior; A novel method for drug encapsulation," FEBS Letters, 1992, 312(2-3):255-258.

Letters Patent for Patent No. 10271 in Algerian Patent Application No. 110640, dated Sep. 13, 2020, 4 pages.

Letters Patent for the Brazilian Patent No. PI 1014527-3, granted on Nov. 24, 2020, 70 pages.

Patent Certificate for European Patent No. 2415464, granted on May 10, 2017, 1 page.

Patent Certificate for European Patent No. 2415470, granted on Jul. 6, 2016, 1 page.

(56) References Cited

OTHER PUBLICATIONS

Patent Certificate for Hong Kong Patent No. HK1165707, granted on Jul. 7, 2017, 2 pages.
Patent Certificate for Indian Patent No. 300213, dated Aug. 23, 2018, 1 page.
Patent Certificate for Indonesian Patent No. IDP000045351, granted on Apr. 20, 2017, 66 pages.
Patent Certificate for Israeli Patent No. 215059, granted on Jul. 1, 2016, 4 pages.
Patent Certificate for Japanese Patent No. 5551683, granted on May 30, 2014, 4 pages.
Patent Certificate for Japanese Patent No. 5622719, granted on Oct. 3, 2014, 4 pages.
Patent Certificate for Japanese Patent No. 5770336, granted on Jul. 3, 2015, 4 pages.
Patent Certificate for Korean Patent No. 10-1495951, granted on Feb. 16, 2015, 4 pages.
Patent Certificate for Malaysian Patent No. MY-160203-A, granted on Feb. 28, 2017, 4 pages.
Patent Certificate for Mexican Patent No. 326330, granted on Dec. 15, 2014, 2 pages.
Patent Certificate for Moroccan Patent No. 33127, granted on Mar. 1, 2012, 3 pages.
Patent Certificate for New Zealand Patent No. 595212, granted on Jun. 4, 2014, 1 page.
Patent Certificate for Philippine Patent No. 1-2011-501838, granted on Nov. 25, 2015, 69 pages.
Patent Certificate for Russian Patent No. 2476216, granted on Feb. 27, 2013, 44 pages.
Patent Certificate for Singaporean Patent No. 174255, granted on Apr. 15, 2014, 2 pages.
Patent Certificate for South African Patent No. 2011-06535, granted on May 30, 2012, 3 pages.
Patent Certificate for Sri Lankan Patent No. 16427, granted on Aug. 6, 2014, 3 pages.
Patent Certificate for Taiwanese Patent No. I392519, granted on Apr. 11, 2013, 3 pages.
Patent Certificate for Ukrainian Patent No. 103794, granted on Nov. 25, 2013, 32 pages.
Patent Certificate for U.S. Pat. No. 9,968,583, granted on May 15, 2018, 34 pages.
Patent Certificate for Vietnamese Patent No. 17167, granted on Jul. 4, 2017, 58 pages.
PCT International Search Report in International Patent Application No. PCT/JP2020/028663, dated Sep. 24, 2020, 20 pages.
Petition in Japanese Patent Application No. 2014-092382, dated Dec. 26, 2014, 9 pages.
Petition filed in Egyptian Patent Application No. PCT1637/2011, dated Sep. 28, 2021, 4 pages (with Partial English Translation).
Poujol et al., "Stability of the ready-to use solutions of eribulin for intravenous infusion," Annales pharmaceutiques françaises, 2012, 70(5):249-255.
Preliminary Amendment filed in Japanese Patent Application No. 2014-092382 dated May 28, 2014, 4 pages.
Preliminary Conclusion in Ukrainian Patent Application No. a201111426, dated Apr. 8, 2013, 8 pages.
Request for Appeal in Japanese Patent Application No. 2018-514683, dated Dec. 7, 2021, 18 pages.
Request for Continued Examination and Amendment in U.S. Appl. No. 14/061,426, dated Aug. 17, 2021, 21 pages.
Request for Continued Examination in U.S. Appl. No. 17/067,302, dated Apr. 12, 2021, 1 page.
Request for Examination in Brazilian Patent Application No. PI10145273, dated Dec. 27, 2011, 6 pages.
Request for Examination in Chinese Patent Application No. 201080014698.2, dated Sep. 29, 2011, 5 pages.
Request for Examination in Chinese Patent Application No. 201880024121.6, dated Oct. 9, 2019, 2 pages.
Request for Examination in Colombian Patent Application No. 11-130828, dated Jul. 17, 2012, 2 pages.
Request for Examination in Egyptian Patent Application No. PCT1637-2011, dated Oct. 3, 2011, 1 page.
Request for Examination in Indian Patent Application No. 6850-DELNP-2011, dated Sep. 7, 2011, 6 pages.
Request for Examination in Indonesian Patent Application No. W-00201103470, dated Sep. 29, 2011, 2 pages.
Request for Examination in Japanese Patent Application No. 2011-507239, dated Jan. 10, 2013, 2 pages.
Request for Examination in Japanese Patent Application No. 2011-507240, dated Jan. 10, 2013, 2 pages.
Request for Examination in Japanese Patent Application No. 2014-92382, dated May 28, 2014, 2 pages.
Request for Examination in Japanese Patent Application No. 2018-514683, dated Apr. 17, 2020, 2 pages.
Request for Examination in Malaysian Patent Application No. PI2011004382, dated Sep. 15, 2011, 1 page.
Request for Examination in Russian Patent Application No. 2011139715, dated Sep. 29, 2011, 2 pages.
Request for Examination in Taiwanese Patent Application No. 147388, dated Mar. 30, 2013, 9 pages.
Request for Examination in Ukrainian Patent Application No. a201111426, dated Feb. 1, 2013, 2 pages.
Response filed in Philippine Patent Application No. 1-2011-501838, dated Sep. 18, 2015 to the Office Action dated Aug. 27, 2015, 1 page.
Response filed in Philippine Patent Application No. 1-2011-501838, dated Sep. 30, 2013 to the Office Action dated Aug. 8, 2013, 1 page.
Response filed in Russian Patent Application No. 2011139715/20(059371), dated Jan. 30, 2012, 12 pages (with partial English Translation).
Response filed in Ukrainian Patent Application No. a201111426, dated Jun. 11, 2013, to the Office Action (Preliminary Conclusion on Non-patentability), 9 pages.
Response filed in U.S. Appl. No. 13/260,864, dated Mar. 9, 2016 to the Final Office Action dated Nov. 20, 2015, including Amendment, 16 pages.
Response filed in U.S. Appl. No. 13/260,864, dated May 26, 2015, including Supplemental Amendment, Statement of Substance of Interview, and Applicant-Initiated Interview Summary dated Apr. 27, 2015, 17 pages.
Response filed in U.S. Appl. No. 13/260,864, dated Oct. 13, 2015, to the Non-Final Office Action dated Jul. 13, 2015, 17 pages.
Response filed in U.S. Appl. No. 14/061,426, dated Aug. 26, 2019 to the Final Office Action dated May 30, 2019, 7 pages.
Response filed in U.S. Appl. No. 14/061,426, dated Aug. 30, 2017 to the Office Action dated May 31, 2017, 48 pages.
Response filed in U.S. Appl. No. 14/061,426, dated Dec. 23, 2019 to the Final Office Action dated May 30, 2019, 50 pages.
Response filed in U.S. Appl. No. 14/061,426, dated Feb. 26, 2021, 27 pages.
Response filed in U.S. Appl. No. 14/061,426, dated Feb. 7, 2019, to the Office Action dated Nov. 19, 2018, 23 pages.
Response filed in U.S. Appl. No. 14/061,426, dated Mar. 17, 2020 to the Examiner's Answer dated Feb. 28, 2020, 3 pages.
Response filed in U.S. Appl. No. 16/090,360, dated Feb. 26, 2021, 11 pages.
Response filed in U.S. Appl. No. 16/090,360, dated Jul. 13, 2020, to the Final Office Action dated Mar. 11, 2020, 9 pages.
Response filed in U.S. Appl. No. 16/090,360, dated Sep. 21, 2021, 14 pages.
Response filed in U.S. Appl. No. 16/835,719, dated Sep. 29, 2020, 10 pages.
Response filed in U.S. Appl. No. 17/067,302, dated Mar. 19, 2021, 15 pages.
Response filed in Vietnamese Patent Application No. 1-2011-02950, dated Dec. 13, 2013, 8 pages.
Response filed in Vietnamese Patent Application No. 1-2011-02950, dated May 30, 2016, 4 pages.
Restriction Requirement in U.S. Appl. No. 16/341,579, dated Mar. 4, 2021, 10 pages.
Satsuka, "Recent evolution of liposome application," NTS, 2005, 16 pages.

(56) References Cited

OTHER PUBLICATIONS

Schmidt et al., "Assessment of Clinical Activity of PD-1 Checkpoint Inhibitor Combination Therapies Reported in Clinical Trials," JAMA Network Open Feb. 2020, 3(2):e1920833.
Shimauchi et al., "Augmented expression of programmed death-1 in both neoplastic and non-neoplastic CD4+ T-cells in adult T-cell leukemia/lymphoma," Int. J. Cancer, 2007, 121:2585-2590.
Takahashi et al., "One-year follow-up results of eribulin for softtissue sarcoma including rare subtypes in a real-world observational study in Japan," Poster Display, Abstract No. 1683P displayed Sep. 28, 2019, European Society tor Medical Oncology (ESMO) 2019 Congress, Barcelona, Spain, 1 page.
Tamura et al., "Phase 1 study of the liposomal formulation of eribulin (E7389-LF): Results from the HER2-negative breast cancer expansion part," Eposter for Abstract 346P, presented at the European Society for Medical Oncology (ESMO) Virtual Congress, Sep. 19-21, 2020, Annals of Oncology (2020) 31 (suppl_4):S348-S395, 10.1016/annonc/annonc268, 1 page.
Tamura et al., "Phase 1 study of the liposomal formulation of eribulin (E7389-LF): Results from the HER2-negative breast cancer expansion," Abstract 346P, dated Sep. 17, 2020, the European Society for Medical Oncology (ESMO) Virtual Congress, Sep. 19-21, 2020, Annals of Oncology (2020) 31 (suppl_4):S348-S395, 10.1016/annonc/annonc268, 7 pages.
Tolaney et al., "Abstract PD6-13: Phase 1b/2 study to evaluate eribulin mesylate in combination with pembrolizumab in patients with metastatic triple-negative breast cancer," Cancer Research, Feb. 2018, vol. 78, 4 pages.
Request for Examination in Vietnamese Patent Application No. 1-2011-02950, dated Oct. 31, 2011, 6 pages.
Resolution in Peruvian Patent Application No. 001735-2011/DIN, dated Nov. 30, 2015, 50 pages.
Response filed in Algerian Patent Application No. 110640, dated Aug. 29, 2016, 26 pages.
Response filed in Brazilian Patent Application No. P110145273, dated Jul. 2, 2020, to the Office Action dated Mar. 30, 2020, 80 pages.
Response filed in Brazilian Patent Application No. P110145273, dated Oct. 6, 2020, to the Office Action dated Jul. 14, 2020, 20 pages.
Response filed in Canadian Patent Application No. 2756811, dated Jun. 19, 2013 to the Office Action dated Dec. 19, 2012, 21 pages.
Response filed in Chilean Patent Application No. 2444-2011, dated Apr. 16, 2015 to the Office Action dated Jan. 21, 2015, 142 pages.
Response filed in Chilean Patent Application No. 2444-2011, dated Jun. 5, 2015, 8 pages.
Response filed in Chilean Patent Application No. 2444-2011, dated Mar. 11, 2014 to the Opposition dated Jan. 2014, 6 pages.
Response filed in Chilean Patent Application No. 2444-2011, dated Mar. 14, 2016 to the Office Action dated Dec. 11, 2015, 12 pages.
Response filed in Chinese Patent Application No. 201080014698.2, dated Dec. 23, 2013 to Office Action dated Aug. 8, 2013, 14 pages.
Response filed in Chinese Patent Application No. 201080014698.2, dated May 29, 2014 to the Office Action dated Mar. 28, 2014, 13 pages.
Response filed in Colombian Patent Application No. 11-130828, dated Dec. 2, 2013, 24 pages.
Response filed in Colombian Patent Application No. 11-130828, dated Jan. 14, 2013 to the Opposition dated Jul. 25, 2012, 10 pages.
Response filed in Egyptian Patent Application No. PCT1637/2011, dated Apr. 18, 2016, 20 pages.
Response filed in Egyptian Patent Application No. PCT1637/2011, dated Mar. 25, 2021, 26 pages.
Response filed in Egyptian Patent Application No. PCT1637/2011, dated Mar. 30, 2017, to the Office Decision dated Jan. 3, 2017, 21 pages.
Response filed in European Patent Application No. 10758754.5, dated Aug. 1, 2014 to Communication to Art 94(3) dated Jan. 24, 2014, 15 pages.
Response filed in European Patent Application No. 10758754.5, dated May 3, 2013 to the Office Action dated Oct. 25, 2012 and to the EESR issued on Oct. 8, 2012, 8 pages.
Response filed in European Patent Application No. 10758755.2, dated Jun. 3, 2014 to the Office Action dated Jan. 24, 2014, 82 pages.
Response filed in European Patent Application No. 17789632.1, dated Jun. 24, 2020, to the Communication Pursuant to Rules 70(2)/70a(2) EPC dated Dec. 17, 2019, including Amendment, 5 pages.
Response filed in European Patent Application No. 17789632.1, dated Nov. 11, 2021, to the Communication pursuant to Article 94(3) EPC dated Sep. 20, 2021, 21 pages.
Response filed in Indian Patent Application No. 6850/DELNP/2011, dated Oct. 3, 2017 to Result for Hearing Notice, including Amendment, 320 pages.
Response filed in Indonesian Patent Application No. W00201103470, dated Mar. 25, 2014, 7 pages.
Response filed in Japanese Patent Application No. 2011-507239, dated Apr. 28, 2014 to the Office Action dated Feb. 27, 2014, 5 pages.
Response filed in Japanese Patent Application No. 2011-507240, dated Apr. 7, 2014 to the Office Action dated Feb. 6, 2014, 26 pages.
Response filed in Japanese Patent Application No. 2014-092382, dated Mar. 27, 2015 to the Office Action dated Jan. 28, 2015, including Amendment and argument, 13 pages.
Response filed in Japanese Patent Application No. 2018-514683, dated Aug. 5, 2021 to the Office Action dated Apr. 7, 2021, 10 pages.
Response filed in Korean Patent Application No. 10-2011-7022860, dated Dec. 24, 2014 to the Notice of Final Rejection dated Sep. 23, 2014, 18 pages.
Response filed in Korean Patent Application No. 10-2011-7022860, dated Feb. 28, 2013 to the Office Action dated Dec. 28, 2012, 31 pages.
Response filed in Korean Patent Application No. 10-2011-7022860, dated Jan. 22, 2014 to the Office Action dated Jul. 22, 2013, 31 pages.
Response filed in Korean Patent Application No. 10-2011-7022860, dated Jul. 18, 2014 to the Office Action dated May 20, 2014, including amendment, 15 pages.
Response filed in Malaysian Patent Application No. PI2011004382, dated Jun. 14, 2013 to Substantive Examination Adverse Report dated Apr. 15, 2013, 6 pages.
Response filed in Mexican Patent Application No. MX/a/2011/009632 dated Jan. 7, 2013, to the Office Action dated Aug. 7, 2012, 17 pages.
Response filed in Mexican Patent Application No. MX/a/2011/009632, dated Jun. 17, 2014, 22 pages.
Response filed in Mexican Patent Application No. MX/a/2011/009632, dated Sep. 18, 2013 to the Office Action dated Apr. 22, 2013, 20 pages.
Response filed in Peruvian Patent Application No. 001735-2011/DIN, dated Aug. 12, 2015 18 pages.
Response filed in Peruvian Patent Application No. 001735-2011/DIN, dated Jan. 20, 2014, 2 pages.
Response filed in Peruvian Patent Application No. 001735-2011/DIN, dated Jan. 21, 2013 to the Peruvian Opposition issued Nov. 23, 2012, 5 pages.
Response filed in Peruvian Patent Application No. 001735-2011/DIN, dated May 20, 2015, 48 pages.
Response filed in Peruvian Patent Application No. 001735-2011/DIN, dated Oct. 27, 2014 to Office Action dated Sep. 29, 2014, 3 pages.
Response filed in Peruvian Patent Application No. 001798-2015, dated Jan. 4, 2020 to the Observation received on Oct. 16, 2019, 12 pages.
Response filed in Peruvian Patent Application No. 001798-2015, dated Jul. 23, 2020, 15 pages.
Response filed in Peruvian Patent Application No. 1798-2015, dated Apr. 28, 2016, 10 pages.
"Ammonium Cations," The Illustrated Glossary of Organic Chemistry, [Retrieved on Mar. 9, 2016], retrieved from: URL<http://www.chem.ucla.edu/harding/IGOC/A/ammonium_cation.html>, 1 page.

(56) References Cited

OTHER PUBLICATIONS

"Halaven Intravenour Injection 1 mg," Package Insert for Halaven, Eisai, Ltd., Jul. 2011, 6 pages (with partial English Translation).
"Novantron Infection 10mg, 20mg," Package Insert, ASKA Pharmaceutical Co., Ltd., Nov. 2011, 6 pages (with partial English Translation).
"PBA2021—31st International Symposium on Pharmaceutical and Biomedical Analysis—Aug. 29 (Sun)-Sep. 1 (Wed), Kyoto University at Katsura, Kyoto, Japan," available on or before Oct. 5, 2021, [Retrieved on Sep. 17, 2021], retrieved from: URL<http://soyaku.phar.kyushu-u.ac.jp/PBA2021/index.html#:~:text=The%20conference%20will%20be%20held,for%20Pharmaceutical%20and%20Biomedical%20Analysis.&text=We%20encourage%20also%20the%20young,meeting%20and%20present%20the%20results.>, 2 pages.
WHO Drug Information, 2013, vol. 27, No. 1, pp. 68-69.
WHO Drug Information, 2013, vol. 27, No. 2, pp. 161-162.
Adams et al., "Phase 2 study of pembrolizumab (pembro) monotherapy for previously treated metastatic triple-negative breast cancer (mTNBC): KEYNOTE-086 cohort A," Journal of Clinical Oncology, 2017, 35(15 suppl):1008.
Adams et al., "Phase 2 study of pembrolizumab as first-line therapy for PD-L1-positive metastatic triple-negative breast cancer (mTNBC): Preliminary data from KEYNOTE-086 cohort B," Journal of Clinical Oncology, 2017, 35(15 suppl):1088.
Ahmadzadeh et al., "Tumor antigen-specific CD8 T cells infiltrating the tumor express high levels of PD-1 and are functionally impaired," Blood, 2009, 114(8):1537-1544.
Amendment filed in Japanese Patent Application No. 2018-514683, dated Dec. 7, 2021, 2 pages.
Applicant Observation filed in Chinese Patent Application No. 201080014698.2, dated Apr. 2, 2013 to the first Chinese Office Action dated Oct. 24, 2012, 48 pages.
Arima et al., "Enhancement of antitumor effect of doxorubicin by its complexation with γ-cyclodextrin in pegylated liposomes," Journal of Drug Targeting, 2006, 14(4):225-232.
Beijnen et al., "Aspects of the degradation kinetics of doxorubicin in aqueous solution," International Journal of Pharmaceutics, Elsevier, 1986, 32:123-131.
ClinicalTrials.gov [online], "A Study of E7389 Liposomal Formulation (E/389-LF) Plus Nivolumab in Participants with Solid Tumor, History of Changes for Study: NCT04078295," Sep. 2019, retrieved from: URL<https://clinicaltrials.gov/ct2/history/NCT04078295?V_1=View#StudyPageTop, Sep. 2, 2019>, 4 pages.
ClinicalTrials.gov [online], "Study NCT01848834—Study of MK-3475 in Participants With Advanced Solid Tumors (MK-3475-012/KEYNOTE-012," Apr. 2014, retrieved from: URL<https://clinicaltrials.gov/ct2/history/NCT01848834?V_24=View>, 7 pages.
Communication pursuant to Article 94(3) EPC in European Patent Application No. 17789632.1, dated Sep. 20, 2021, 4 pages.
Communication under Rule 71(3) EPC in European Patent Application No. 10758755.2, dated Feb. 25, 2016, 7 pages.
Decision on Grant in Russian Application No. 2011139715, dated Sep. 25, 2012, 14 pages.
Decision to Grant in Japanese Patent Application No. 2011-507239, dated Aug. 27, 2014, 5 pages.
Decision to Grant in Japanese Patent Application No. 2011-507240, dated May 7, 2014, 5 pages.
Decision to Grant in Japanese Patent Application No. 2014-092382, dated Jun. 2, 2015, 6 pages.
Decision to Grant in Thai Patent Application No. 1101002341, dated Nov. 15, 2021, 2 pages (with English Translation).
Dong et al., "Tumor-associated B7-H1 promotes T-cell apoptosis: A potential mechanism of immune evasion," Natural Medicine, 2002, 8(8):793-800.
Eisai Co., Ltd., "FY2011 Financial Results Presentation," May 15, 2012, 68 pages.
Eisai Co., Ltd., "Halaven®," Code DI-T-HAL107, 6th edition, Feb. 2016, pp. 1-6.
Eisai Co., Ltd., Eisai Public Relations Department, "Eisai and Merck Enter Collaboration to Explore Novel Combination Regimens of Anti-PD-1 Therapy with Multi-targeting RTK Inhibitor and Microtubule Dynamics in Multiple Types of Cancer," Mar. 4, 2015, retrieved from: URL<http//www.eisai.com/news/news201518.html>, 8 pages.
Eisai Co., Ltd., News Release No. 21-37, "Eisai to Present Data on Oncology Pipeline and Products at ASCO Annual Meeting," dated May 20, 2021, 5 pages.
Eisai Co., Ltd., News Release No. 21-73, "Eisai to Present Abstracts on Oncology Products and Pipeline at ESMO Virtual Congress 2021," dated Sep. 14, 2021, 3 pages.
Tolaney et al., "Phase 1b/2 study to evaluate eribulin mesylate in combination with pembrolizumab in patients with metastatic triple-negative breast cancer," [Abstract No. 177], Eur. J Cancer, 2017, 72:S16.
Written Opinion in International Patent Application No. PCT/JP2018/020456, dated Aug. 28, 2018, 15 pages.
Written Opinion in Singaporean Patent Application No. 11201706872S, dated Jun. 27, 2018, 7 pages.
Written Opinion in Singaporean Patent Application No. 11201706872S, dated Nov. 5, 2019, 10 pages.
Yamaguchi et al., "Phase 1 study of the liposomal formulation of eribulin (E7389-LF): Results from the advanced gastric cancer expansion cohort," Abstract, 2021 ASCO Annual Meeting, Journal of Clinical Oncology, 2021, 39(Suppl. 15):4025.
Yamaguchi et al., "Phase 1 study of the liposomal formulation of eribulin (E7389-LF): Results from the advanced gastric cancer expansion cohort," Poster Display, Abstract No. 4025, displayed Jun. 4-8, 2021, 2021 ASCO Annual Meeting, Journal of Clinical Oncology, 2021, 1 page.
Yamamoto et al., "Phase 1b study of a liposomal formulation of eribulin (E7389-LF)+nivolumab (Nivo) in patients (pts) with advanced solid tumors," Abstract, ESMO Congress 2021, Annals of Oncology, 2021, 32(Suppl_5):S829-S866, 2 pages.
Yamamoto et al., "Phase 1b study of a liposomal formulation of eribulin (E7389-LF)+nivolumab (Nivo) in patients (pts) with advanced solid tumors," Poster Display, Poster No. 980P, displayed Sep. 16-21, 2021, ESMO Congress 2021, Annals of Oncology, 2021, 1 page.
Yang et al., "PD-L1 Interaction Contributes to the Functional Suppression of T-Cell Responses to Human Uveal Melanoma Cells In Vitro," Invest. Ophthalmol. Vis. Sci., 2008, 49(6):2518-2525.
Yi et al., "Biomarkers for predicting efficacy of PD-1/PD-L1 inhibitors," Molecular Cancer, 2018, 17:129.
Yin et al., "Enhanced Permeability and Retention (EPR) Effect Based Tumor Targeting: The Concept, Application and Prospect," JSM Clinical Oncology and Research, 2014, 2(1):1010.
Office Action in Russian Patent Application No. 2017132877, dated Aug. 29, 2019, 12 pages.
Office Action in Russian Patent Application No. 2017132877, dated Jan. 27, 2020, 8 pages.
Office Action in Russian Patent Application No. 2019114459/04, dated Dec. 8, 2020, 12 pages.
Office Action in Russian Patent Application. No. 2011139715/20(059371), dated Nov. 28, 2011, (with partial English Translation), with Applicant Response filed on Jan. 30, 2012, 4 pages.
Office Action in Taiwanese Patent Application No. 099109838, dated Jun. 22, 2012, 9 pages.
Office Action in U.S. Appl. No. 15/554,540, dated Mar. 22, 2019, 27 pages.
Office Action in U.S. Appl. No. 16/090,360, dated Mar. 11, 2020, 9 pages.
Office Action in U.S. Appl. No. 16/090,360, dated Oct. 2, 2020, 31 pages.
Office Action in U.S. Appl. No. 16/090,360, dated Oct. 21, 2019, 8 pages.
Office Action in U.S. Appl. No. 16/090,360, dated Oct. 13, 2021, 10 pages.
Office Action in U.S. Appl. No. 17/067,302, dated Dec. 30, 2020, 58 pages.
Office Action in Vietnamese Patent Application No. 1-2011-02950, dated Aug. 16, 2013, 3 pages.
Office Action in Vietnamese Patent Application No. 1-2011-02950, dated Mar. 31, 2016, 3 pages.

(56) References Cited

OTHER PUBLICATIONS

Official Decision in Egyptian Patent Application No. PCT1637/2011, dated Dec. 29, 2020, 10 pages.
Official Decision in Egyptian Patent Application No. PCT1637/2011, dated Jan. 3, 2017, 8 pages.
Official Decision in Egyptian Patent Application No. PCT1637/2011, dated Aug. 10, 2021, 8 pages.
Official Notification in Peruvian Patent Application No. 001735-2011/DIN, dated Jul. 16, 2015, 28 pages.
Official Notification in Vietnamese Patent Application No. 1-2011-02950, dated Jan. 24, 2017, 2 pages.
Ohigashi et al., "Clinical Significance of Programmed Death-1 Ligand-1 and Programmed Death-1 Ligand-2 Expression in Human Esophageal Cancer," Clin. Cancer Res., 2005, 11(8):2947-2953.
Opposition in Colombian Patent Application No. 11-130828, dated Apr. 30, 2012, 14 pages.
Opposition in Colombian Patent Application No. 11-130828, dated Jul. 25, 2012, 14 pages.
Opposition in Peruvian Patent Application No. 001735-2011/DIN, dated Jan. 20, 2015, 25 pages.
Opposition in Peruvian Patent Application No. 001798-2015, dated Jan. 25, 2016, 18 pages.
Patent Certificate for Australian Patent No. 2014200717, granted on Jun. 9, 2016, 1 page.
Patent Certificate for Canadian Patent No. 2,756,811, granted on Sep. 23, 2014, 2 pages.
Patent Certificate for Chilean Patent No. 56.288, granted on Jul. 3, 2018, 2 pages.
Patent Certificate for Chinese Patent No. ZL201080014698.2, granted on Oct. 29, 2014, 3 pages.
Patent Certificate for Colombian Patent No. 4584, granted on Jan. 17, 2014, 2 pages.
Notification of the Brazilian Patent and Trademark Office and Documents forwarded by ANVISA (Brazilian Health Surveillance Agency) for Brazilian Patent Application No. PI1014527-3, including transmittal letter (dated Jul. 31, 2019); Technical Written Opinion of Consent of a Patent Application of Pharmaceutical products and Processes (Jul. 18, 2019), supporting documents (Jul. 24, 2019), and "Documents Forwarded by ANVIA" (Sep. 5, 2019).
Observation Notification in Peruvian Patent Application No. 001798-2015, dated Feb. 12, 2020, 11 pages.
Observation Notification in Peruvian Patent Application No. 001798-2015, dated Oct. 16, 2019, 15 pages.
Office Action in Australian Patent Application No. 2016226157, dated Jan. 29, 2021, 5 pages.
Office Action in Brazilian Patent Application No. PI10145273, dated Jul. 14, 2020, 9 pages.
Office Action in Brazilian Patent Application No. PI10145273, dated Mar. 30, 2020, 24 pages.
Office Action in Canadian Patent Application No. 2756811, dated Dec. 19, 2012, 4 pages.
Office Action in Chilean Patent Application No. 2444-2011, dated Jan. 16, 2014, 6 pages.
Office Action in Chilean Patent Application No. 2444-2011, dated Jan. 21, 2015, 20 pages.
Office Action in Chilean Patent Application No. 2444-2011, dated Jul. 11, 2013, 19 pages.
Office Action in Chilean Patent Application No. 2444-2011, dated Dec. 18, 2015, 15 pages.
Office Action in Chinese Patent Application No. 201080014698.2 dated Oct. 24, 2012, 14 pages.
Office Action in Chinese Patent Application No. 201080014698.2, dated Aug. 8, 2013, 12 pages.
Office Action in Chinese Patent Application No. 201080014698.2, dated Mar. 28, 2014, 6 pages.
Office Action in Chinese Patent Application No. 201680025588.3, dated Jan. 6, 2020, 28 pages.
Office Action in Chinese Patent Application No. 201680025588.3, dated Jul. 7, 2020, 29 pages.
Office Action in Colombian Patent Application No. 11-130828, dated Aug. 8, 2013, 30 pages.
Office Action in Egyptian Patent Application No. PCT1637/2011, dated Jan. 14, 2016, 10 pages.
Office Action in European Patent Application No. 10758754.5, dated Jan. 24, 2014, 7 pages.
Office Action in Indian Patent Application No. 201747034283, dated Feb. 28, 2020, 7 pages.
Office Action in Indian Patent Application No. 201747034283, dated Mar. 30, 2021, 3 pages.
Office Action in Indian Patent Application No. 6850DELNP2011, dated Nov. 10, 2016, 9 pages.
Office Action in Indonesian Patent Application No. W0020113470, dated Nov. 29, 2013, 7 pages.
Office Action in Israeli Patent Application No. 215059, dated Aug. 4, 2014, 3 pages.
Office Action in Israeli Patent Application No. 254133, dated Oct. 14, 2020, 7 pages (with partial translation).
Office Action in Japanese Patent Application No. 2017-546075, dated Jan. 7, 2020, 6 pages.
Office Action in Japanese Patent Application No. 2017-546075, dated Jul. 21, 2020, 6 page.
Office Action in Japanese Patent Application No. 2017-546075, dated Mar. 23, 2021, 7 pages.
Office Action in Japanese Patent Application No. 2018-514683, dated Apr. 7, 2021, 9 pages.
Office Action in Korean Patent Application No. 10-2011-7022860, dated Jul. 22, 2013, 20 pages.
Office Action in Korean Patent Application No. 10-2011-7022860, dated May 20, 2014, 11 pages.
Office Action in Korean Patent Application No. 10-2011-7022860, Notice of Preliminary Rejection, dated Dec. 28, 2012, 7 pages.
Office Action in Mexican Patent Application No. MX/a/2011/009632, dated Apr. 22, 2013, 12 pages.
Office Action in Mexican Patent Application No. MX/a/2011/009632, dated Aug. 7, 2012, 6 pages.
Office Action in Mexican Patent Application No. MX/a/2011/009632, dated Jan. 17, 2014, 6 pages.
Office Action in Mexican Patent Application No. MX/a/2017/011206, dated Mar. 12, 2021, 8 pages.
Office Action in Peruvian Patent Application No. 001735-2011/DIN, dated Jan. 9, 2014, 2 pages.
Office Action in Peruvian Patent Application No. 001735-2011/DIN, dated Nov. 23, 2012, 15 pages.
Office Action in Peruvian Patent Application No. 001735-2011/DIN, dated Sep. 29, 2014, 7 pages.
Mano, "A separate determination of released and liposomal encapsulated eribulin in dog plasma by LC-MS/MS for its application to a pharmacokinetic study," Abstract, Global Drug Metabolism and Pharmacokinetics, Eisai Co., Ltd., Japan, 31st International Symposium on Pharmaceutical and Biomedical Analysis, Aug. 2021, 1 page.
Mano, "A separate determination of released and liposomal encapsulated eribulin in dog plasma by LC-MS/MS for its application to a pharmacokinetic study," Poster Display, Poster No. P-1, displayed Aug. 30, 2021, Global Drug Metabolism and Pharmacokinetics, Eisai Co., Ltd., Japan, 31st International Symposium on Pharmaceutical and Biomedical Analysis, 1 page.
Masuda et al., "Phase 1 Expansion Study of Liposomal Formulation of Eribulin (E7389-LF) for Solid Tumors: Focus on Breast Cancer," Abstract, The Japanese Society of Medical Oncology Annual Meeting, Feb. 10, 2021, p. 670.
Masuda et al., "Phase 1 Expansion Study of Liposomal Formulation of Eribulin (E7389-LF) for Solid Tumors: Focus on Breast Cancer," Presentation, The Japanese Society of Medical Oncology Annual Meeting, Feb. 21, 2021, 17 pages.
Merck Sharp & Dohme Corp., "Highlights of Prescribing Information—KEYTRUDA® (pembrolizumab)," Label, Suppl. 8, revised Oct. 2016, FDA Ref. ID: 4003165, retrieved from: URL<https://www.accessdata.fda.gov/drugsatfda_docs/label/2016/125514s008s012lbl.pdf>, 29 pages.
Merck Sharp & Dohme Corp., "Highlights of Prescribing Information—KEYTRUDA® (pembrolizumab)," Label, Suppl. 9, revised Aug.

(56) References Cited

OTHER PUBLICATIONS

2016, FDA Ref. ID: 3968676, retrieved from: URL<https://www.accessdata.fda.gov/drugsatda_docs/label/2016/125514s009lbl.pdf>, 26 pages.
Nakanishi et al., "Overexpression of B7-H1 (PD-L1) significantly associates with tumor grade and postoperative prognosis in human urothelial cancers," Cancer Immunol Immunother., 2007, 56:1173-1182.
Nanda et al., "Pembrolizumab in Patients With Advanced Triple-Negative Breast Cancer: Phase Ib KEYNOTE-012 Study," Journal of Clinical Oncology, 2016, 34(21):2460-2467.
Nomi et al., "Clinical Significance and Therapeutic Potential of the Programmed Death-1 Ligand/Programmed Death-1 Pathway in Human Pancreatic Cancer," Clin. Cancer Res., 2007, 13(7):2151-2157.
Notice of Allowance in Brazilian Patent Application No. PI10145273, dated Oct. 20, 2020, 2 pages.
Notice of Allowance in Canadian Patent Application No. 2756811, dated Feb. 10, 2014, 1 page.
Notice of Allowance in Chilean Patent Application No. 2444-2011, dated Jul. 3, 2018, 8 pages.
Notice of Allowance in Chinese Patent Application No. 201080014698.2, dated Aug. 6, 2014, 4 pages.
Notice of Allowance in Colombian Patent Application No. 11-130828, dated Jan. 21, 2014, 12 pages.
Notice of Allowance in Indonesian Patent Application No. W00201103470 dated Apr. 20, 2017, 4 pages.
Notice of Allowance in Israeli Patent Application No. 215059, dated Nov. 25, 2015, 3 pages.
Notice of Allowance in Israeli Patent Application No. 254133, dated Jun. 3, 2021, 5 pages.
Notice of Allowance in Korean Patent Application No. 10-2011-7022860, dated Jan. 9, 2015, 4 pages.
Notice of Allowance in Mexican Patent Application No. MX/A/2011/009632, dated Oct. 14, 2014, 2 pages.
Notice of Allowance in Taiwanese Patent Application No. 099109838, dated Jan. 23, 2013, 5 pages.
Notice of Allowance in Ukrainian Patent Application No. a201111426, dated Jul. 23, 2013, 7 pages.
Notice of Allowance in U.S. Appl. No. 16/835,719, dated Jan. 22, 2021, 10 pages.
Notice of Allowance in U.S. Appl. No. 16/835,719, dated Jun. 14, 2021, 12 pages.
Notice of Allowance in U.S. Appl. No. 17/067,302, dated Mar. 31, 2021, 8 pages.
Notice of Allowance in U.S. Appl. No. 17/067,302, dated May 28, 2021, 11 pages.
Notice of Final Rejection in Japanese Patent Application No. 2018-514683, dated Sep. 15, 2021, 6 pages.
Notice of Final Rejection in Korean Patent Application No. 10-2011-7022860, dated Sep. 23, 2014, 5 pages.
Notice of Intention to Refuse Patent Application in Singaporean Patent Application No. 11201706872S, dated Nov. 19, 2020, 11 pages.
Notice of Reason for Rejection in Japanese Patent Application No. 2011-507239, dated Feb. 27, 2014, 6 pages.
Notice of Reason for Rejection in Japanese Patent Application No. 2011-507240, dated Feb. 6, 2014, 7 pages.
Notice of Reason for Rejection in Japanese Patent Application No. 2014-092382, dated Jan. 28, 2015, 5 pages.
International Preliminary Report on Patentability and Written Opinion issued in counterpart International Patent Application No. PCT/JP2020/028663 dated Feb. 10, 2022.
Response to Communication filed in counterpart European Patent Application No. 20847524.4 dated Jul. 25, 2022.
Notice of Allowance issued in counterpart South African Patent Application No. 2021/10686 dated Jul. 8, 2022.
Office Action issued in Israeli Patent Application No. 289213 dated Aug. 9, 2022.
Submission Document filed in counterpart South African Patent Application No. 2021/10686 dated Aug. 31, 2022.
Office Action issued in counterpart Chinese Patent Application No. 202080042486.9 dated Sep. 26, 2022.
Submission Documents Before the Patent Office filed in counterpart Israeli Patent Application No. 289213 dated Oct. 13, 2022.
Niwa et al. "Antitumor activity of liposomal formulation of eribulin combined with anti-PD-1" American Association for Cancer Research Annual Meeting 2022, Poster Apr. 8, 2022.
Niwa et al. "Abstract 5584: Antitumor activity of liposomal formulation of eribulin combined with anti-PD-1" Cancer Res (2022) 82 (12_Supplement): 5584. Jun. 15, 2022.
Tanioka et al. "Anti-tumor activity of a liposomal formulation of Eribulin compared with the same dose of Eribulin in patient-derived breast cancer xenografts" San Antonio Breast Cancer Symposium—45th Annual Meeting, Abstract Nov. 21, 2022.
Ooki et al. "The esophageal cancer cohort of a phase 2 trial of E7389-LF (liposomal formulation of eribulin) + nivolumab." American Society of Clinical Oncology—Gastrointestinal Cancers Symposium 2023, Abstract Jan. 17, 2023.
Muro et al. "Gastric cancer (GC) cohort of a phase 2 trial of E7389-LF (liposomal formulation of eribulin) in combination with nivolumab." American Society of Clinical Oncology—Gastrointestinal Cancers Symposium 2023, Abstract Jan. 17, 2023.
Tanioka et al. "Anti-tumor activity of a liposomal formulation of Eribulin compared with the same dose of Eribulin in patient-derived breast cancer xenografts" San Antonio Breast Cancer Symposium—45th Annual Meeting, Poster Dec. 7, 2022.
Niwa et al. "Liposome-encapsulated eribulin shows enhanced antitumour activity over eribulin for combination therapy with anti-PD-1 antibody" Mol Cancer Ther https://doi.org/10.1158/1535-7163.MCT-22-0475 Jan. 24, 2023.
Shitara et al. "Phase I Study of the Liposomal Formulation of Eribulin (E7389-LF): Results from the Advanced Gastric Cancer Expansion Cohort" Clinical Cancer Research OF1-OF8. https://doi.org/10.1158/1078-0432.CCR-22-3027 Feb. 28, 2023.
Muro et al. "Gastric cancer (GC) cohort of a phase 2 trial of E7389-LF (liposomal formulation of eribulin) in combination with nivolumab." American Society of Clinical Oncology—Gastrointestinal Cancers Symposium 2023, Poster Jan. 17, 2023.
Ooki et al. "The esophageal cancer cohort of a phase 2 trial of E7389-LF (liposomal formulation of eribulin) + nivolumab." American Society of Clinical Oncology—Gastrointestinal Cancers Symposium 2023, Poster Jan. 17, 2023.
Office Action issued in related Chinese Patent Application No. 202080042486.9 dated Mar. 10, 2023.
Twelves et al., "Efficacy of eribulin in women with metastatic breast cancer: a pooled analysis of two phase 3 studies," Breast Cancer Research and Treatment, 148: 553-561 (2014).
Mullard, "Learning from the 2012-2013 class of breakthrough therapies," Nature Reviews, 12: 891-893 (Dec. 2013).
Press Release Merck, Jul. 2013, "PD-1 inhibitor becomes 'Breakthrough Therapy'", Cancer Discovery 10.
Press Release Merck, Apr. 2013, "Merck announces breakthrough therapy designation for lambrolizumab an investigational antibody therapy for advanced melanoma".
Dolgin, "Cancer's true breakthroughs" Nature Medicine, vol. 19(6): 660-663 (Jun. 2013).
Mittendorf et al., "PD-L1 Expression in Triple-Negative Breast Cancer," American Association for Cancer Research, 361-370 (2014).
History of Changes for Study: NCT02039674: A study of pembrolizumab (MK-3475) in combination with chemotherapy or immunotherapy in participants with non-small cell lung cancer (MK-3475-021/KEYNOTE-021)—Jan. 2015.
History of Changes for Study: NCT02036502 Study of Pembrolizumab (MK-3475) in Combination With Lenalidomide and Dexamethasone in Participants With Multiple Myeloma (MK-3475-023/KEYNOTE023)—Jan. 2015.
History of Changes for Study: NCT02331368 Phase 2 Multi-center Study of Anti-PD-1 During Lymphopenic State After HIDT/ASCT for Multiple Myeloma.—Jan. 2015.

(56) References Cited

OTHER PUBLICATIONS

Robert et al., "LBA-Pembrolizumab (pembro; MK-3475) for advanced melanoma: Randomized comparison of two dosing schedules" Annals of Oncology, 25(5): 1-41 (Sep. 29, 2014).
Bai et al., "A guide to rational dosing of monoclonal antibodies," Clinical Pharmacokinetics, 51(2): 119-35 (Feb. 2012).
Kaufman et al., "Efficacy or eribulin in patients (ots) with metastatic breast cancer (MBC): A pooled analysis by HER2 and ER status," Journal of Clinical Oncology, 32 (26): 137-137 (2014).
Feature listings of claims 1, 6, 7, and 13 of the opposed patent—filed in opposition against EP3265122 dated Feb. 3, 2023.
Bibliographic data of U.S. Appl. No. 62/128,373 (priority application) filed in opposition against EP3265122 dated Feb. 3, 2023.
Record of assignments of U.S. Appl. No. 62/128,373 (priority application) filed in opposition against EP3265122 dated Feb. 3, 2023.
Press release from Merck: dated May 30, 2014: Merck Announces Generic Name for MK-3475, Merck's Investigational anti-PD-1 Antibody: Pembrolizumab).
Mittendorf et al., PD-L1 Expression in Triple Negative Breast Cancer, Cancer Immunology Research; 2(4), 361-370 (Apr. 2014).
Clinical trial NCT02447003 (published on May 14, 2015).
Funahashi et al. "Eribulin mesylate reduces tumor microenvironment abnormality by vascular remodeling in preclinical human breast cancer models," Cancer Science, 105: 1334-1342 (2014).
Park et al., "Clinical Benefits of and Recent Progress in Eribulin Mesylate Therapy for Breast Cancer Patients," Journal pf Tumor, 2(4): 113-121 (Apr. 18, 2014).
Lehmann et al., "Identification and use of biomarkers in treatment strategies for triple-negative breast cancer subtypes," Journal of Pathology, 232: 142-150 (2014).
Vahdat et al. "Eribulin mesylate + trastuzumab as first-line therapy for locally recurrent or metastatic HER2-positive breast cancer: results from a phase 2, multicenter, single-arm study," Cancer Research, 72 (24): Supp. 3. Abstract No. PS-20-04 (Dec. 15, 2012).
Clinical trial NCT02142738 (published on Feb. 17, 2015).
Clinical trial NCT02039674 (published on Feb. 25, 2015).
Clinical trial NCT02305186 (published on Nov. 27, 2014).
Tolaney et al., "Phase 1b/2 study to evaluate eribulin mesylate in combination with pembrolizumab in patients with metastatic triple-negative breast cancer," European Journal of Cancer, 72, S16 Abstract No. 177 (2017).
Tolaney et al., "Abstract PD6-13: Phase 1b/2 study to evaluate eribulin mesylate in combination with pembrolizumab in patients with metastatic triple-negative breast cancer," Cancer Research, 78 (4 Suppl.), Abs. PD6-13 (2018).
Schmidt et al., "Assessment of Clinical Activity of PD-1 Checkpoint Inhibitor Combination Therapies Reported in Clinical Trials," JAMA Network Open, 3(2): e1920833 (2020).
Eisai News Release: "U.S. Fda Approves Eisai's Halaventm (Eribulin Mesylate) Injection for Treatment of Metastatic Breast Cancer" Nov. 16, 2010.
Merck News Release: "Merck Receives Accelerated Approval of Keytruda ® (pembrolizumab), the first FDA-Approved Anti-PD-1 Therapy" Sep. 4, 2014.
Meeting Reporter at 37th Annual San Antonio Breast Cancer Symposium, Oncology Times, Feb. 10, 2015 issue.
Office Action issued in related Australian Patent Application No. 2017342462 dated Jul. 20, 2021.
Office Action issued in related Australian Patent Application No. 2017342462 dated Oct. 1, 2021.
Office Action issued in related Chinese Patent Application No. 2017800775257 dated Nov. 14, 2022.
Office Action issued in related Chinese Patent Application No. 2017800775257 dated Nov. 21, 2022.
Office Action issued in related European Patent Application No. 17800964.3 dated May 24, 2019.
Office Action issued in related Israeli Patent Application No. 719562 dated Mar. 15, 2020.
Response filed in related Israeli Patent Application No. 719562 dated Jul. 14, 2020.
List of Citations filed in related Israeli Patent Application No. 719562 dated Jul. 15, 2020.
Office Action issued in related Israeli Patent Application No. 719562 dated Nov. 11, 2021.
Office Action issued in related Israeli Patent Application No. 719562 dated Sep. 21, 2022.
Office Action issued in related Israeli Patent Application No. 719562 dated Oct. 26, 2022.
Response filed in related Japanese Patent Application No. 2019-518975 dated Sep. 28, 2020.
Withdrawal issued in related Japanese Patent Application No. 2019-518975 dated May 10, 2021.
Amendment filed in related Korean Patent Application No. 10-2019-7013370 dated Aug. 3, 2020.
Office Action issued in related Mexican Patent Application No. MX/a/2019/003994 dated Jul. 21, 2022.
Office Action issued in related Singapore Patent Application No. 11201902974P dated Apr. 29, 2021.
Office Action issued in related U.S. Appl. No. 16/341,579 dated Mar. 4, 2022.
Notice of Abandonment issued in related U.S. Appl. No. 16/341,579 dated Oct. 7, 2022.
Amendment filed in related Singapore Patent Application No. 11201706872S dated Feb. 22, 2018.
Response filed in related Singapore Patent Application No. 11201706872S dated Mar. 2, 2018.
Response filed in related Singapore Patent Application No. 11201706872S dated Nov. 30, 2018.
Response filed in related Singapore Patent Application No. 11201706872S dated Apr. 1, 2020.
Office Action issued in related Singapore Patent Application No. 11201706872S dated Jan. 21, 2021.
Office Action issued in related Singapore Patent Application No. 11201706872S dated Jul. 21, 2021.
Amendment filed in related U.S. Appl. No. 15/554,540 dated Aug. 30, 2017.
Office Action issued in related U.S. Appl. No. 15/554,540 dated Mar. 22, 2019.
Response filed in related U.S. Appl. No. 15/554,540 dated Sep. 23, 2019.
Office Action issued in related U.S. Appl. No. 15/554,540 dated Jan. 2, 2020.
Response filed in related U.S. Appl. No. 15/554,540 dated May 4, 2020.
Office Action issued in related U.S. Appl. No. 15/554,540 dated Aug. 11, 2020.
Response filed in related U.S. Appl. No. 15/554,540 dated Oct. 13, 2020.
Notice of Allowance issued in related U.S. Appl. No. 15/554,540 dated Nov. 4, 2020.
Response filed in related U.S. Appl. No. 15/554,540 dated Jan. 12, 2021.
Response filed in related U.S. Appl. No. 15/554,540 dated Feb. 2, 2021.
Amendment filed in related European Patent Application No. 16710891.9 dated May 3, 2018.
Response filed in related European Patent Application No. 16710891.9 dated Dec. 23, 2019.
Amendment filed in related European Patent Application No. 16710891.9 dated Feb. 18, 2020.
Amendment filed in related European Patent Application No. 16710891.9 dated Aug. 10, 2020.
Response filed in related European Patent Application No. 16710891.9 dated Jan. 26, 2021.
Notice of Allowance issued in related European Patent Application No. 16710891.9 dated Oct. 20, 2021.
Notice of Allowance issued in related European Patent Application No. 16710891.9 dated Apr. 7, 2022.
Opposition filed in related European Patent Application No. 16710891.9 dated Jan. 23, 2023.

(56) References Cited

OTHER PUBLICATIONS

Opposition filed in related European Patent Application No. 16710891.9 dated Jan. 27, 2023.
Opposition filed in related European Patent Application No. 16710891.9 dated Feb. 8, 2023.
Opposition filed in related European Patent Application No. 16710891.9 dated Feb. 9, 2023.
Office Action issued in related European Patent Application No. 16710891.9 dated Feb. 17, 2023.
"Clinical Trial NCT01848834, History of Changes for Study: NCT01848834: Study of Pembrolizumab (MK-3475) in Participants with Advanced Solid Tumors (MK-3475-012/KEYNOTE-012)" as published on Jan. 21, 2015.
Eisai Public Relations Department: "Eisai and Merck Enter Collaboration to Explore Novel Combinaion Regimens of Anti-PD-1 Therapy with Multi-targeting RTK Inhibitor and Microtubule Dynamics Inhibitor in Multiple Types of Cancer", Mar. 4, 2015, Tokyo, Japan and Kenilworth, NJ, USA, Retrieved from the Internet: URL: http://www.eisai.com/news/enews201518p.
Highlights of Prescribing Information of HALAVEN (eribulin mesylate), published Nov. 2010.
Highlights of Prescribing Information of KEYTRUDA (pembrolizumab), published Sep. 2014.
WHO Drug Information, vol. 27, No. 2, 2013 (excerpt on lambrolizumab (synonym for pembrolizumab).
Clinical trial NCT02513472: History of Changes for Study: NCT02513472: Study to Evaluation the Efficacy and Safety of Eribulin Mesylate in Combindation with Pembrolizumab in Subjects with Metastatic Triple-Negative Breast Cancer (mTNBC) (study status: Nov. 12, 2015).
Mancini et al., "Review: Standard of care and promising new agents for triple negative metastatic breast cancer," Cancers, 6 (4): 2187-2223 (2014).
Morikawa et al., "Review: Treating Triple-Negative Breast Cancer: Where Are We?" Journal of the National Comprehensive Cancer Network, 13(2), e8-e18 (Feb. 2015).
Brewster et al. "Epidemiology, biology, and treatment of triple-negative breast cancer in women of African ancestry" The Lancet Oncology, 15(13): e625-e634 (2014).
Doherty et al., "Review: Eribulin for the treatment of metastatic breast cancer: an update on its safety and efficacy" International Journal of Women's Health, 7, 47 (Jan. 2015).
Doherty et al., "Eribulin for the treatment of metastatic breast cancer: an update on its safety and efficacy" International Journal of Women's Health, 7, (Abstract) (Jan. 2015).
Marm et al., "Targeted therapies in triple-negative breast cancer" Breast Care, 10(3): 159-166 (Jun. 2015).
Kalimutho, M. et al. "Review: Targeted therapies for triple-negative breast cancer: Combating a stubborn disease," Trends in Pharmacological Sciences, 36(12): 822-846 (Published online Nov. 1, 2015).
McDermott et al. "Review: PD-1 as a potential target in cancer therapy" Cancer Medicine, 662-673 (2013).
Robert et al. "Drug of the year: programmed death-1 receptor/programmed death-1 ligand-1 receptor monoclonal antibodies," European Journal of Cancer, 49(14), 2968-2971 (2013).
Poole, "Pembrolizumab: first global approval" Drugs, 74(16): 1973-1981 (2014).
Dolan et al., "Review: PD-1 pathway inhibitors: changing the landscape of cancer immunotherapy," Cancer Control, 21 (3), 231-237 (2014).
Nanda et al. 2014 San Antonio Breast Cancer Symposium; S1-09; A phase lb study of pembrolizumab (MK-3475) in patients with advanced triple-negative breast cancer (02 only abstract).
Azvolinsky, "Immunotherapy Yields Response in Triple-Negative Breast Cancer," cancernetwork (Dec. 2014).
Azvolinsky, "Top 8 Highlights From SABCS 2014" cancernetwork (Dec. 2014).
"Pembrolizumab Shows Potential in Breast Cancer" Cancer Discovery 100-101 (Feb. 2015).
Ahmed "Report from the 37th San Antonio Breast Cancer Symposium, Dec. 9-13, 2014, Texas, USA" Ecancermedicalscience, 4;9:508 (Feb. 2015).
Administrative Appeal Against Rejection filed in Argentine Patent Application No. P100103420, dated Jan. 24, 2022, 19 pages (with English Translation).
International Search Report in International Patent Application No. PCT/JP2020/028663, dated Sep. 24, 2020, 20 pages (with English Translation).
Etters Patent for Iranian Patent No. 83009, granted on Jun. 3, 2014, 2 pages (with English Translation).
Etters Patent for Thai Patent No. 85826, granted on Dec. 13, 2021, 2 pages (with English Translation).
Mano, "A separate assay of released and liposomal encapsulated eribulin in dog plasma by liquid chromatography with tandem mass spectrometry for its application to a pharmacokinetic study," Journal of Separation Science, 2022, 10 bages.
Notice of Allowance in United States U.S. Appl. No. 14/061,426, dated Jan. 14, 2022, 21 pages.
Notice of Allowance in United States U.S. Appl. No. 14/061,426, dated Mar. 31, 2022, 11 pages.
Notice of Allowance in United States U.S. Appl. No. 14/061,426, dated Aug. 4, 2022, 11 pages.
Notice of Allowance in United States U.S. Appl. No. 14/061,426, dated Dec. 19, 2022, 12 pages.
Office Action in Argentine Patent Application No. P100103420, dated Jun. 9, 2021, 14 pages (with English Translation).
Office Action in Jordanian Patent Application No. 0381/2020, dated Apr. 23, 2018, 2 pages (with English Translation).
Request for Continued Examination in United States U.S. Appl. No. 17/067,302, dated Apr. 12, 2021, 1 page.
Response filed in Argentine Patent Application No. P100103420, dated Aug. 4, 2020, 53 pages (with English Translation).
Response filed in Argentine Patent Application No. P100103420, dated May 13, 2021, 23 pages (with English Translation).
Submission Document in U.S. Patent Application No. 17/563, 162, dated May 31, 2022, 4 pages.
Substantive Examination in Argentine Patent Application No. P100103420, dated Nov. 6, 2019, 18 pages (with English Translation).
Amendment filed in related Australian Patent Application No. 2016226157 dated Aug. 11, 2020.
Office Action issued in related Australian Patent Application No. 2016226157 dated Jan. 29, 2021.
Response filed in related Australian Patent Application No. 2016226157 dated Nov. 30, 2021.
Office Action issued in related Australian Patent Application No. 2016226157 dated Dec. 15, 2021.
Response filed in related Australian Patent Application No. 2016226157 dated Jan. 5, 2022.
Notice of Allowance issued in related Australian Patent Application No. 2016226157 dated Jan. 18, 2022.
Office Action issued in related Brazilian Patent Application No. 112017018872-4 dated Sep. 21, 2021.
Response filed in related Brazilian Patent Application No. 112017018872-4 dated Dec. 16, 2021.
Amendment filed in related Canadian Patent Application No. 2978311 dated Mar. 2, 2021.
Amendment filed in related Canadian Patent Application No. 2978311 dated Apr. 21, 2022.
Office Action issued in related Canadian Patent Application No. 2978311 dated Jun. 3, 2022.
Response filed in related Chinese Patent Application No. 201680025588.3 dated Sep. 22, 2020.
Response filed in related Chinese Patent Application No. 201680025588.3 dated Dec. 15, 2020.
Notice of Allowance issued in related Chinese Patent Application No. 201680025588.3 dated Dec. 31, 2020.
Office Action issued in related Israeli Patent Application No. 254133 dated Jan. 20, 2019.
Response filed in related Israeli Patent Application No. 254133 dated May 20, 2019.

(56) References Cited

OTHER PUBLICATIONS

List of Citations filed in related Israeli Patent Application No. 254133 dated Nov. 17, 2019.
List of Citations filed in related Israeli Patent Application No. 254133 dated Feb. 2, 2020.
Response filed in related Israeli Patent Application No. 254133 dated Mar. 11, 2021.
Notice of Allowance issued in related Israeli Patent Application No. 254133 dated Jun. 3, 2021.
List of Citations filed in related Israeli Patent Application No. 254133 dated Aug. 11, 2021.
List of Citations filed in related Israeli Patent Application No. 254133 dated Aug. 18, 2021.
Notice of Allowance issued in related Israeli Patent Application No. 254133 dated Sep. 19, 2021.
Response filed in related Indian Patent Application No. 201747034283 dated Nov. 24, 2020.
Response filed in related Indian Patent Application No. 201747034283 dated Nov. 27, 2020.
Response filed in related Indian Patent Application No. 201747034283 dated Mar. 2, 2021.
Office Action issued in related Indian Patent Application No. 201747034283 dated Mar. 30, 2021.
Office Action issued in related Indian Patent Application No. 201747034283 dated Apr. 27, 2021.
Response filed in related Indian Patent Application No. 201747034283 dated Apr. 27, 2021.
Amendment filed in related Japanese Patent Application No. 2017-546075 dated Mar. 4, 2019.
Response filed in related Japanese Patent Application No. 2017-546075 dated Apr. 1, 2020.
Response filed in related Japanese Patent Application No. 2017-546075 dated Oct. 15, 2020.
Office Action issued in related Japanese Patent Application No. 2017-546075 dated Mar. 23, 2021.
Response filed in related Japanese Patent Application No. 2017-546075 dated May 21, 2021.
Notice of Allowance issued in related Japanese Patent Application No. 2017-546075 dated Aug. 31, 2021.
Amendment filed in related Korean Patent Application No. 10-2017-7027617 dated Feb. 23, 2021.
Office Action issued in related Korean Patent Application No. 10-2017-7027617 dated Jan. 9, 2023.
Response filed in related Mexican Patent Application No. MX/a/2017/011206 dated Jan. 22, 2021.
Office Action issued in related Mexican Patent Application No. MX/a/2017/011206 dated Mar. 12, 2021.
Response filed in related Mexican Patent Application No. MX/a/2017/011206 dated Jul. 15, 2021.
Office Action issued in related Mexican Patent Application No. MX/a/2017/011206 dated Jul. 23, 2021.
Response filed in related Mexican Patent Application No. MX/a/2017/011206 dated Jul. 27, 2021.
Office Action issued in related Mexican Patent Application No. MX/a/2017/011206 dated Jul. 30, 2021.
Response filed in related Mexican Patent Application No. MX/a/2017/011206 dated Sep. 28, 2021.
Notice of Allowance issued in related Mexican Patent Application No. MX/a/2017/011206 dated Sep. 28, 2021.
Response filed in related Russian Patent Application No. 2017132877/04 dated Nov. 28, 2019.
Office Action issued in related Russian Patent Application No. 2017132877/04 dated Jan. 27, 2020.
Response filed in related Russian Patent Application No. 2017132877/04 dated Jul. 27, 2020.
Notice of Allowance issued in related U.S. Appl. No. 16/090,360 dated Mar. 22, 2023.
Antitumor activity of liposomal formulation of eribulin combined with anti-human PD-1 antibody using hPBMC-humanized mouse models, "Niwa et al.", American Association for Cancer Research Annual Meeting 2023, abstract, Mar. 31, 2023.
Notice of Allowance issued in related U.S. Appl. No. 16/090,360 dated Apr. 19, 2023.
Office Action in Malaysian Patent Application No. PI2011004382, dated Sep. 30, 2016, 2 pages.
Office Action in Mexican Patent Application No. MX/a/2011/009632, dated Apr. 22, 2013, 12 pages (with English Translation).
Office Action in Mexican Patent Application No. MX/a/2011/009632, dated Aug. 7, 2012, 6 pages (with English Translation).
Office Action in Mexican Patent Application No. MX/a/2011/009632, dated Jan. 17, 2014, 6 pages (with English Translation).
Office Action in New Zealand Patent Application No. 595212, dated Aug. 14, 2012, 1 page.
Office Action in Peruvian Patent Application No. 001735-2011/DIN, dated Jan. 9, 2014, 2 pages (with English Translation).
Office Action in Peruvian Patent Application No. 001735-2011/DIN, dated Nov. 23, 2012, 15 pages (with English Translation).
Office Action in Peruvian Patent Application No. 001735-2011/DIN, dated Sep. 29, 2014, 7 pages (with English Translation).
Office Action in Philippine Patent Application No. 1/2011/501838, dated Jun. 4, 2015, 1 page.
Office Action in Philippine Patent Application No. 1/2011-501838, dated Sep. 17, 2014, 2 pages.
Office Action in Philippine Patent Application No. 1-2011-501838, dated Aug. 8, 2013, 1 page.
Office Action in Russian Patent Application No. 2017132877, dated Aug. 29, 2019, 12 pages (with English Translation).
Office Action in Russian Patent Application No. 2017132877, dated Jan. 27, 2020, 8 pages (with English Translation).
Office Action in Russian Patent Application. No. 201 1 139715/20, dated Nov. 28, 2011, (with partial English Translation), with Applicant Response filed on Jan. 30, 2012, 4 page.
Office Action in Taiwanese Patent Application No. 099109838, dated Jun. 22, 2012, 9 pages (with English Translation).
Office Action in U.S. Appl. No. 13/260,864, dated Feb. 3, 2017, 11 pages.
Office Action in U.S. Appl. No. 13/260,864, dated Jul. 13, 2015, 11 pages.
Office Action in U.S. Appl. No. 13/260,864, dated Jun. 27, 2016, 10 pages.
Office Action in U.S. Appl. No. 13/260,864, dated Mar. 10, 2014, 8 pages.
Office Action in U.S. Appl. No. 13/260,864, dated Sep. 26, 2014, 15 pages.
Office Action in U.S. Appl. No. 13/260,872, dated Apr. 24, 2013, 24 pages.
Office Action in U.S. Appl. No. 13/260,872, dated Aug. 1, 2012, 17 pages.
Office Action in U.S. Appl. No. 14/061,426 dated Oct. 30, 2017, 17 pages.
Office Action in U.S. Appl. No. 14/061,426, dated May 30, 2019, 17 pages.
Office Action in U.S. Appl. No. 14/061,426, dated May 31, 2017, 39 pages.
Office Action in U.S. Appl. No. 14/061,426, dated Nov. 19, 2018, 23 pages.
Office Action in U.S. Appl. No. 14/061,426, dated Sep. 24, 2015, 17 pages.
Office Action in U.S. Appl. No. 14/061,426, dated Mar. 18, 2016, 24 pages.
Office Action in U.S. Appl. No. 15/554,540, dated Jan. 2, 2020, 15 pages.
Office Action in U.S. Appl. No. 15/554,540, dated Mar. 22, 2020, 27 pages.
Office Action in U.S. Appl. No. 16/835,719, dated Jun. 29. 2020, 15 pages.
Office Action in Vietnamese Patent Application No. 1-2011-02950, dated Aug. 16, 2013, 3 pages (with English Translation).
Office Action in Vietnamese Patent Application No. 1-2011-02950, dated Mar. 31, 2016, 3 pages (with English Translation).
Official Decision in Egyptian Patent Application No. PCT1637/2011, dated Jan. 3, 2017, 8 pages (with English Translation).

(56) References Cited

OTHER PUBLICATIONS

Official Notification in Peruvian Patent Application No. 001735-2011/DIN, dated Jul. 16, 2015, 28 pages (with English Translation).
Official Notification in Vietnamese Patent Application No. 1-2011-02950, dated Jan. 24, 2017, 2 pages (with English Translation).
Ohigashi et al., "Clinical Significance of Programmed Death- 1 Ligand-I and Programmed Death-I Ligand-2 Expression in Human Esophageal Cancer," Clin. Cancer Res., 2005, 11(8):2947-2953.
Okouneva et al., "Inhibition of centromere dynamics by eribulin (E7389) during mitotic metaphase," Molecular Cancer Therapeutics, 2008, 7(7):2003-2011.
Opposition in Colombian Patent Application No. 11-130828, dated Apr. 30, 2012, 14 pages (with English Translation).
Opposition in Colombian Patent Application No. 11-130828, dated Jul. 25, 2012, 14 pages (with English Translation).
Opposition in Peruvian Patent Application No. 001735-2011/DIN, dated Jan. 20, 2015, 25 pages (with English Translation).
Opposition in Peruvian Patent Application No. 001798-2015, dated Jan. 25, 2016, 18 pages (with English Translation).
Pardoll, "The blockade of immune checkpoints in cancer immunotherapy," Nature Reviews Cancer, 2012, 12:252-264.
Peleg-Shulman et al., "Characterization of sterically stabilized cisplatin liposomes by nuclear magnetic resonance," Biochimica et Biophysica, 2001, 1510(1-2): 278-291.
Petition in Japanese Patent Application No. 2014-092382, dated Dec. 26, 2014, 9 pages (with English Translation).
Piel et al., "Betamethasone-in-cyclodextrin-in-liposome: The effect of cyclodextrins on encapsulation efficiency and release kinetics," International Journal of Pharmaceutics, 2006, 312:75-82.
Poujol et al., "Stability of the ready-to use solutions of eribulin for intravenous infusion," Annales pharmaceutiques Francaises, 2012, 70(5):249-255.
Preliminary Amendment filed in Japanese Patent Application No. 2014-092382 dated May 28, 2014, 4 pages (with English Translation).
Preliminary Conclusion in Ukrainian Patent Application No. a201 1 1 1426, dated Apr. 8, 2013, 8 pages (with English Translation).
Rajora et al., "Impact of the Enhanced Permeability and Retention (EPR) Effect and Cathepsins Levels on the Activity of Polymer-Drug Conjugates," Polymers, 2014, 6:2186-2220.
Nippon Kayaku Co., Ltd., "Rozeus® Intravenous Solution 10 mg—Rozeus® Intravenous Solution 40 mg—Vinorelbine Ditartrate Intravenous Solution," Package Insert, revised Nov. 2009, 5 pages (with Partial Translation).
Nomi et al., "Clinical Significance and Therapeutic Potential of the Programmed Death-I Ligand/Programmed Death-I Pathway in Human Pancreatic Cancer," Clin. Cancer Res., 2007, 13(7):2151-2157.
Notice of Allowance in Australian Patent Application No. 2014200717, dated Feb. 13, 2016, 2 pages.
Notice of Allowance in Canadian Patent Application No. 2756811, dated Feb. 10, 2014, 1 pag.
Notice of Allowance in Chilean Patent Application No. 2444-2011, dated Jul. 3, 2018, 8 pages (with English Translation).
Notice of Allowance in Chinese Patent Application No. 201080014698.2, dated Aug. 6, 2014, 4 pages (with English Translation).
Notice of Allowance in Colombian Patent Application No. 11-130828, dated Jan. 21, 2014, 12 pages (with English Translation).
Notice of Allowance in Indonesian Patent Application No. W00201103470 dated Apr. 20, 2017, 4 pages (with English Translation.
Notice of Allowance in Israeli Patent Application No. 215059, dated Nov. 25, 2015, 3 pages (with English Translation).
Notice of Allowance in Korean Patent Application No. 10-2011-7022860, dated Jan. 9, 2015, 4 pages (with English Translation).
Notice of Allowance in Mexican Patent Application No. MX/A/2011/009632, dated Oct. 14, 2014, 2 pages (with English Translation).
Notice of Allowance in New Zealand Patent Application No. 595212, dated Feb. 25, 2014, 1 page.
Notice of Allowance in Taiwanese Patent Application No. 099109838, dated Jan. 23, 2013, 5 pages (with English Translation).
Notice of Allowance in Ukrainian Patent Application No. a201111426, dated Jul. 23, 2013, 7 pages (with English Translation).
Notice of Final Rejection in Korean Patent Application No. 10-2011-7022860, dated Sep. 23, 2014, 5 pages (with English Translation).
Notice of Panel Decision in U.S. Appl. No. 14/061,426, dated Oct. 1, 2019, 2 pages.
Notice of Reason for Rejection in Japanese Patent Application No. 2011-507239, dated Feb. 27, 2014, 6 pages (with English Translation).
Notice of Reason for Rejection in Japanese Patent Application No. 2011-507240, dated Feb. 6, 2014, 7 pages (with English Translation).
Notice of Reason for Rejection in Japanese Patent Application No. 2014-092382, dated Jan. 28, 2015, 5 pages (with English Translation).
Notification of the Brazilian Patent and Trademark Office and Documents fonvarded by ANVISA (Brazilian Health Surveillance Agency) for Brazilian Patent Application No. PI1014527-3, including transmittal letter (dated Jul. 31, 2019); Technical Written Opinion of Consent of a Patent Application of Pharmaceutical products and Processes (Jul. 18, 2019), supporting documents (Jul. 24, 2019), and "Documents Fonvarded bv ANVIA" (Sep. 5, 2019).
Observation Notification in Peruvian Patent Application No. 001798-2015, dated Feb. 12, 2020, 11 pages (with English Translation).
Observation Notification in Peruvian Patent Application No. 001798-2015, dated Oct. 16, 2019, 15 pages (with English Translation).
Office Action in Australian Patent Application No. 2010232347, dated May 11, 2012, 2 pages.
Office Action in Australian Patent Application No. 2014200717, dated Aug. 14, 2015, 2 pages.
Office Action in Brazilian Patent Application No. PI10145273, dated Mar. 30, 2020, 24 pages (with English Translation).
Office Action in Canadian Patent Application No. 2756811, dated Dec. 19, 2012, 4 page.
Office Action in Canadian Patent Application No. 2756811, dated Jul. 17, 2013, 2 pages.
Office Action in Chilean Patent Application No. 2444-2011, dated Jan. 16, 2014, 6 pages (with English Translation).
Office Action in Chilean Patent Application No. 2444-2011, dated Jan. 21, 2015, 20 pages (with English Translation).
Office Action in Chilean Patent Application No. 2444-2011, dated Jul. 11, 2013, 19 pages (with English Translation).
Office Action in Chilean Patent Application No. 2444-2011, dated Dec. 18, 2015, 15 pages (with English Translation).
Office Action in Chinese Patent Application No. 201080014698.2 dated Oct. 24, 2012, 14 pages (with English Translation).
Office Action in Chinese Patent Application No. 201080014698.2, dated Aug. 8, 2013, 12 pages (with English Translation).
Office Action in Chinese Patent Application No. 201080014698.2, dated Mar. 28, 2014, 6 pages (with English Translation).
Office Action in Chinese Patent Application No. 201680025588.3, dated Jan. 6, 2020, 28 pages (with English Translation).
Office Action in Colombian Patent Application No. 11-130828, dated Aug. 8, 2013, 30 pages (with English Translation).
Office Action in Egyptian Patent Application No. PCT1637/2011, dated Jan. 14, 2016, 10 pages (with English Translation).
Office Action in European Patent Application No. 10758754.5, dated Jan. 24, 2014, 7 page.
Office Action in European Patent Application No. 10758755.2, dated Jan. 24, 2014, 4 pages.
Office Action in European Patent Application No. 16710891.9, dated Aug. 13, 2019, 6 pages.
Office Action in European Patent Application No. 16710891.9, dated Mar. 31, 2020, 6 pages.
Office Action in Indian Patent Application No. 201747034283, dated Feb. 28, 2020, 7 pages (with English Translation).
Office Action in Indian Patent Application No. 6850DELNP201 I, dated Nov. 10, 2016, 9 pages.
Office Action in Indonesian Patent Application No. W0020113470, dated Nov. 29, 2013, 7 pages (with English Translation).
Office Action in Israeli Patent Application No. 215059, dated Aug. 4, 2014, 3 pages (with English Translation).

(56) References Cited

OTHER PUBLICATIONS

Office Action in Japanese Patent Application No. 2017-546075, dated Jan. 7, 2020, 6 pages (with English Translation).
Office Action in Korean Patent Application No. 10-2011-7022860, dated Jul. 22, 2013, 20 pages (with English Translation).
Office Action inKorean PatentApplication No. 10-2011-7022860, dated May 20, 2014, 11 pages (with English Translation).
Office Action in Korean Patent Application No. 10-2011-7022860, Notice of Preliminary Rejection, dated Dec. 28, 2012, 7 pages (with English Translation).
Office Action in Malaysian Patent Application No. PI2011004382, dated Apr. 15, 2013, 3 pages.
ClinicalTrials.gov [online], "A Study ofE7389 Liposomal Formulation (E7389-LF) Plus Nivolumab in Participants with Solid Tumor, History of Changes for Study: NCTO4078295," Sep. 2019, retrieved from: URL<https://clinicaltrials.gov/ct2/history/NCTO4078295?V_I=View#StudyPageTop, Sep. 2, 2019>, 4 pages.
Eisai Co., Ltd., News Release No. 20-54, "Eisai to present abstracts on oncology products and pipeline at ESMO Virtual Congress 2020," dated Sep. 11, 2020, 3 pages.
Eisai Co., Ltd., News Release No. 20-56, "Eisai presents latest data of phase I clinical trial on liposomal formulation of anti-cancer agent Halaven® (Eribulin) at ESMO Virtual Congress 2020," dated Sep. 18, 2020, 3 pages.
Iwasa et al., "Effect of infusion rate, premedication, and prophylactic peg-filgrastim treatment on the safety of the liposomal formulation of eribulin (E7389-LF): Results from the expansion part of a phase 1 study," Abstract 583P, Sep. 17, 2020, the European Society for Medical Oncology (ESMO) Virtual Congress, Sep. 19-21, 2020, Annals of Oncology (2020) 31 (suppl_4): S462-S504, 10.1016/annonc/annonc271, NPL277, 8 pages.
Iwasa et al., "Effect of infusion rate, premedication, and prophylactic peg-filgrastim treatment on the safety of the liposomal formulation of eribulin (E7389-LF): Results from the expansion part of a phase 1 study," E-poster for Abstract 583P, presented at the European Society for Medical Oncology (ESMO) Virtual Congress, Sep. 19-21, 2020, Annals of Oncology (2020) 31 (suppl_ 4 ): S462-S504, 10.1016/annonc/annonc271, 1 page.
Letters Patent for Patent No. 10271 in Algerian Patent Application No. II0640, dated Sep. 13, 2020, 4 pages (with English Translation).
Notice of Abandonment in U.S. Appl. No. 13/260,872, dated Dec. 3, 2013, 2 pages.
Notice of Allowance in Brazilian Patent Application No. PI10145273, dated Oct. 20, 2020, 2 pages (with English Translation).
Office Action in Brazilian Patent Application No. PI10145273, dated Jul. 14, 2020, 9 pages (with English Translation).
Office Action in Chinese Patent Application No. 201680025588.3, dated Jul. 7, 2020, 29 pages (with English Translation).
Office Action in Japanese Patent Application No. 2017-546075, dated Jul. 21, 2020, 6 page (with English Translation).
Office Action in U.S. Appl. No. 14/061,426, dated Sep. 1, 2020, 21 pages.
Patent Certificate for Bruneian Patent No. RE-R-2017-0029, granted on Jul. 4, 2017, 1 page.
Patent Certificate for Japanese Patent No. 5770336, granted on Jul. 3, 2015, 4 pages (with English Translation).
PCT International Search Report in International Patent Application No. PCT/JP2020/028663, dated Sep. 24, 2020, 20 pages (with English Translation).
Request for Examination in Brazilian Patent Application No. PI10145273, dated Dec. 27, 2011, 6 pages (with English Translation).
Request for Examination in Ukrainian Patent Application No. a201 1 1 1426, dated Feb. 1, 2013, 2 pages (with English Translation).
Response filed in Brazilian Patent Application No. PI10145273, dated Jul. 2, 2020, to the Office Action issued on Mar. 30, 2020, 80 pages (with English Translation).
Response filed in Brazilian Patent Application No. PI10145273, dated Oct. 6, 2020, to the Office Action issued on Jul. 14, 2020, 20 pages (with English Translation).
Response filed in Peruvian Patent Application No. 001798-2015, dated Jul. 23, 2020, 15 pages (with English Translation).
Response filed in United States U.S. Appl. No. 16/835,719, dated Sep. 29, 2020, 10 pages.
Tamura et al., "Phase 1 study of the liposomal formulation of eribulin (E7389-LF): Results from the HER2-negative breast cancer expansion part," Eposter for Abstract 346P, presented at the European Society for Medical Oncology (ESMO) Virtual Congress, Sep. 19-21, 2020, Annals of Oncology (2020) 31(suppl 4):S348-S395, 10.1016/annonc/annonc268, 1 page.
Tamura et al., "Phase 1 study of the liposomal formulation of eribulin (E7389-LF): Results from the HER2-negative breast cancer expansion," Abstract 346P, dated Sep. 17, 2020, the European Society for Medical Oncology (ESMO) Virtual Congress, Sep. 19-21, 2020, Annals of Oncology (2020) 31(suppl 4):S348-S395, 10.1016/annonc/annonc268, 7 pages.
Tolaney et al., "Abstract PD6-13: Phase lb/2 study to evaluate eribulin mesylate in combination with pembrolizumab in patients with metastatic triple-negative breast cancer," Cancer Research, Feb. 2018, vol. 78, 4 pages.
Communication pursuant to Article 94(3) EPC in European Patent Application No. 16710891.9, dated Nov. 16, 2020, 24 pages.
Letters Patent for the Brazilian Patent No. PI 1014527-3, granted on Nov. 24, 2020, 70 pages (with English Translation).
Notice of Allowance in U.S. Appl. No. 15/554,540, dated Nov. 4, 2020, 7 pages.
Notice of Intention to Refuse Patent Application in Singaporean Patent Application No. 1120 1 706872S, dated Nov. 19, 2020, 11 pages.
Office Action in Mexican Patent Application No. MX/a/2017/011206, dated Nov. 24, 2020, 8 pages (with Partial Translation).
Office Action in U.S. Appl. No. 15/554,540, dated Aug. 11, 2020, 7 pages.
Response filed in U.S. Appl. No. 15/554,540, dated May 4, 2020, 23 pages.
Response filed in U.S. Appl. No. 15/554,540, dated Oct. 13, 2020, 7 pages.
Response filed in U.S. Appl. No. 15/554,540, dated Sep. 23, 2019, 38 pages.
Response filed in U.S. Appl. No. 16/835,719, dated Nov. 2, 2020, 7 pages.
Schmidt et al., "Assessment of Clinical Activity of PD-1 Checkpoint Inhibitor Combination Therapies Reported in Clinical Trials," JAMA Network Open. Feb. 2020, 3(2):el 920833.
Extended European Search Report issued in counterpart European Patent Application No. 20847524.4 dated Jun. 19, 2023.
Azuma et al., "The Small Cell Lung Cancer Cohort of a Phase 2 Trial of E7389-LF (Liposomal Formulation of Eribulin) + NivolumabE7389-Nivolumab", Poster Presentation at the American Society for Clinical Oncology Symposium; Jun. 2-6; Chicago, IL, USA (2023).
Azuma et al., "Phase 2 small cell lung cancer (SCLC) cohort of a phase 1b/2 trial of a liposomal formulation of eribulin in combination with nivolumab.", Abstract No. 8593, Meeting Abstract I, 2023 ASCO Annual Meeting I. Published online May 31, 2023.
Ghebeh et al. "FOXP3+ Tregs and B7-HI+fPD-I + T lymphocytes co-infiltrate the tumor tissues of high-risk breast cancer patients: Implication for immunotherapy," BMC Cancer, 2008, 8:57.
Ghebeh et al., "The B7-HI (Pd-Li) T Lymphocyte-Inhibitory Molecule is Expressed in Breast Cancer Patients with Infiltrating Ductal Carcinoma: Correlation with Important High-Risk Prognostic Factors," Neoplasia, 2006, 8(3):190-198.
Golub et al., "Molecular Classification of Cancer: Class Discovery and Class Prediction by Gene Expression Monitoring," Science, 1999, 286:531-537.
Hagiwara et al., "Preparation and pharmaceutical evaluation of liposomes entrapping salicylic acid/y-cyclodextrin conjugate," Chem. Phann. Bull., 2006, 54(1):26-32.
Hamanishi et al., "Programmed cell death 1 ligand 1 and tumor-infiltrating CDS+ T lymphocytes are prognostic factors of human ovarian cancer," PNAS, 2007, 104(9):3360-3365.

(56) References Cited

OTHER PUBLICATIONS

Haran et al., "Transmembrane ammonium sulfate gradients in liposomes produce efficient and stable entrapment of amphipathic weak bases," Biochimica et Biophysica Acta. Biomembranes, 1993, 1151(2):201-215.
Hart et al., "Acid-catalyzed reactions of homohalichondrin B, a marine sponge-derived antitumor polyether macrolide," The Journal of Organic Chemistry, 1996, 61(8):2888-2890.
Hearing Notice in Indian Patent Application No. 6850/DELNP/201 I, dated Aug. 17, 2017, 3 pages.
Hino et al., "Tumor Cell Expression of Programmed Cell Death-I Ligand 1 Is a Prognostic Factor for Malignant Melanoma," Cancer, 2010, 116(7):1757-1766.
Inman et al., "PD-LI (B7-HI) Expression by Urothelial Carcinoma of the Bladder and ECG-Induced Granulomata," Cancer, 2007, 109(8): 1499-1505.
International Preliminary Report on Patentability in International Application No. PCT/US2016/020734, dated Sep. 5, 2017, 9 pages.
International Preliminary Report on Patentability in International Application No. PCT/US2017/056552, dated Apr. 25, 2019, 8 pages.
International Preliminary Report on Patentability in International Patent Application No. PCT/JP2017/016633, dated Oct. 30, 2018, 22 pages.
International Preliminary Report on Patentability in International Patent Application No. PCT/JP2010/055769, dated Oct. 4, 2011, 11 pages.
International Preliminary Report on Patentability in International Patent Application No. PCT/JP2010/055770, dated Nov. 15, 2011, 9 pages.
International Search Report and Written Opinion in International Patent Application No. PCT/US2017/056552, dated Jan. 2, 2018, 11 pages.
International Search Report in International Application No. PCT/JP2010/055770, dated Jun. 1, 2010, 2 pages.
International Search Report in International Application No. PCT/US2016/020734, dated Apr. 28, 2016, 7 pages.
International Search Report in International Patent Application No. PCT/JP2010/0055769, dated Jun. 8, 2010, 5 pages.
International Search Report in International Patent Application No. PCT /JP2017/01663 3, dated Jun. 6, 2017, 6 pages.
International Search Report in International Patent Application No. PCT/JP2018/020456, dated Aug. 28, 2018, 5 pages.
Intimation Notification in Indian Patent Application No. 6850/DELNP/201 I, dated Aug. 23, 2018, 1 page.
Ishida et al., "Targeted delivery and triggered release of liposomal doxorubicin enhances cytotoxicity against human B lymphoma cell," Biochimica et Biophysica Acta, 2001, 1515: 144-158.
Iupac Goldbook, "Onium Compunds," Entry, [Retrieved on Mar. 9, 2016], retrieved from: URL<http://goldbook.iupac.org/004291.html>, 2.
Jordan et al., "The primary antimitotic mechanism of action of the synthetic halichondrin E7389 is suppression of microtubule growth," Molecular Cancer Therapeutics, 2005, 4(7): 1086-1095.
Kazmi et al., "Real-world I-year survival analysis of patients with metastatic breast cancer with liver or lung visceral metastasis treated with eribulin, gemcitabine," Poster Display, Abstract No. 366P, displayed Sep. 29, 2019, European Society for Medical Oncology (ESMO) 2019 Congress, Barcelona, Spain, 1 page.
Kikuchi, et al. "Liposome I—Method of Preparing and Testing," Cell Engineering, 1983, 2(9): 1136-1149.
Kim et al., "Multivescular liposomes containing cytarabine entrapped in the presence of hydrochloric acid for intracavitary chemotherapy," Cancer Treatment Reports, 1987, 71(7-8):705-711.
Kim et al., "Preparation ofmultivesicular liposomes," Biochimica et Biophysica Acta, 1983, 728:339-348.
Knollman et al., "Muscle-invasive urothelial bladder cancer: an update on systemic therapy," Therapeutic Advances In Urology, 2015, 7(6):312-330.
Kuznetsov et al., "Antiproliferative effects of halichondrin B analog eribulin mesylate (E7389) against paclitaxel-resistant human cancer cells in vitro," AACR-NCI-EORTC International Conference: Molecular Targets and Cancer Therapeutics. Abstract C58. Oct. 2007, 2 pages.
Lasic et al., "Gelation ofliposome interior; A novel method for drug encapsulation," FEBS Lett., 1992, 312(2-3):255-258.
Lasic et al., "Transmembrane gradient driven phase transitions within vesicles: lessons for drug delivery," Biochimica et Biophysica Acta., 1995, 1239(2):145-156.
Liposomes, ed. Fude, CUI, Fifth Edition, People's Press of Hygiene, Mar. 2004, P386-394 (English explanation on Chinese Office Action in CN Appln. No. 201080014698.2 dated Oct. 24, 2012), 8 pages.
Loftsson T et al.: "Solubilization and Stabilization of Drugs Through Cyclodextrin Complexation", Acta Pharmaceutica Nordica, 1991, 3(4):215-217.
Maeda, "EPR Effect," Kobunshi, 2000, 49(3):129.
Maestrelli et al., "Effect of preparation technique on the properties of liposomes encapsulating ketoprofen-cyclodextrin complexes aimed for transdermal delivery," International Journal of Pharmaceutics, 2006, 312:53-60.
Matsumura et al., "A new concept for macromolecular therapeutics in cancer chemotherapy: mechanism of tumoritropic accumulation of proteins and the anti tumor agent smancs," Cancer Research, 1986, 46:6387-6392.
Maurer-Spurej et al., "Factors influencing uptake and retention of amino-containing drugs in large unilamellar vesicles exhibiting transmembrane pH gradients," Biochimica et Biophysica Acta, 1999. 1416:1-10.
Mayer et al., "Uptake of adriamycin into large unilamellar vesicles in response to a pH gradient," Biochimica et Biophysica Acta, 1986, 857:123-126.
Memorandum in Response to Official Action in Israeli Patent Application No. 215059, dated Dec. 2, 2014, 58 pages.
Merck Sharp & Dohme Corp., "Highlights of Prescribing Information—KEYTRUDA® (pembrolizumab)," Label, Suppl. 8, revised Oct. 2016, FDA Ref. ID: 4003165, retrieved from: URL<https://www.accessdata.fda.gov/dmgsatfda_docs/label/2016/I 25514s008s012lbl.pdf>, 29 pages.
Merck Sharp & Dohme Corp., "Highlights of Prescribing Information—KEYTRUDA® (pembrolizumab)," Label, Suppl. 9, revised Aug. 2016, FDA Ref. ID: 3968676, retrieved from: URL<https://www.accessdata.fda.gov/dmgsatfda docs/label/2016/125514s009lbl.pdf>, 26 pages.
Nakanishi et al., "Overexpression ofB7-HI (PD-LI) significantly associates with tumor grade and postoperative prognosis in human urothelial cancers," Cancer Immunol. Immunother., 2007, 56:1173-1182.
Nanda et al., "Pembrolizumab in Patients With Advanced Triple-Negative Breast Cancer: Phase Ib KeyNote-012 Study," Journal of Clinical Oncology, 2016, 34(21):2460-2467.
Nanda, "Pembrolizumab Shows Potential in Breast Cancer," Cancer Discovery, 2015, 5(2): 100-101.
Narayan et al. "Novel second generation analogs of eribulin. Part III: blood-brain barrier permeability and in vivo activity in a brain tumor model," Bioorganic & Medicinal Chemistry Letters, 2011, 21(6):1639-1643.
Nippon Kayaku Co., Ltd., "Adriacin® for injection 10—Adriacin® for injection 50," Package Insert, revised Aug. 2011, 6 pages.
Nippon Kayaku Co., Ltd., "Exal® for injection 10 mg—Japanese Pharmacopeia (JP) Vinblastine Sulfate for Injection," Package Insert, revised Jul. 2011, 7 pages (with Partial Translation).
Nippon Kayaku Co., Ltd., "Oncovin® for injection 1 mg—Vincristine Sulfate Preparation," Package Insert, revised Aug. 2009, 7 pages (with Partial Translation).
[No Author], "Ammonium Cations," The Illustrated Glossary of Organic Chemistry, [Retrieved on Mar. 9, 2016], retrieved from: URL<http://www.chem.ucla.edu/harding/IGOC/ A/ammonium cation.html>, 1 page.
[No Author], "Halaven Intravenour Injection 1mg," Package Insert for Halaven, Eisai, Ltd., Jul. 2011, 6 pages (with partial English Translation).

(56) References Cited

OTHER PUBLICATIONS

[No Author], "Novantron Infection 10mg, 20mg," Package Insert, ASKA Pharmaceutical Co., Ltd., Nov. 2011, 6 pages (with partial English Translation).

[No Author], WHO Drug Information, 2013, vol. 27, No. 1, pp. 68-69.

[No Author], WHO Drug Information, 2013, vol. 27, No. 2, pp. 161-162.

Adams et al., "Phase 2 study of pembrolizumab (pembro) monotherapy for previously treated metastatic triple-negative breast cancer (mTNBC): KeyNote-086 cohort A," Journal of Clinical Oncology, 2017, 35(15 sunnl):1008.

Adams et al., "Phase 2 study of pembrolizumab as first-line therapy for PD-LI -positive metastatic triple-negative breast cancer (mTNBC): Preliminary data from KeyNote-086 cohort B," Journal of Clinical Oncology, 2017, 35(15 suppl):1088.

Ahmadzadeh et al., "Tumor antigen-specific CDS T cells infiltrating the tumor express high levels of PD-1 and are functionally impaired," Blood, 2009, 114(8):1537-1544.

Applicant Observation filed in Chinese Patent Application No. 201080014698.2, dated Apr. 2, 2013 to the first Chinese Office Action dated Oct. 24, 2012, 48 pages (with English Translation).

Arima et al., "Enhancement of antitumor effect of doxorubicin by its complexation with y-cvclodextrin in pegylated liposomes," Journal of Drug Targeting, 2006, 14(4):225-232.

Asano et al., "Broad-spectrum Preclinical Antitumor Activity of Eribulin (Halaven®): Combination with Anticancer Agents of Differing Mechanisms," Anticancer Research, 2018, 38:3375-3385.

Beijnen et al., "Aspects of the degradation kinetics of doxombicin in aqueous solution," International Journal of Pharmaceutics, Elsevier, 1986, 32:123-131.

Bolotin et al., "Ammonium sulfate gradients for efficient and stable remote loading of amphipathic weak bases into liposomes and ligandoliposomes," Journal of Liposome Research, 1994, 4(1):455-479, XP000572717.

Cardoso et al., "ESO-ESMO 2nd international consensus guidelines for advanced breast cancer (ABC2)," The Breast, 2014, 23:489-502.

ClinicalTrials.gov [online], "An open-label Multicenter Multiple Dose Phase 1 Study to Establish the Maximum Tolerated Dose of E7389 Liposomal Formulation in Patients With Solid Tumors," Apr. 2016, National Library of Medicine, Bethesda MD, USA, —NCT01945710, retrieved from: URL<https://clinicaltrials.gov/archive/NCT01945710/2016 04 19>, 6 pages.

ClinicalTrials.gov [online], "Study NCT01848834—Study of MK-3475 in Participants With Advanced Solid Tumors (MK-3475-012/KeyNote-012," Apr. 2014, retrieved from: URL<https://clinicaltrials.gov/ct2/historv/NCT01848834?V24=View>, 7 pages.

Coates et al., "Tailoring therapies—improving the management of early breast cancer: St Gallen International Expert Consensus on the Primary Therapy of Early Breast Cancer 2015," Annals of Oncology, 2015, 26(8):1533-1546.

Communication under Rule 71(3) EPC in European Patent Application No. 10758754.5, dated Jan. 19, 2017, 54 pages.

Communication under Rule 71(3) EPC in European Patent Application No. 10758755.2, dated Febmarv 25, 2016, 7 pages.

Completion of Final Requirements in Philippine Patent Application No. 1-2011-501838, dated Aug. 27, 2015, 1 page.

Cortes et al., "Eribulin monotherapy versus treatment of physician's choice in patients with metastatic breast cancer (Embrace): a phase 3 open-label randomised study," Lancet, 2011, 377:914-923.

CTEP Rapid Communication, "Solicitation for Letters of Intent: Clinical trials—Chemical experiments, E7389, Halichondrin B analog (NSC 707389)," 11 pages.

Cullis et al., "pH Gradients and Membrane Transport in liposomal Systems," Trends in Biotechnology, 1991. 9(8) 268-272.

Danhier et al., "Strategies to improve the EPR effect for the delivery of anti-cancer nanomedicines," Cancer Cell & Microenvironment, 2015, 2:e808.

Decision on Grant in Russian Application No. 2011139715, dated Sep. 25, 2012, 14 pages (with English Translation).

Decision to Grant in Japanese Patent Application No. 2011-507239, dated Aug. 27, 2014, 5 pages (with English Translation).

Decision to Grant in Japanese Patent Application No. 2011-507240, dated May 7, 2014, 5 pages (with English Translation).

Decision to Grant in Japanese Patent Application No. 2014-092382, dated Jun. 2, 2015, 6 pages (with English Translation).

DesJardins et al., "A high-performance liquid chromatography-tandem mass spectrometry method for the clinical combination study of carboplatin and anti-tumor agent eribulin mesylate (E7389) in human plasma," Journal of Chromatography B, 2008, 875:373-382.

Devriese et al., "Eribulin mesylate pharmacokinetics in patients with solid tumors receiving repeated oral ketoconazole," Invest New Drugs, 2013, 31:381-389.

Dong et al., "Tumor-associated B7-HI promotes T-cell apoptosis: A potential mechanism of immune evasion," Natural Medicine, 2002, 8(8):793-800.

Dos Santos et al., "pH gradient loading of anthracyclines into cholesterol-free liposomes: enhancing drug loading rates through use of ethanol," Biochimica et Biophysica Acta, 2004, 1661:47-60.

Drummond, et al., Optimizing Liposomes for Delivery of Chemotherapeutic Agents to Solid Tumors, Pharmacological Reviews, 1999, 51(4):691-743.

Dybdal-Hargreaves et al., "Eribulin Mesylate: Mechanism of Action of a Unique Microtubule-Targeting Agent," Clinical Cancer Research, 2015, 21(11):2445-2452.

Eisai Co., Ltd., "FY2011 Financial Results Presentation," May 15, 2012, 68 pages (with English Translation).

Eisai Co., Ltd., "Halaven®," Code DI-T-HAL107, 6th edition, Feb. 2016, pp. 1-6 (with English Translation).

Eisai Co., Ltd., "Material Safety Data Sheet for Eribulin Mesylate," Oct. 2009, prepared by Greg Baker, 6 pages.

Eisai Co., Ltd., Eisai Public Relations Department, "Eisai and Merck Enter Collaboration to Explore Novel Combination Regimens of Anti-PD-I Therapy with Multi-targeting RTK Inhibitor and Microtubule Dynamics in Multiple Types of Cancer," Mar. 4, 2015, retrieved from: URL<http//www.eisai.com/news/news201518.html>, 8 pages.

Eisai Co., Ltd., News Release No. 19-72, "Eisai to Present Abstracts on Oncology Products and Pipeline at ESMO 2019 Congress," dated Sep. 24, 2019, 3 pages.

Examiner's Answer in U.S. Appl. No. 14/061,426 dated Feb. 28, 2020, 3 pages.

Exceipted file history of U.S. Appl. No. 13/260,864: Issue fee payment (Apr. 9, 2018); Supplemental Notice of Allowability (Jan. 24, 2018); Corrected Filing Receipt (Jan. 17, 2018); Notice of Allowance and Issue Fee Due (Jan. 8, 2018).

Extended European Search Report in European Patent Application No. 10758754.5 dated Oct. 8, 2012, 10 pages.

Extended European Search Report in European Patent Application No. 10758755.2, dated Oct. 31, 2012 with corrected Written Opinion for EESR dated Dec. 19, 2012, 24 pages.

Extended European Search Report in European Patent Application No. 17789632.1, dated Nov. 27, 2019, 9 pages.

Fatouros et al., "Liposomes encapsulating prednisolone and prednisolone—cyclodextrin complexes: comparison of membrane integrity and drug release," European Journal of Pharmaceutical Sciences, 2001, 13:287-296.

Fenske et al., "Entrapment of small molecules and nucleic acid-based drugs in liposomes," Methods in Enzymology, 2005, 391:7-40.

Final and Non Final Office actions in U.S. Appl. No. 13/260,864, dated Nov. 10, 2015 and Oct. 14, 2015 respectively, 20 pages.

Final Rejection in Algerian Patent Application No. 110640, dated Aug. 18, 2013, 2 pages (with English Translation).

FormuMax Scientific Inc., "Doxoves-Liposome Doxombicin Compared to Doxil," Doxoves-Liposomal Doxombicin, 1995, 1-4, XP002684032, [Retrieved on Sep. 24, 2012], retrieved from: URL <www.liposomeexpert.com/categories/Dmg-Loaded-Liposomes>.

Gao et al., "Overexpression of PD-LI Significantly Associates with Tumor Aggressiveness and Postoperative Recurrence in Human Hepatocellular Carcinoma," Clin. Cancer Res., 2009, 15(3):971-979.

(56) References Cited

OTHER PUBLICATIONS

Response filed in Chinese Patent Application No. 202080042486.9 dated Jul. 4, 2023.
Amendment filed in Brazilian Patent Application No. 112021026170-2 dated Jun. 27, 2023.
Resolution in Peruvian Patent Application No. 001735-2011/DIN, dated Nov. 30, 2015, 50 pages (with English Translation).
Response filed in Algerian Patent Application No. 110640, dated Aug. 29, 2016, 26 pages (with English Translation).
Response filed in Australian Patent Application No. 2014200717, dated Dec. 22, 2015, 7 pages.
Response filed in Canadian Patent Application No. 2756811, dated Jan. 16, 2014, 15 pages.
Response filed in Canadian Patent Application No. 2756811, dated Jun. 19, 2013 to the Office Action issued on Dec. 19, 2012, 21 pages.
Response filed in Chilean Patent Application No. 2444-2011, dated Apr. 16, 2015 to the Office Action issued on Jan. 21, 2015, 142 pages (with English Translation).
Response filed in Chilean Patent Application No. 2444-2011, dated Jun. 5, 2015, 8 pages (with English Translation).
Response filed in Chilean Patent Application No. 2444-2011, dated Mar. 11, 2014 to the Opposition issued on Jan. 2014, 6 pages (with English Translation).
Response filed in Chilean Patent Application No. 2444-2011, dated Mar. 14, 2016 to the Office Action issued on Dec. 11, 2015, 12 pages (with English Translation).
Response filed in Chinese Patent Application No. 201080014698.2, dated Dec. 23, 2013 to Office Action issued on Aug. 8, 2013, 14 pages (with English Translation).
Response filed in Chinese Patent Application No. 201080014698.2, dated May 29, 2014 to the Office Action issued on Mar. 28, 2014, 13 pages (with English Translation).
Response filed in Colombian Patent Application No. 11-130828, dated Dec. 2, 2013, 24 pages (with English Translation).
Response filed in Colombian Patent Application No. 11-130828, dated Jan. 14, 2013 to the Opposition dated Jul. 25, 2012, 10 pages (with English Translation).
Response filed in Egyptian Patent Application No. PCT1637/2011, dated Apr. 18, 2016, 20 pages (with English Translation).
Response filed in Egyptian Patent Application No. PCT1637/2011, dated Mar. 30, 2017, to the Office Decision issued on Jan. 3, 2017, 21 pages (with English Translation).
Response filed in European Patent Application No. 10758754.5, dated Aug. 1, 2014 to Communication to Art 94(3) issued on Jan. 24, 2014, 15 pages.
Response filed in European Patent Application No. 10758754.5, dated May 3, 2013 to the Office Action issued on Oct. 25, 2012 and to the EESR issued on Oct. 8, 2012 , 8 pages.
Response filed in European Patent Application No. 10758755.2, dated Jun. 3, 2014 to the Office Action issued on Jan. 24, 2014, 82 pages.
Response filed in European Patent Application No. 10758755.5, dated May 29, 2013 to the EESR issued on Nov. 19, 2012, 10 pages.
Response filed in European Patent Application No. 17789632.1, dated Jun. 24, 2020, to the Communication Pursuant to Rules 70(2)/70a(2) EPC issued on Dec. 17, 2019, including Amendment, 5 pages.
Response filed in Indian Patent Application No. 6850/DELNP/201 I, dated Oct. 3, 2017 to Result for Hearing Notice, including Amendment, 320 pages.
Response filed in Indonesian Patent Application No. WO0201103470, dated Mar. 25, 2014, 7 pages (with English Translation).
Response filed in Japanese Patent Application No. 2011-507239, dated Apr. 28, 2014 to the Office Action issued on Feb. 27, 2014, 5 pages (with English Translation).
Response filed in Japanese Patent Application No. 2011-507240, dated Apr. 7, 2014 to the Office Action issued on Feb. 6, 2014, 26 pages (with English Translation).
Response filed in Japanese Patent Application No. 2014-092382, dated Mar. 27, 2015 to the Office Action issued on Jan. 28, 2015, including Amendment and argument, 13 pages (with English Translation).
Response filed in Korean Patent Application No. 10-2011-7022860, dated Dec. 24, 2014 to the Notice of Final Rejection dated Sep. 23, 2014, 18 pages (with English Translation).
Response filed in Korean Patent Application No. 10-2011-7022860, dated Feb. 28, 2013 to the Office Action issued on Dec. 28, 2012, 31 pages (with English Translation).
Response filed in Korean Patent Application No. 10-2011-7022860, dated Jan. 22, 2014 to the Office Action issued on Jul. 22, 2013, 31 pages (with English Translation).
Response filed in Korean Patent Application No. 10-2011-7022860, dated Jul. 18, 2014 to the Office Action issued on May 20, 2014, including amendment, 15 pages (with English Translation).
Response filed in Malaysian Patent Application No. PI2011004382, dated Jun. 14, 2013 to Substantive Examination Adverse Report issued on Apr. 15, 2013, 6 pages.
Response filed in Mexican Patent Application No. MX/a/2011/009632 dated Jan. 7, 2013, to the Office Action dated Aug. 7, 2012, 17 pages (with English Translation).
Response filed in Mexican Patent Application No. MX/a/2011/009632, dated Jun. 17, 2014, 22 pages (with English Translation).
Response filed in Mexican Patent Application No. MX/a/2011/009632, dated Sep. 18, 2013 to the Office Action issued on Apr. 22, 2013, 20 pages (with English Translation).
Response filed in New Zealand Patent Application No. 595212, dated Feb. 7, 2014, 4 pages.
Response filed in Peruvian Patent Application No. 001735-2011/DIN, dated Aug. 12, 2015 18 pages (with English Translation).
Response filed in Peruvian Patent Application No. 001735-2011/DIN, dated Jan. 20, 2014, 2 pages (with English Translation).
Response filed in Peruvian Patent Application No. 001735-2011/DIN, dated Jan. 21, 2013 to the Peruvian Opposition issued Nov. 23, 2012, 5 pages (with English Translation).
Response filed in Peruvian Patent Application No. 001735-2011/DIN, dated May 20, 2015, 48 pages (with English Translation).
Response filed in Peruvian Patent Application No. 001735-2011/DIN, dated Oct. 27, 2014 to Office Action issued on Sep. 29, 2014, 3 pages.
Response filed in Peruvian Patent Application No. 001798-2015, dated Jan. 4, 2020 to the Observation received on Oct. 16, 2019, 12 pages (with English Translation).
Response filed in Peruvian Patent Application No. 1798-2015, dated Apr. 28, 2016, 10 pages (with English Translation).
Response filed in Philippine Patent Application No. 1-2011-501838, dated Jul. 24, 2015, 13 pages.
Response filed in Philippine Patent Application No. 1-2011-501838, dated Nov. 11, 2014, submitting English translation of JP 5551683 B2 in reply to Paper No. 9 mailed Sep. 17, 2014, 59 pages.
Response filed in Philippine Patent Application No. 1-2011-501838, dated Sep. 18, 2015 to the Office Action issued on Aug. 27, 2015, 1 page.
Response filed in Philippine Patent Application No. 1-2011-501838, dated Sep. 30, 2013 to the Office Action issued on Aug. 8, 2013, 1 page.
Response filed in Russian Patent Application No. 201 | 139715/20(059371), dated Jan. 30, 2012, 12 pages (with partial English Translation).
Response filed in Ukrainian Patent Application No. a201111426, dated Jun. 11, 2013, to the Office Action (Preliminary Conclusion on Non-patentability) , 9 pages (with English Translation).
Response filed in U.S. Appl. No. 13/260,864, dated Aug. 1, 2017, including Request for Continued Examination, 51 pages.
Response filed in U.S. Appl. No. 13/260,864, dated Dec. 22, 2016, including Amendment, 22 pages.
Response filed in U.S. Appl. No. 13/260,864, dated Mar. 9, 2016 to the Final Office Action issued on Nov. 20, 2015, including Amendment, 16 pages.
Corrected Notice of Allowability issued in related U.S. Appl. No. 14/061,426, dated Apr. 27, 2023.

(56) References Cited

OTHER PUBLICATIONS

Notice of Allowance issued in related U.S. Appl. No. 14/061,426, dated Apr. 18, 2023.
Response filed in related European Patent Application No. 17789632.1, dated Apr. 14, 2023.
Response filed in related Pakistani Patent Application No. 803/2010, dated Nov. 22, 2022.
Corrected Notice of Allowability in U.S. Appl. No. 16/090,360, dated Dec. 9, 2022, 2 pages.
Final Office Action in U.S. Appl. No. 16/090,360, dated Jan. 25, 2022, 20 pages.
Notice of Allowance in U.S. Appl. No. 16/090,360, dated Nov. 7, 2022, 5 pages.
Response filed in U.S. Appl. No. 16/090,360, dated Dec. 29, 2021, 11 pages.
Office Action issued in Chinese Patent Application No. 202080042486.9 dated Mar. 22, 2023.
Poster Presentation for American Association for Cancer Research Annual Meeting 2023 on Apr. 18, 2023.
Response to Official Communication of Jul. 6, 2023 filed in counterpart European Patent Application No. 20847524.4 dated Dec. 6, 2023.
Response to Official Communication of Sep. 18, 2023 filed in counterpart Indonesian Patent Application No. P00202111802 dated Dec. 8, 2023.
Request for Reexamination filed in counterpart Chinese Patent Application No. 202080042869 on Dec. 5, 2023.
Olson et al., "Mouse Models for Cancer Immunotherapy Research," Cancer Discovery, 8 (11): 1358-1365 (2018).
Office Action issued in Indonesian Patent Application No. P00202111802 dated Sep. 18, 2023.
Office Action issued in Chinese Patent Application No. 202080042486.9 dated Aug. 22, 2023.
Administrative Appeal Against Rejection filed in Argentine Patent Application No. PI00103420, dated Jan. 24, 2022, 19 pages with English translation.
Communication under Rule 71 (3) in European Patent Application No. 1778963 2.1, dated Dec. 21, 2022, 33 pages.
Decision to Grant in Japanese Patent Application No. 2018-514683, dated Jan. 14, 2022, 4 pages (with English Translation).
Final Office Action in Argentine Patent Application No. P 100103420, dated Oct. 7, 2020, 11 pages (with English Translation).
International Preliminary Report on Patentability in International Patent Application No. PCT/JP2020/028663, dated Feb. 10, 2022, 5 pages.
Letter of a Preliminary Acceptance in Jordanian Patent Application No. 0318/2020, dated May 30, 2018, 3 pages (with English Translation).
Letters Patent for Iranian Patent No. 83009, granted on Jun. 3, 2014, 2 pages (with English Translation).
Letters Patent for Iraqi Patent No. 3805, granted on Mar. 4, 2014, 2 pages (with English Translation).
Letters Patent for Jordanian Patent No. 3282, granted on Dec. 19, 2018, 2 pages (with English Translation).
Letters Patent for Lebanese Patent No. 9155, granted on Oct. 7, 2010, 2 pages (with English Translation).
Letters Patent for Thai Patent No. 85826, granted on Dec. 13, 2021, 2 pages (with English Translation).
Letters Patent for Yemeni Patent No. 196, granted on Nov. 25, 2017, 6 pages (with English Translation).
Mano, "A separate assay of released and liposomal encapsulated eribulin in dog plasma by liquid chromatography with tandem mass spectrometry for its application to a pharmacokinetic study," Journal of Separation Science, 2022, 10 pages.
Masuda et al., "Phase 1 study of the liposomal formulation of eribulin (E7389-LF): Results from the breast cancer expansion cohort," European Journal of Cancer, 2022, 168: 108-118.
Nih.gov [Online], "Nivolumab," Year introduced: 2019 (2010), [Retrieved on Jun. 4, 2022], retrieved from: URL<https://www.ncbi.nlm.nih.gov/mesh/?term=BMS-936558>, 2 pages.
Niwa et al., "Antitumor activity of liposomal formulation of eribulin combined with anti-PD-1," Poster Presentation No. 5584, Eisai Co., Ltd., Tsukuba, Japan, 1 page.
Notice of Allowance in South African Patent Application No. 2021/10686, dated Jul. 8, 2022, 2 pages.
Notice of Allowance in U.S. Appl. No. 14/061,426, dated Jan. 14, 2022, 21 pages.
Notice of Allowance in U.S. Appl. No. 14/061,426, dated Mar. 31, 2022, 11 pages.
Notice of Allowance in U.S. Appl. No. 14/061,426, dated Aug. 4, 2022, 11 pages.
Notice of Allowance in U.S. Appl. No. 14/061,426, dated Dec. 19, 2022, 12 pages.
Notice of Substantive Examination Fees in Gulf Cooperation Council Patent Application No. 2010/16760, dated Oct. 22, 2013, 2 pages (with English Translation).
Office Action in Argentine Patent Application No. PI00103420, dated Jun. 9, 2021, 14 pages (with English Translation).
Office Action in European Patent Application No. 17789632.1, dated Jul. 12, 2022, 31 pages.
Office Action in Gulf Cooperation Council Patent Application No. 2010/16760, dated Sep. 16, 2014, 4 pages.
Office Action in Gulf Cooperation Council Patent Application No. 2010/16760, dated Jan. 26, 2014, 6 pages.
Office Action issued in Jordanian Patent Application No. 0381/2020, dated Apr. 23, 2018.
Office Action in Pakistani Patent Application No. 803/2010, dated Sep. 29, 2011, 2 pages.
Patent Certificate for Japanese Patent No. 7015237, granted on Jan. 25, 2022, 3 pages (with English Translation).
Patent Certificate for Peruvian Patent No. 10407, granted on Sep. 1, 2020, 2 pages (with English Translation).
Payment of Substantive Examination Fees in Gulf Cooperation Council Patent Application No. 2010/16760, dated Jan. 13, 2014, 2 pages (with English Translation).
Request for Continued Examination in U.S. Appl. No. 14/061,426, dated Feb. 10, 2022, 9 pages.
Request for Continued Examination in U.S. Appl. No. 14/061,426, dated Jun. 28, 2022, 3 pages.
Request for Continued Examination in U.S. Appl. No. 14/061,426, dated Oct. 7, 2022, 9 pages.
Response filed in Argentine Patent Application No. PI00103420, dated Aug. 4, 2020, 53 pages (with English Translation).
Response filed in Argentine Patent Application No. PI00103420, dated May 13, 2021, 23 pages (with English Translation).
Response filed in Egyptian Patent Application No. PCT 1637/2011, dated Jun. 27, 2022, 7 pages (with English Translation).
Response filed in European Patent Application No. 17789632.1, dated Nov. 9, 2022, 24 pages.
Response filed in Gulf Cooperation Council Patent Application No. 2010/16760, dated Aug. 24, 2014, 39 pages (with English Translation).
Response filed in Gulf Cooperation Council Patent Application No. 2010/16760, dated Jan. 21, 2015, 135 pages (with English Translation).
Response filed in Jordanian Patent Application No. 0318/2010, dated May 21, 2018, 15 pages (with English Translation).
Sato et al., "Phase 1 Dose Escalation Study of the Liposomal Formulation of Eribulin (E7389-LF) in Japanese Patients with Advanced Solid Tumors," Clinical Cancer Research, 2022, 30 pages.
Submission Document in European Patent Application No. 20847524.4, dated Jul. 25, 2022, 6 pages.
Submission Document in U.S. Appl. No. 17/563,162, dated May 31, 2022, 4 pages.
Substantive Examination in Argentine Patent Application No. PI00103420, dated Nov. 6, 2019, 18 pages (with English Translation).
Topalian et al., "Safety, activity, and immune correlates of anti-PD-I antibody in cancer," New England Journal of Medicine, 2012, 366(26): 2443-2454.
Official Decision in Egyptian Patent Application No. PCT1637/201 I, dated Dec. 29, 2020, 10 pages (with English Translation).

(56) References Cited

OTHER PUBLICATIONS

Notice of Allowance in U.S. Appl. No. 16/090,360, dated Jun. 22, 2023, 9 pages.
Patent Certificate for European Patent No. 3449921, granted on May 31, 2023, 2 pages.
Request for Continued Examination in U.S. Appl. No. 14/061,426, dated Jun. 15, 2023, 14 pages.
Response filed in U.S. Appl. No. 13/260,864, dated May 26, 2015, including Supplemental Amendment, Statement of Substance of Interview, and Applicant-Initiated Interview Summary issued on Apr. 27, 2015, 17 pages.
Response filed in U.S. Appl. No. 13/260,864, dated Oct. 13, 2015, to the Non-Final Office Action issued on Jul. 13, 2015, 17 pages.
Response filed in U.S. Appl. No. 13/260,864, including Amendment and Request for Continued Examination, dated Mar. 23, 2015, 23 pages.
Response filed in U.S. Appl. No. 13/260,864, including amendment, dated Sep. 9, 2014, 19 pages.
Response filed in U.S. Appl. No. 13/260,872, including amendments and two exhibits, dated Feb. 1, 2013, 167 pages.
Response filed in U.S. Appl. No. 14/061,426, dated Jul. 15, 2015, 4 pages.
Response filed in U.S. Appl. No. 14/061,426, dated Apr. 25, 2018, including Amendment and RCE, 32 pages.
Response filed in U.S. Appl. No. 14/061,426, dated Aug. 26, 2019 to the Final Office Action issued on May 30, 2019, 7 pages.
Response filed in U.S. Appl. No. 14/061,426, dated Aug. 30, 2017 to the Office Action issued on May 31, 2017, 48 pages.
Response filed in U.S. Appl. No. 14/061,426, dated Dec. 22, 2015, 125 pages.
Response filed in U.S. Appl. No. 14/061,426, dated Dec. 23, 2019 to the Final Office Action issued on May 30, 2019, 50 pages.
Response filed in U.S. Appl. No. 14/061,426, dated Feb. 7, 2019, to the Office Action issued on Nov. 19, 2018, 23 pages.
Response filed in U.S. Appl. No. 14/061,426, dated Mar. 17, 2020 to the Examiner's Answer issued on Feb. 28, 2020, 3 pages.
Response filed in U.S. Appl. No. 14/061,426, dated Oct. 24, 2013, including Preliminary Amendment, 1 page.
Response filed in U.S. Appl. No. 14/061,426, dated Sep. 19, 2016, including RCE, ADS, and Amendment, 70 pages.
Response filed in U.S. Appl. No. 16/090,360, dated Jan. 10, 2020 to the Office Action received on Oct. 21, 2019, 9 pages.
Response filed in Vietnamese Patent Application No. 1-2011-02950, dated Dec. 13, 2013, 8 pages (with English Translation).
Response filed in Vietnamese Patent Application No. 1-2011-02950, dated May 30, 2016, 4 pages (with English Translation).
Response in Taiwanese Patent Application No. 099109838, dated Dec. 27, 2012 to the Office Action dated Jun. 22, 2012, 21 pages.
Restriction in U.S. Appl. No. 14/061,426, dated May 15, 2015, 7 pages.
Satsuka, "Recent evolution of liposome application," NTS, 2005, 16 pages (with English Translation).
Schoffski et al., "Activity of eribulin mesylate in patients with soft-tissue sarcoma: a phase 2 study in four independent histological subtypes," The Lancet Oncology, 2011, 12: 1045-1052.
Sharpe et al., "The function of programmed cell death 1 and its ligands in regulating autoimmunity and infection," Nature Immunology, 2007, 8(3):239-245.
Shimauchi et al., "Augmented expression of programmed death-1 in both neoplastic and non-neoplastic CD4 + T-cells in adult T-cell leukemia/lymphoma," Int. J. Cancer, 2007, 121 :2585-2590.
Takahashi et al., "One-year follow-up results of eribulin for soft-tissue sarcoma including rare subtypes in a real-world observational study in Japan," Poster Display, Abstract No. 1683P displayed Sep. 28, 2019, European Society for Medical Oncology (ESMO) 2019 Congress, Barcelona, Spain, 1 page.
TheFreeDictionary.com [Online], "Residues," [Retrieved on Jul. 15, 2014], retrieved from: URL <http://medical-dictionary.thefreedictionary.com/p/Residues>, 2 pages.

Thompson et al., "PD-1 is expressed by tumor-infiltrating immune cells and is associated with poor outcome for patients with renal cell carcinoma," Clin. Cancer Res., 2007, 13(6):1757-1761.
Thompson et al., "Significance of B7-H 1 Overexpression in Kidney Cancer," Clinical Genitourinary Cancer, 2006, 5(3):206-211.
Tolaney et al., "Phase lb/2 study to evaluate eribulin mesylate in combination with pembrolizumab in patients with metastatic triple-negative breast cancer," [Abstract No. 177], Eur. J. Cancer, 2017, 72:SI6.
Twelves et al., "Efficacy of eribulin in women with metastatic breast cancer: a pooled analysis of two phase 3 studies," Breast Cancer Res. Treat., 2014, 148:553-561.
Voluntary Amendment filed in Cambodian Patent Application No. KH/P/10/00097, dated Jul. 7, 2016, 4 pages.
Wang et al. "Eribulin mesilate," Drugs of the Future, 2007, 32(8): 681-698.
Whatsthedose.com [online], "NORMOSOL®-R Ph 7.4—Packaging Insert," Hospira, Inc., revised Oct. 2006, [Retrieved on Jul. 20, 2012], retrieved from: URL<http://whatsthedose.com/spl/0409-7670.html>, 10 pages.
Written Opinion in International Patent Application No. PCT/JP2018/020456, dated Aug. 28, 2018, 15 pages (with English Translation).
Written Opinion in International Patent Application No. PCT/US2016/020734, dated Apr. 28, 2016, 8 pages.
Written Opinion in Singaporean Patent Application No. l1201706872S, dated Jun. 27, 2018, 7 pages.
Written Opinion in Singaporean Patent Application No. l1201706872S, dated Nov. 5, 2019, 10 pages.
Yamamoto et al., "Phase 1 study of liposomal formulation of eribulin (E7389-LF) in Patients with Advanced Solid Tumors: Primary Results of the Dose-Escalation Part," Poster Display, Abstract No. 348P, displayed Sep. 29, 2019, European Society for Medical Oncology (ESMO) 2019 Congress, Barcelona, Spain, 1 page.
Yang et al., "PD-LI Interaction Contributes to the Functional Suppression of T-Cell Responses to Human Uveal Melanoma Cells In Vitro," Invest. Ophthalmol. Vis. Sci., 2008, 49(6):2518-2525.
Yi et al., "Biomarkers for predicting efficacy of PD-1/PD-LI inhibitors," Molecular Cancer, 2018, 17:129.
Yin et al., "Enhanced Permeability and Retention (EPR) Effect Based Tumor Targeting: The Concept, Annlication and Prospect," JSM Clinical Oncology and Research, 2014, 2(1):1010.
Yu et.al., "Characterization of the pharmacokinetics of a liposomal formulation of eribulin mesylate (E7389) in mice," International Journal of Pharmaceutics, 2013, 443:9-16.
Zibelman et al., "Checkpoint Inhibitors and Urothelial Carcinoma: The Translational Paradigm," Oncology, 2016, 30 (2):160-162.
Zucker et al., "Liposome drugs' loading efficiency: A working model based on loading conditions and drug's physicochemical properties," Journal of Controlled Release, 2009, 139(1):73-80.
Notice of Allowance issued in U.S. Appl. No. 14/061,426 dated Jul. 28, 2023.
Kharkevich D.A. Pharmacology, "textbook. 10th edition corrected", revised and supplemented. M.: GEOTAR-Media, 2010, p. 72-p. 82.
Small medical encyclopedia in 6 volumes, "chief editor V.I. Pokrovsky M.", Medicine, V. 4. P.81-83; V. 5. P.90-96, 1996.
Action issued in Vietnamese Patent Application No. 1-2021-08263 dated Feb. 29, 2024.
Action issued in Taiwanese Patent Application No. 109125099 dated Mar. 25, 2024.
Kan Yonemori et al., "E7389-LF as a First-line Chemotherapy for Patients With Metastatic/Advanced HER2-Negative Breast Cancer: Results From a Phase 1 Study Dose-Expansion Part, Poster #: 405", European Society for Medical Oncology (ESMO) annual meeting, Oct. 20-24, 2024, 2023.
Akihito Kawazoe et al., "Phase II Study of the Liposomal Formulation of Eribulin (E7389-LF) in Combination with Nivolumab: Results from the Gastric Cancer Cohort", Clinical Cancer Research, Apr. 1, 2024, 30(7), p. 1264-p. 1272.
Makoto Nishio et al., "Phase 2 Study of the Liposomal Formulation of Eribulin (E7389-LF)in Combination with Nivolumab: Results from the Small Cell Lung Cancer Cohort", Cancer Research Communications, 2024, 4(1), p. 226-p. 235.

(56) References Cited

OTHER PUBLICATIONS

Hiroyuki Yasojima et al., "E7389-LF as 1L chemotherapy for advanced/metastatic HER2-negative breast cancer (HER2-BC): Phase 1 dose-expansion study, Abstract #: MO9-3", Japanese Society of Medical Oncology Annual Meeting (JSMO2024), Feb. 22-24, 2024.

Hisato Kawakami et al., "Phase 2 small cell lung cancer cohort of liposomal eribulin given with nivolumab: Overall survival update, Abstract#: MO58-1", Japanese Society of Medical Oncology Annual Meeting (JSMO2024), Feb. 22-24, 2024.

Akihito Kawazoe et al., "Results of a phase 2 trial of E7389-LF + nivolumab in patients with gastric or esophageal cancers, Abstract#: MO57-2", Japanese Society of Medical Oncology Annual Meeting (JSMO2024), Feb. 22-24, 2024.

Moe Tamura et al., "Combination activity of eribulin liposomal formulation and anti-PD-1 antibody after tumor regrowth during anti-PD-1 antibody treatment in mice, Poster#: 2955", American Association for Cancer Research (AACR) Annual Meeting 2024, Apr. 5-10, 2024.

\* cited by examiner

PHARMACEUTICAL COMPOSITION FOR TREATING TUMOR

The claimed invention was made by, or on behalf of, one or more of the following parties to a joint research agreement: Eisai R&D Management Co., Ltd. and Ono Pharmaceutical Co., Ltd. The agreement was in effect on and before the date the claimed invention was made, and the claimed invention was made as a result of activities undertaken within the scope of the agreement.

TECHNICAL FIELD

The present invention relates to a pharmaceutical composition for treating tumor.

BACKGROUND ART

Eribulin represented by formula (I) is used as a therapeutic agent for breast cancer and soft tissue tumor.

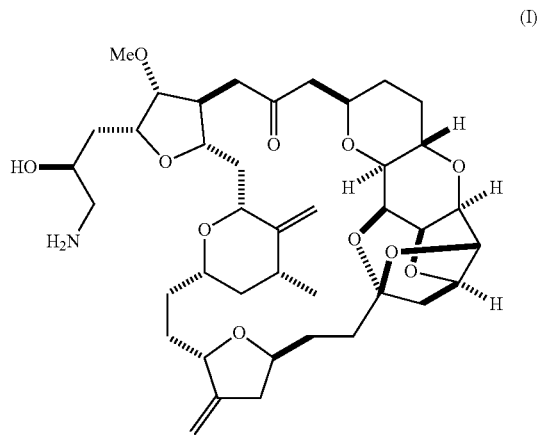

Patent Literature 1 discloses Eribulin or a pharmaceutically acceptable salt thereof and a method of producing the same. Patent Literatures 2 and 3 disclose methods for producing Eribulin and Eribulin mesylate, which is a mesylate (methanesulfonate) thereof. Patent Literature 4 discloses a method of inhibiting growth of cancer in a patient by administering Eribulin or a pharmaceutically acceptable salt thereof to the patient. Patent Literature 5 discloses a method of treating cancer in a patient by administering Eribulin or a pharmaceutically acceptable salt thereof to the patient in combination with a certain second anticancer agent. Patent Literature 6 discloses a method of treating cancer in a patient by administering Eribulin or a pharmaceutically acceptable salt thereof to the patient in combination with a second therapeutic approach. Patent Literatures 7 and 8 disclose liposomal compositions comprising Eribulin mesylate. Patent Literature 9 discloses a method for treating breast cancer, comprising administering a combination of Eribulin or a pharmaceutically acceptable salt thereof and a programmed cell death 1 protein (PD-1) antagonist.

PD-1 is recognized as an important factor in maintenance of immunoregulation and peripheral tolerance. PD-1 is moderately expressed in naive T cells, B cells, and NK T cells, and upregulated by T/B cell receptor signal transduction in lymphocytes, monocytes, and myeloid cells (Non Patent Literature 1). Meanwhile, PD-L 1 is expressed in various cancer cells or T/B cells, macrophages, mDCs, plasmacytoid DCs:(pDCs), bone marrow mast cells, and the like.

The two known PD-1 ligands PD-L1 (B7-H1) and PD-L2 (B7-DC) are expressed in human cancer occurring in various tissues. For example, in a large amount of sample sets of ovarian cancer, renal cancer, colorectal cancer, pancreatic cancer, liver cancer, and melanoma, the PD-L1 expression has been shown to correlate with poor prognosis and decreased overall survival, regardless of subsequent treatment (Non Patent Literatures 2 to 13). Similarly, it was found that the PD-1 expression in tumor-infiltrating lymphocytes is characteristic of functionally impaired T cells in breast cancer and melanoma (Non Patent Literatures 14 to 15) and correlates with poor prognosis in kidney cancer (Non Patent Literature 16). Therefore, it has been proposed to block the immunosuppression mechanism that cancer cells bring, such as the interaction of tumor cells expressing PD-L1 with T cells expressing PD-1, and thereby bring the immune response to tumor.

Several monoclonal antibodies that inhibit the interaction between PD-1 and either or both of PD-1 ligands PD-L 1 and PD-L2 are under clinical development for treating cancer. It has been proposed that the efficacy of such antibodies may be increased when administered in combination with another approved or experimental cancer therapy, for example, radiation, surgery, a chemotherapeutic agent, a targeted therapy, an agent that inhibits another signaling pathway that is dysregulated in tumor, and another immunostimulant.

CITATION LIST

Patent Literature

Patent Literature 1: WO 99/65894
Patent Literature 2: WO 2005/118565
Patent Literature 3: WO 2011/094339
Patent Literature 4: U.S. Pat. No. 6,469,182
Patent Literature 5: U.S. Application Publication No. 2006/104984
Patent Literature 6: U.S. Pat. No. 6,653,341
Patent Literature 7: WO 2010/113984
Patent Literature 8: WO 2017/188350
Patent Literature 9: WO 2016/141209

Non Patent Literature

Non Patent Literature 1: Sharpe, A. H, Wherry, E. J., Ahmed R., and Freeman G. J., The function of programmed cell death 1 and its ligands in regulating autoimmunity and infection. Nature Immunology (2007); 8: 239-245.

Non Patent Literature 2: Dong H et al., Tumor-associated B7-H1 promotes T-cell apoptosis: a potential mechanism of immune evasion. Nat Med. 2002 August; 8(8): 793-800.

Non Patent Literature 3: Yang et al., PD-1 interaction contributes to the functional suppression of T-cell responses to human uveal melanoma cells in vitro. Invest Ophthalmol Vis Sci. 2008 June; 49(6 (2008): 49: 2518-2525.

Non Patent Literature 4: Ghebeh et al., The B7-H1 (PD-L1) T lymphocyte-inhibitory molecule is expressed in breast cancer patients with infiltrating ductal carcinoma: correlation with important high-risk prognostic factors. Neoplasia (2006) 8: 190-198.

Non Patent Literature 5: Hamanishi J et al., Programmed cell death 1 ligand 1 and tumor-infiltrating CD8+ T lymphocytes are prognostic factors of human ovarian cancer. Proceeding of the National Academy of Sciences (2007): 104: 3360-3365.

Non Patent Literature 6: Thompson R H et al., Significance of B7-H1 overexpression in kidney cancer. Clinical genitourin Cancer (2006): 5: 206-211.

Non Patent Literature 7: Nomi, T. Sho, M., Akahori, T., et al., Clinical significance and therapeutic potential of the programmed death-1 ligand/programmed death-1 pathway in human pancreatic cancer. Clinical Cancer Research (2007); 13: 2151-2157.

Non Patent Literature 8: Ohigashi Y et al., Clinical significance of programmed death-1 ligand-1 and programmed death-1 ligand 2 expression in human esophageal cancer. Clin. Cancer Research (2005): 11: 2947-2953.

Non Patent Literature 9: Inman et al., PD-L1 (B7-H1) expression by urothelial carcinoma of the bladder and BCG-induced granulomata: associations with localized stage progression. Cancer (2007): 109: 1499-1505.

Non Patent Literature 10: Shimauchi T et al., Augmented expression of programmed death-1 in both neoplasmatic and nonneoplastic CD4+ T-cells in adult T-cell Leukemia/Lymphoma. Int. J. Cancer (2007): 121: 2585-2590.

Non Patent Literature 11: Gao et al., Overexpression of PD-L 1 significantly associates with tumor aggressiveness and postoperative recurrence in human hepatocellular carcinoma. Clinical Cancer Research (2009) 15: 971-979.

Non Patent Literature 12: Nakanishi J., Overexpression of B7-H1 (PD-L1) significantly associates with tumor grade and postoperative prognosis in human urothelial cancers. Cancer Immunol Immunother. (2007) 56: 1173-1182.

Non Patent Literature 13: Hino et al., Tumor cell expression of programmed cell death-1 is a prognostic factor for malignant melanoma. Cancer (2010): 116: 1757-1766.

Non Patent Literature 14: Ghebeh H., Foxp3+ tregs and B7-H1+/PD-1+ T lymphocytes co-infiltrate the tumor tissues of high-risk breast cancer patients: implication for immunotherapy. BMC Cancer. 2008 Feb. 23; 8:57.

Non Patent Literature 15: Ahmadzadeh M. et al., Tumor antigen-specific CD8 T cells infiltrating the tumor express high levels of PD-1 and are functionally impaired. Blood (2009) 114: 1537-1544.

Non Patent Literature 16: Thompson R H et al., PD-1 is expressed by tumor infiltrating cells and is associated with poor outcome for patients with renal carcinoma. Clinical Cancer Research (2007) 15: 1757-1761.

SUMMARY OF INVENTION

Technical Problem

The present invention is directed to provide a new pharmaceutical composition for treating tumor.

Solution to Problem

The present inventors have studied diligently and, as a result, found that the combined administration of a liposomal composition comprising Eribulin or a pharmaceutically acceptable salt thereof and a PD-1 antagonist exhibits unexpected antitumor effect, thereby completing the present invention.

Accordingly, the present disclosure is as follows.

[1] A pharmaceutical composition for treating tumor, comprising a liposomal composition comprising Eribulin or a pharmaceutically acceptable salt thereof wherein the pharmaceutical composition is administered in combination with a PD-1 antagonist.

[2] A pharmaceutical composition for treating tumor, comprising a PD-1 antagonist, wherein the pharmaceutical composition is administered in combination with a liposomal composition comprising Eribulin or a pharmaceutically acceptable salt thereof.

[3] The pharmaceutical composition according to [1] or [2] above, wherein the liposomal composition comprising Eribulin or a pharmaceutically acceptable salt thereof and the PD-1 antagonist are administered simultaneously, separately, continuously, or at a time interval.

[4-1] The pharmaceutical composition according to any of [1] to [3] above, wherein Eribulin or the pharmaceutically acceptable salt thereof is Eribulin mesylate.

[4-2] The pharmaceutical composition according to [4-1] above, wherein Eribulin mesylate is administered at 0.5 to 3 mg/m$^2$ (body surface area) once in 1 week, 2 weeks or 3 weeks.

[4-3] The pharmaceutical composition according to [4-1] above, wherein Eribulin mesylate is administered at 0.5 to 2 mg/m$^2$ (body surface area) once in 1 week, 2 weeks or 3 weeks.

[4-4] The pharmaceutical composition according to [4-1] above, wherein Eribulin mesylate is administered at about 1.5 mg/m$^2$ (body surface area) once in 1 week, 2 weeks or 3 weeks.

[4-5] The pharmaceutical composition according to [4-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[5] The pharmaceutical composition according to any of [1] to [4-5] above, wherein the PD-1 antagonist is an anti-PD-1 antibody.

[6-1] The pharmaceutical composition according to [5] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI- A1110, ENUM388D4, ENUM244C8, GLS010, CS1003, BAT-1306, AK103, BI754091, LZM009, CMAB819, Sym021, SSI-361, JY034, HX008, ISU106 and CX-188.

[6-2] The pharmaceutical composition according to [5] above, wherein the anti-PD-1 antibody is selected from the group consisting of Nivolumab, Pembrolizumab, Cemiplimab, Sintilimab, and Toripalimab.

[6-3] The pharmaceutical composition according to [5] above, wherein the anti-PD-1 antibody is Nivolumab.

[6-4] The pharmaceutical composition according to [6-3] above, wherein Nivolumab is administered at 3 mg/kg (body weight) every 2 weeks, at 240 mg every 2 weeks, at 360 mg every 3 weeks or at 480 mg every 4 weeks.

[6-5] The pharmaceutical composition according to [5] above, wherein the anti-PD-1 antibody is Pembrolizumab.

[6-6] The pharmaceutical composition according to [6-5] above, wherein Pembrolizumab is administered at 200 mg every 3 weeks or at 400 mg every 6 weeks.

[6-7] The pharmaceutical composition according to [5] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[6-8] The pharmaceutical composition according to [5] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[7-1] The pharmaceutical composition according to any of [1] to [6-8] above, wherein the tumor is breast cancer, gastric cancer, esophageal cancer, small cell lung cancer, colorectal cancer, renal cancer, thymic carcinoma or intrahepatic cholangiocarcinoma.

[7-2] The pharmaceutical composition according to any of [1] to [6-8] above, wherein the tumor is breast cancer, gastric cancer, esophageal cancer, small cell lung cancer, colorectal cancer or renal cancer.

[7-3] The pharmaceutical composition according to any of [1] to [6-8] above, wherein the tumor is breast cancer.

[7-4] The pharmaceutical composition according to any of [1] to [6-8] above, for a patient with advanced, unresectable, or recurrent solid tumors without standard therapy or another effective therapy.

[7-5] The pharmaceutical composition according to any of [1] to [6-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[7-6] The pharmaceutical composition according to any of [1] to [6-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[8] A therapeutic agent for tumor, comprising a liposomal composition comprising Eribulin or a pharmaceutically acceptable salt thereof wherein the therapeutic agent is administered in combination with a PD-1 antagonist.

[9] A therapeutic agent for tumor, comprising a PD-1 antagonist, wherein the therapeutic agent is administered in combination with a liposomal composition comprising Eribulin or a pharmaceutically acceptable salt thereof.

[10] The therapeutic agent according to [8] or [9] above, wherein the liposomal composition comprising Eribulin or a pharmaceutically acceptable salt thereof and the PD-1 antagonist are administered simultaneously, separately, continuously, or at a time interval.

[11-1] The therapeutic agent according to any of [8] to [10] above, wherein Eribulin or the pharmaceutically acceptable salt thereof is Eribulin mesylate.

[11-2] The therapeutic agent according to [11-1] above, wherein Eribulin mesylate is administered at 0.5 to 3 mg/m$^2$ (body surface area) once in 1 week, 2 weeks or 3 weeks.

[11-3] The therapeutic agent according to [11-1] above, wherein Eribulin mesylate is administered at 0.5 to 2 mg/m$^2$ (body surface area) once in 1 week, 2 weeks or 3 weeks.

[11-4] The therapeutic agent according to [11-1] above, wherein Eribulin mesylate is administered at about 1.5 mg/m$^2$ (body surface area) once in 1 week, 2 weeks or 3 weeks.

[11-5] The therapeutic agent according to [11-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[12] The therapeutic agent according to any of [8] to [11-5] above, wherein the PD-1 antagonist is an anti-PD-1 antibody.

[13-1] The therapeutic agent according to [12] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[13-2] The therapeutic agent according to [12] above, wherein the anti-PD-1 antibody is selected from the group consisting of Nivolumab, Pembrolizumab, Cemiplimab, Sintilimab, and Toripalimab.

[13-3] The therapeutic agent according to [12] above, wherein the anti-PD-1 antibody is Nivolumab.

[13-4] The therapeutic agent according to [13-3] above, wherein Nivolumab is administered at 3 mg/kg (body weight) every 2 weeks, at 240 mg every 2 weeks, at 360 mg every 3 weeks or at 480 mg every 4 weeks.

[13-5] The therapeutic agent according to [12] above, wherein the anti-PD-1 antibody is Pembrolizumab.

[13-6] The therapeutic agent according to [13-5] above, wherein Pembrolizumab is administered at 200 mg every 3 weeks or at 400 mg every 6 weeks.

[13-7] The therapeutic agent according to [12] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[13-8] The therapeutic agent according to [12] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[14-1] The therapeutic agent according to any of [8] to [13-8] above, wherein the tumor is breast cancer, gastric cancer, esophageal cancer, small cell lung cancer, colorectal cancer, renal cancer, thymic carcinoma or intrahepatic cholangiocarcinoma.

[14-2] The therapeutic agent according to any of [8] to [13-8] above, wherein the tumor is breast cancer, gastric cancer, esophageal cancer, small cell lung cancer, colorectal cancer or renal cancer.

[14-3] The therapeutic agent according to any of [8] to [13-8] above, wherein the tumor is breast cancer.

[14-4] The therapeutic agent according to any of [8] to [13-8] above, for a patient with advanced, unresectable, or recurrent solid tumors without standard therapy or another effective therapy.

[14-5] The therapeutic agent according to any of [8] to [13-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[14-6] The therapeutic agent according to any of [8] to [13-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[15] A method for treating tumor, comprising administering a liposomal composition comprising Eribulin or a pharmaceutically acceptable salt thereof and a PD-1 antagonist to a patient in need thereof.

[16] The method according to [15] above, wherein the liposomal composition comprising Eribulin or a pharmaceutically acceptable salt thereof and the PD-1 antagonist are administered simultaneously, separately, continuously, or at a time interval.

[17-1] The method according to [15] or [16] above, wherein Eribulin or the pharmaceutically acceptable salt thereof is Eribulin mesylate.

[17-2] The method according to [17-1] above, wherein Eribulin mesylate is administered at 0.5 to 3 mg/m$^2$ (body surface area) once in 1 week, 2 weeks or 3 weeks.

[17-3] The method according to [17-1] above, wherein Eribulin mesylate is administered at 0.5 to 2 mg/m$^2$ (body surface area) once in 1 week, 2 weeks or 3 weeks.

[17-4] The method according to [17-1] above, wherein Eribulin mesylate is administered at about 1.5 mg/m$^2$ (body surface area) once in 1 week, 2 weeks or 3 weeks.

[17-5] The method according to [17-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[18] The method according to any of [15] to [17-5] above, wherein the PD-1 antagonist is an anti-PD-1 antibody.

[19-1] The method according to [18] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[19-2] The method according to [18] above, wherein the anti-PD-1 antibody is selected from the group consisting of Nivolumab, Pembrolizumab, Cemiplimab, Sintilimab, and Toripalimab.

[19-3] The method according to [18] above, wherein the anti-PD-1 antibody is Nivolumab.

[19-4] The method according to [19-3] above, wherein Nivolumab is administered at 3 mg/kg (body weight) every 2 weeks, at 240 mg every 2 weeks, at 360 mg every 3 weeks or at 480 mg every 4 weeks.

[19-5] The method according to [18] above, wherein the anti-PD-1 antibody is Pembrolizumab.

[19-6] The method according to [19-5] above, wherein Pembrolizumab is administered at 200 mg every 3 weeks or at 400 mg every 6 weeks.

[19-7] The method according to [18] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[19-8] The method according to [18] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m² (body surface area) and Nivolumab is intravenously administered at 240 mg on days 1 and 15 of a 28-day cycle.

[20-1] The method according to any of [15] to [19-8] above, wherein the tumor is breast cancer, gastric cancer, esophageal cancer, small cell lung cancer, colorectal cancer, renal cancer, thymic carcinoma or intrahepatic cholangiocarcinoma.

[20-2] The method according to any of [15] to [19-8] above, wherein the tumor is breast cancer, gastric cancer, esophageal cancer, small cell lung cancer, colorectal cancer or renal cancer.

[20-3] The method according to any of [15] to [19-8] above, wherein the tumor is breast cancer.

[20-4] The method according to any of [15] to [19-8] above, comprising administering to a patient with advanced, unresectable, or recurrent solid tumors without standard therapy or another effective therapy.

[20-5] The method according to any of [15] to [19-8] above, comprising administering to a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[20-6] The method according to any of [15] to [19-8] above, comprising administering to a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[21] Use of Eribulin or a pharmaceutically acceptable salt thereof in the manufacture of a pharmaceutical composition for treating tumor, wherein the pharmaceutical composition is administered in combination with a PD-1 antagonist.

[22] Use of a PD-1 antagonist in the manufacture of a pharmaceutical composition for treating tumor, wherein the pharmaceutical composition is administered in combination with a liposomal composition comprising Eribulin or a pharmaceutically acceptable salt thereof.

[23] The use according to [21] or [22] above, wherein the liposomal composition comprising Eribulin or a pharmaceutically acceptable salt thereof and the PD-1 antagonist are administered simultaneously, separately, continuously, or at a time interval.

[24-1] The use according to any of [21] to [23] above, wherein Eribulin or the pharmaceutically acceptable salt thereof is Eribulin mesylate.

[24-2] The use according to [24-1] above, wherein Eribulin mesylate is administered at 0.5 to 3 mg/m² (body surface area) once in 1 week, 2 weeks or 3 weeks.

[24-3] The use according to [24-1] above, wherein Eribulin mesylate is administered at 0.5 to 2 mg/m² (body surface area) once in 1 week, 2 weeks or 3 weeks.

[24-4] The use according to [24-1] above, wherein Eribulin mesylate is administered at about 1.5 mg/m² (body surface area) once in 1 week, 2 weeks or 3 weeks.

[24-5] The use according to [24-1] above, wherein Eribulin mesylate is intravenously administered at 0.5 to 1.4 mg/m² (body surface area) or 0.5 to 3.0 mg/m² (body surface area) on day 1 of a 21-day cycle or is intravenously administered at 0.5 to 1.5 mg/m² (body surface area) or 0.5 to 3.0 mg/m² (body surface area) on days 1 and 15 of a 28-day cycle.

[25] The use according to any of [21] to [24-5] above, wherein the PD-1 antagonist is an anti-PD-1 antibody.

[26-1] The use according to [25] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[26-2] The use according to [25] above, wherein the anti-PD-1 antibody is selected from the group consisting of Nivolumab, Pembrolizumab, Cemiplimab, Sintilimab, and Toripalimab.

[26-3] The use according to [25] above, wherein the anti-PD-1 antibody is Nivolumab.

[26-4] The use according to [26-3] above, wherein Nivolumab is administered at 3 mg/kg (body weight) every 2 weeks, at 240 mg every 2 weeks, at 360 mg every 3 weeks or at 480 mg every 4 weeks.

[26-5] The use according to [25] above, wherein the anti-PD-1 antibody is Pembrolizumab.

[26-6] The use according to [26-5] above, wherein Pembrolizumab is administered at 200 mg every 3 weeks or at 400 mg every 6 weeks.

[26-7] The use according to [25] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m² (body surface area) and Nivolumab is intravenously administered at 360 mg on day 1 of a 21-day cycle.

[26-8] The use according to [25] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m² (body surface area) and Nivolumab is intravenously administered at 240 mg on days 1 and 15 of a 28-day cycle.

[27-1] The use according to any of [21] to [26-8] above, wherein the tumor is breast cancer, gastric cancer, esophageal cancer, small cell lung cancer, colorectal cancer, renal cancer, thymic carcinoma or intrahepatic cholangiocarcinoma.

[27-2] The use according to any of [21] to [26-8] above, wherein the tumor is breast cancer, gastric cancer, esophageal cancer, small cell lung cancer, colorectal cancer or renal cancer.

[27-3] The use according to any of [21] to [26-8] above, wherein the tumor is breast cancer.

[27-4] The use according to any of [21] to [26-8] above, for a patient with advanced, unresectable, or recurrent solid tumors without standard therapy or another effective therapy.

[27-5] The use according to any of [21] to [26-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[27-6] The use according to any of [21] to [26-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[28] A liposomal composition comprising Eribulin or a pharmaceutically acceptable salt thereof for use in tumor treatment, wherein the liposomal composition is administered in combination with a PD-1 antagonist.

[29] A PD-1 antagonist for use in tumor treatment, wherein the PD-1 antagonist is administered in combination with a liposomal composition comprising Eribulin or a pharmaceutically acceptable salt thereof.

[30] The liposomal composition or PD-1 antagonist for use according to [28] or [29] above, wherein the liposomal composition comprising Eribulin or a pharmaceutically acceptable salt thereof and the PD-1 antagonist are administered simultaneously, separately, continuously, or at a time interval.

[31-1] The liposomal composition or PD-1 antagonist for use according to any of [28] to [30] above, wherein Eribulin or the pharmaceutically acceptable salt thereof is Eribulin mesylate.

[31-2] The liposomal composition or PD-1 antagonist for use according to [31-1] above, wherein Eribulin mesylate is administered at 0.5 to 3 mg/m$^2$ (body surface area) once in 1 week, 2 weeks or 3 weeks.

[31-3] The liposomal composition or PD-1 antagonist for use according to [31-1] above, wherein Eribulin mesylate is administered at 0.5 to 2 mg/m$^2$ (body surface area) once in 1 week, 2 weeks or 3 weeks.

[31-4] The liposomal composition or PD-1 antagonist for use according to [31-1] above, wherein Eribulin mesylate is administered at about 1.5 mg/m$^2$ (body surface area) once in 1 week, 2 weeks or 3 weeks.

[31-5] The liposomal composition or PD-1 antagonist for use according to [31-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[32] The liposomal composition or PD-1 antagonist for use according to any of [28] to [31-5] above, wherein the PD-1 antagonist is an anti-PD-1 antibody.

[33-1] The liposomal composition or PD-1 antagonist for use according to [32] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[33-2] The liposomal composition or PD-1 antagonist for use according to [32] above, wherein the anti-PD-1 antibody is selected from the group consisting of Nivolumab, Pembrolizumab, Cemiplimab, Sintilimab, and Toripalimab.

[33-3] The liposomal composition or PD-1 antagonist for use according to [32] above, wherein the anti-PD-1 antibody is Nivolumab.

[33-4] The liposomal composition or PD-1 antagonist for use according to [33-3] above, wherein Nivolumab is administered at 3 mg/kg (body weight) every 2 weeks, at 240 mg every 2 weeks, at 360 mg every 3 weeks or at 480 mg every 4 weeks.

[33-5] The liposomal composition or PD-1 antagonist for use according to [32] above, wherein the anti-PD-1 antibody is Pembrolizumab.

[33-6] The liposomal composition or PD-1 antagonist for use according to [33-5] above, wherein Pembrolizumab is administered at 200 mg every 3 weeks or at 400 mg every 6 weeks.

[33-7] The liposomal composition or PD-1 antagonist for use according to [32] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[33-8] The liposomal composition or PD-1 antagonist for use according to [32] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[34-1] The liposomal composition or PD-1 antagonist for use according to any one of [28] to [33-8] above, wherein the tumor is breast cancer, gastric cancer, esophageal cancer, small cell lung cancer, colorectal cancer, renal cancer, thymic carcinoma or intrahepatic cholangiocarcinoma.

[34-2] The liposomal composition or PD-1 antagonist for use according to any one of [28] to [33-8] above, wherein the tumor is breast cancer, gastric cancer, esophageal cancer, small cell lung cancer, colorectal cancer or renal cancer.

[34-3] The liposomal composition or PD-1 antagonist for use according to any one of [28] to [33-8] above, wherein the tumor is breast cancer.

[34-4] The liposomal composition or PD-1 antagonist for use according to any of [28] to [33-8] above, for a patient with advanced, unresectable, or recurrent solid tumors without standard therapy or another effective therapy.

[34-5] The liposomal composition or PD-1 antagonist for use according to any of [28] to [33-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[34-6] The liposomal composition or PD-1 antagonist for use according to any of [28] to [33-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[35] A kit for treating tumor, comprising a formulation comprising a liposomal composition comprising Eribulin or a pharmaceutically acceptable salt thereof and a formulation comprising a PD-1 antagonist.

[36] The kit according to [35] above, wherein the liposomal composition comprising Eribulin or a pharmaceutically acceptable salt thereof and the PD-1 antagonist are administered simultaneously, separately, continuously, or at a time interval.

[37-1] The kit according to [35] or [36] above, wherein Eribulin or the pharmaceutically acceptable salt thereof is Eribulin mesylate.

[37-2] The kit according to [37-1] above, wherein Eribulin mesylate is administered at 0.5 to 3 mg/m$^2$ (body surface area) once in 1 week, 2 weeks or 3 weeks.

[37-3] The kit according to [37-1] above, wherein Eribulin mesylate is administered at 0.5 to 2 mg/m$^2$ (body surface area) once in 1 week, 2 weeks or 3 weeks.

[37-4] The kit according to [37-1] above, wherein Eribulin mesylate is administered at about 1.5 mg/m$^2$ (body surface area) once in 1 week, 2 weeks or 3 weeks.

[37-5] The kit according to [37-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[38] The kit according to any of [35] to [37-5] above, wherein the PD-1 antagonist is an anti-PD-1 antibody.

[39-1] The kit according to [38] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[39-2] The kit according to [38] above, wherein the anti-PD-1 antibody is selected from the group consisting of Nivolumab, Pembrolizumab, Cemiplimab, Sintilimab, and Toripalimab.

[39-3] The kit according to [38] above, wherein the anti-PD-1 antibody is Nivolumab.

[39-4] The kit according to [39-3] above, wherein Nivolumab is administered at 3 mg/kg (body weight) every 2 weeks, at 240 mg every 2 weeks, at 360 mg every 3 weeks or at 480 mg every 4 weeks.

[39-5] The kit according to [38] above, wherein the anti-PD-1 antibody is Pembrolizumab.

[39-6] The kit according to [39-5] above, wherein Pembrolizumab is administered at 200 mg every 3 weeks or at 400 mg every 6 weeks.

[39-7] The kit according to [38] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[39-8] The kit according to [38] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[40-1] The kit according to any of [35] to [39-8] above, wherein the tumor is breast cancer, gastric cancer, esophageal cancer, small cell lung cancer, colorectal cancer, renal cancer, thymic carcinoma or intrahepatic cholangiocarcinoma.

[40-2] The kit according to any of [35] to [39-8] above, wherein the tumor is breast cancer, gastric cancer, esophageal cancer, small cell lung cancer, colorectal cancer or renal cancer.

[40-3] The kit according to any of [35] to [39-8] above, wherein the tumor is breast cancer.

[40-4] The kit according to any of [35] to [39-8] above, for a patient with advanced, unresectable, or recurrent solid tumors without standard therapy or another effective therapy.

[40-5] The kit according to any of [35] to [39-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[40-6] The kit according to any of [35] to [39-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[41] The pharmaceutical composition according to any of [1] to [7-6] above or therapeutic agent according to any of [8] to [14-6] above, further comprising a pharmaceutically acceptable carrier.

[42] A therapeutic agent for tumor, wherein a formulation comprising a liposomal composition comprising Eribulin or a pharmaceutically acceptable salt thereof and a formulation comprising a PD-1 antagonist are administered simultaneously, separately, continuously, or at a time interval.

[43-1] The therapeutic agent for tumor according to [42] above, wherein Eribulin or the pharmaceutically acceptable salt thereof is Eribulin mesylate.

[43-2] The therapeutic agent for tumor according to [43-1] above, wherein Eribulin mesylate is administered at 0.5 to 3 mg/m$^2$ (body surface area) once in 1 week, 2 weeks or 3 weeks.

[43-3] The therapeutic agent for tumor according to [43-1] above, wherein Eribulin mesylate is administered at 0.5 to 2 mg/m$^2$ (body surface area) once in 1 week, 2 weeks or 3 weeks.

[43-4] The therapeutic agent for tumor according to [43-1] above, wherein Eribulin mesylate is administered at about 1.5 mg/m$^2$ (body surface area) once in 1 week, 2 weeks or 3 weeks.

[43-5] The therapeutic agent for tumor according to [43-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[44] The therapeutic agent for tumor according to any of [42] to [43-5] above, wherein the PD-1 antagonist is an anti-PD-1 antibody.

[45-1] The therapeutic agent for tumor according to [44] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

[45-2] The therapeutic agent for tumor according to [44] above, wherein the anti-PD-1 antibody is selected from the group consisting of Nivolumab, Pembrolizumab, Cemiplimab, Sintilimab, and Toripalimab.

[45-3] The therapeutic agent for tumor according to [44] above, wherein the anti-PD-1 antibody is Nivolumab.

[45-4] The therapeutic agent for tumor according to [45-3] above, wherein Nivolumab is administered at 3 mg/kg (body weight) every 2 weeks, at 240 mg every 2 weeks, at 360 mg every 3 weeks or at 480 mg every 4 weeks.

[45-5] The therapeutic agent for tumor according to [44] above, wherein the anti-PD-1 antibody is Pembrolizumab.

[45-6] The therapeutic agent for tumor according to [45-5] above, wherein Pembrolizumab is administered at 200 mg every 3 weeks or at 400 mg every 6 weeks.

[45-7] The therapeutic agent for tumor according to [44] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[45-8] The therapeutic agent for tumor according to [44] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[46-1] The therapeutic agent for tumor according to any of [42] to [45-8] above, wherein the tumor is breast cancer, gastric cancer, esophageal cancer, small cell lung cancer, colorectal cancer, renal cancer, thymic carcinoma or intrahepatic cholangiocarcinoma.

[46-2] The therapeutic agent for tumor according to any of [42] to [45-8] above, wherein the tumor is breast cancer, gastric cancer, esophageal cancer, small cell lung cancer, colorectal cancer or renal cancer.

[46-3] The therapeutic agent for tumor according to any of [42] to [45-8] above, wherein the tumor is breast cancer.

[46-4] The therapeutic agent for tumor according to any of [42] to [45-8] above, for a patient with advanced, unresectable, or recurrent solid tumors without standard therapy or another effective therapy.

[46-5] The therapeutic agent for tumor according to any of [42] to [45-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[46-6] The therapeutic agent for tumor according to any of [42] to [45-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[47] A combination for treating tumor comprising a liposomal composition comprising Eribulin or a pharmaceutically acceptable salt thereof, and a PD-1 antagonist.

[48] The combination according to [47] above, wherein the liposomal composition comprising Eribulin or a pharmaceutically acceptable salt thereof and the PD-1 antagonist are administered simultaneously, separately, continuously, or at a time interval.

[49-1] The combination according to [48] to [49] above, wherein Eribulin or the pharmaceutically acceptable salt thereof is Eribulin mesylate.

[49-2] The combination according to [49-1] above, wherein Eribulin mesylate is administered at 0.5 to 3 mg/m$^2$ (body surface area) once in 1 week, 2 weeks or 3 weeks.

[49-3] The combination according to [49-1] above, wherein Eribulin mesylate is administered at 0.5 to 2 mg/m$^2$ (body surface area) once in 1 week, 2 weeks or 3 weeks.

[49-4] The combination according to [49-1] above, wherein Eribulin mesylate is administered at about 1.5 mg/m$^2$ (body surface area) once in 1 week, 2 weeks or 3 weeks.

[49-5] The combination according to [49-1] above, wherein Eribulin mesylate is intravenously administered at 0.5 to 1.4 mg/m$^2$ (body surface area) or 0.5 to 3.0 mg/m$^2$ (body surface area) on day 1 of a 21-day cycle or is intravenously administered at 0.5 to 1.5 mg/m$^2$ (body surface area) or 0.5 to 3.0 mg/m$^2$ (body surface area) on days 1 and 15 of a 28-day cycle.

[50] The combination according to any of [47] to [49-5] above, wherein the PD-1 antagonist is an anti-PD-1 antibody.

[51-1] The combination according to [50] above, wherein the anti-PD-1 antibody is selected from the group consisting of Nivolumab, Pembrolizumab, Cemiplimab, Sintilimab, Toripalimab, Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZMO09, CMAB819, Sym021, SSI-361, JY034, HX008, ISU106 and CX-188.

[51-2] The combination according to [50] above, wherein the anti-PD-1 antibody is selected from the group consisting of Nivolumab, Pembrolizumab, Cemiplimab, Sintilimab, and Toripalimab.

[51-3] The combination according to [50] above, wherein the anti-PD-1 antibody is Nivolumab.

[51-4] The combination according to [51-3] above, wherein Nivolumab is administered at 3 mg/kg (body weight) every 2 weeks, at 240 mg every 2 weeks, at 360 mg every 3 weeks or at 480 mg every 4 weeks.

[51-5] The combination according to [50] above, wherein the anti-PD-1 antibody is Pembrolizumab.

[51-6] The combination according to [51-5] above, wherein Pembrolizumab is administered at 200 mg every 3 weeks or at 400 mg every 6 weeks.

[51-7] The combination according to [50] above, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[51-8] The combination according to [50] above, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

[52-1] The combination according to any of [47] to [51-8] above, wherein the tumor is breast cancer, gastric cancer, esophageal cancer, small cell lung cancer, colorectal cancer, renal cancer, thymic carcmoma or intrahepatic cholangiocarcinoma.

[52-2] The combination according to any of [47] to [51-8] above, wherein the tumor is breast cancer, gastric cancer, esophageal cancer, small cell lung cancer, colorectal cancer or renal cancer.

[52-3] The combination according to any of [47] to [51-8] above, wherein the tumor is breast cancer.

[52-4] The combination according to any of [47] to [51-8] above, for a patient with advanced, unresectable, or recurrent solid tumors without standard therapy or another effective therapy.

[52-5] The combination according to any of [47] to [51-8] above, for a patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer, wherein the patient is a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy.

[52-6] The combination according to any of [47] to [51-8] above, for a patient with intrahepatic cholangiocarcinoma administered with a combination therapy of Gemcitabine and Cisplatin as a primary therapy and a combination therapy of S-1 and Resminostat as a secondary therapy for a prior treatment, or for a patient with thymic carcinoma administered with a combination therapy of Carboplatin and Paclitaxel as a primary therapy, S-1 as a secondary therapy and Gemcitabine as a tertiary therapy for a prior treatment.

[53-1] A method for treating tumor, comprising administering a liposomal composition comprising Eribulin or a pharmaceutically acceptable salt thereof and a PD-1 antagonist to a patient in need thereof wherein the tumor is gastric cancer, esophageal cancer, lung cancer, thymic carcinoma or biliary tract cancer.

[53-2] The method of [53-1], wherein the lung cancer is small cell lung cancer or non-small cell lung cancer.

[53-3] The method of [53-1], wherein the biliary tract cancer is intrahepatic cholangiocarcinoma.

[53-4] The method of any one of [53-1] to [53-3], wherein the liposomal composition comprising Eribulin or the pharmaceutically acceptable salt thereof and the PD-1 antagonist are administered simultaneously, separately, continuously, or at a time interval.

[53-5] The method of any one of [53-1] to [53-4], wherein Eribulin or the pharmaceutically acceptable salt thereof is Eribulin mesylate.

[53-6] The method of any one of [53-1] to [53-5], wherein the PD-1 antagonist is an anti-PD-1 antibody.

[53-7] The method of [53-6], wherein the anti-PD-1 antibody is selected from the group consisting of Nivolumab, Pembrolizumab, Cemiplimab, Sintilimab and Toripalimab.

[53-8] The method of [53-6], wherein the anti-PD-1 antibody is Nivolumab and wherein Nivolumab is administered at 3 mg/kg (body weight) every 2 weeks, at 240 mg every 2 weeks, at 360 mg every 3 weeks or at 480 mg every 4 weeks.

[53-9] The method of [53-6], wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

[53-10] The method of [53-6], wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

Advantageous Effects of Invention

The combined administration of a liposomal composition comprising Eribulin or a pharmaceutically acceptable salt thereof and a PD-1 antagonist exhibits unexpected antitumor effect.

DESCRIPTION OF EMBODIMENTS

Figure 1:
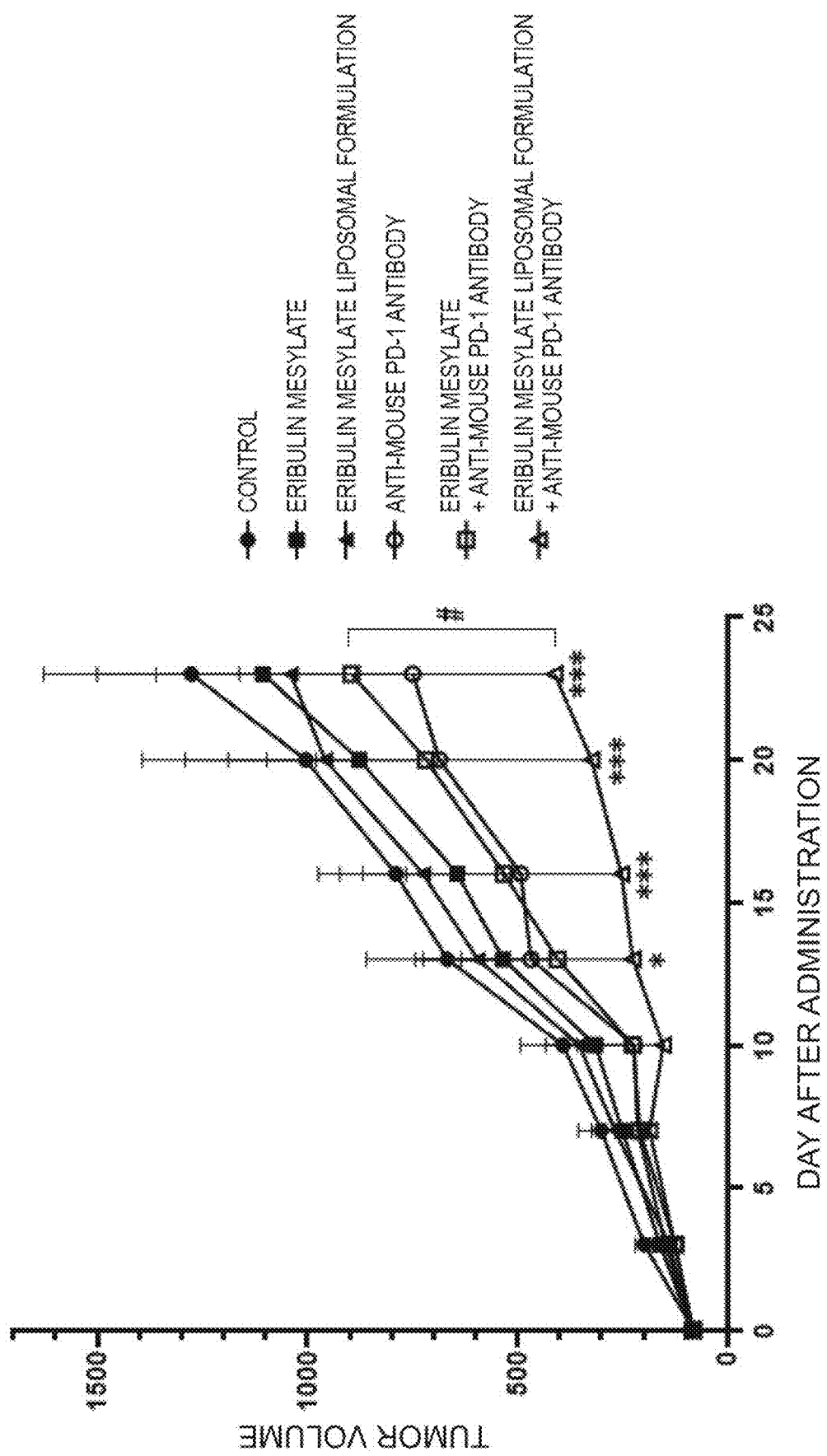
FIG. 1 is a graph illustrating effect of treatment with a combination of a liposomal formulation comprising Eribulin mesylate at a dose of 0.1 mg/kg and an anti-PD-1 antibody on tumor growth.

Embodiments of the present disclosure will be described below. The following embodiments are illustrations for the purpose of describing the present disclosure and not intended to limit the present disclosure only to these embodiments. The present disclosure can be carried out in various forms, unless they deviate from its spirit.

The liposomal compositions in the present disclosure comprises Eribulin or a pharmaceutically acceptable salt thereof (hereinafter referred to as "Eribulin or the like").

In the present disclosure, the "pharmaceutically acceptable salt" may be either an inorganic acid salt or an organic acid salt and is not particularly limited, as long as it forms a salt with Eribulin, and examples thereof include hydrochloride, sulfate, citrate, hydrobromide, hydroiodide, nitrate, bisulfate, phosphate, superphosphate, isonicotinate, acetate, lactate, salicylate, tartrate, pantothenate, ascorbate, succinate, maleate, fumarate, gluconate, saccharinate, formate, benzoate, glutamate, mesylate (methanesulfonate), ethanesulfonate, benzenesulfonate, p-toluenesulfonate, and pamoate. In one embodiment, the pharmaceutically acceptable salts are hydrochloride, sulfate, acetate, phosphate, citrate, and mesylate. In a particular embodiment, the pharmaceutically acceptable salt is mesylate.

The pharmaceutically acceptable salt of Eribulin may be a salt of Eribulin and aluminum, calcium, lithium, magnesium, sodium, zinc, or diethanolamine.

In the present disclosure, examples of Eribulin or the like include Eribulin mesylate.

Eribulin or the like is a compound or a salt thereof described in Patent Literature 1 or U.S. Pat. No. 6,214,865 and has pharmacological activities including antitumor and antimitotic activities. Patent Literature 1 discloses that Eribulin or the like has, as an antitumor agent, anti-tumor activity against melanoma, fibrosarcoma, monocytic leukemia, colon cancer, ovarian cancer, breast cancer, osteosarcoma, prostate cancer, lung cancer, and ras-transformed fibroblasts. Eribulin or the like is obtained by a method of production described in Patent Literatures 1 to 3.

In the present disclosure, the "liposome" means a closed microvesicle having an inner phase surrounded by a lipid bilayer. The liposomes include small unilamellar liposomes (SUVs small unilamellar vesicles), large unilamellar liposomes (LUVs: large unilamellar vesicles), further large unilamellar liposomes (GUVs: giant unilamellar vesicles), multi-lamellar liposomes having a plurality of concentric membranes (MLVs: multi lamellar vesicles), liposomes having a plurality of non-concentric, irregular membranes (MVVs: multivesicular vesicles), and the like.

In the present disclosure, the "liposomal inner phase" means an aqueous region surrounded by a liposomal lipid bilayer and is used synonymously with an "inner aqueous phase" and a "liposomal inner aqueous phase". The "liposomal outer phase" means a region that is not surrounded by a liposomal lipid bilayer (that is, the region except the inner phase and the lipid bilayer) when the liposome is dispersed in a liquid.

In the present disclosure, the "liposomal composition" means a composition comprising a liposome and further comprising Eribulin or the like in the liposomal inner phase.

In the present disclosure, the liposomal composition includes solid and liquid compositions.

In the present disclosure, the "liposomal dispersion liquid" means a composition comprising a liposome in which Eribulin or the like is not yet encapsulated into the liposomal inner phase.

In the present disclosure, the "liposomal preparatory liquid" means a composition comprising a liposome in which an adjustment of the liposome outer phase in order to encapsulate Eribulin or the like into the liposome inner phase is not yet performed.

[Lipid]

In one embodiment, the liposome preferably comprises a phospholipid and/or phospholipid derivative as a membrane component.

Examples of the phospholipid and/or phospholipid derivative include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerolphosphate, 1,2-dimyristoyl-1,2-deoxyphosphatidyl choline, plasmalogen, and phosphatidate.

The phospholipid and/or phospholipid derivative may be one or a combination of two or more of these.

Fatty acid residues in the phospholipid and/or phospholipid derivative are not particularly limited, and examples thereof include saturated or unsaturated fatty acid residues having 12 to 20 carbon atoms, and specific examples thereof include acyl groups derived from fatty acids such as lauric acid, myristic acid, palmitic acid, stearic acid, oleic acid, and linoleic acid. As the phospholipid and/or phospholipid derivative, a phospholipid derived from a natural product such as egg yolk lecithin and soy lecithin, and partially hydrogenated egg yolk lecithin, (fully) hydrogenated egg yolk lecithin, partially hydrogenated soy lecithin, and (fully) hydrogenated soy lecithin, in which unsaturated fatty acid residues are partially or fully hydrogenated, or the like may be used.

The blending amount (molar fraction) of the phospholipid and/or phospholipid derivative, used in the preparation of the liposome is not particularly limited, and is, in one embodiment, 10 to 80% and, in a particular embodiment, 30 to 60% based on the total ribosomal membrane components.

In the present disclosure, the liposome may comprise, as a membrane component, a sort of sterol such as cholesterol and cholestanol and a sort of fatty acid having a saturated or unsaturated acyl group having 8 to 22 carbon atoms as a membrane stabilizing agent, and an antioxidant such as α-tocopherol, besides the phospholipid and/or phospholipid derivative.

The blending amount (molar fraction) of the sterol, used in the preparation of the liposome is not particularly limited, and is, in one embodiment, 1 to 60%, 10 to 50%, or 30 to 50% based on the total liposomal membrane components.

The blending amount (molar fraction) of the fatty acid is not particularly limited, and is, in one embodiment, 0 to 30%, 0 to 20% or 0 to 10% based on the total liposomal membrane components.

The blending amount (molar fraction) of the antioxidant is not particularly limited, as long as an amount that provides the antioxidant effect is added, and it is, in one embodiment, 0 to 15%, 0 to 10%, or 0 to 5% based on the total liposomal membrane components.

In the present disclosure, the liposome may comprise a functional lipid or a modified lipid as a membrane component.

Examples of the functional lipid include a blood-retaining lipid derivative, a temperature change-sensitive lipid derivative, and a pH-sensitive lipid derivative.

Examples of the modified lipid include a PEGylated lipid, a glycolipid, an antibody-modified lipid, and a peptide-modified lipid.

Examples of the blood-retaining lipid derivative include polyethylene glycol derivatives (such as methoxy polyethylene glycol condensates) such as condensation products of phosphoethanolamine and methoxy polyethylene glycol: N-{carbonyl-methoxy polyethylene glycol-2000}-1,2-dipalmitoyl-sn-glycero-3-phosphoethanolamine, N-{carbonyl-methoxy polyethylene glycol-5000}-1,2-dipalmitoyl-sn-glycero-3-phosphoethanolamine, N-{carbonyl-methoxy polyethylene glycol-750}-1,2-distearoyl-sn-glycero-3-phosphoethanolamine, N-{carbonyl-methoxy polyethylene glycol-2000}-1,2-distearoyl-sn-glycero-3-phosphoethanolamine, (MPEG2000-distearoylphosphatidylethanolamine), and N-{carbonyl-methoxy polyethylene glycol-5000}-1,2-distearoyl-sn-glycero-3-phosphoethanolamine.

The blending amount (molar fraction) of the blood-retaining lipid derivative, used in the preparation of the liposome, is not particularly limited, and is, in one embodiment, 0 to 50%, 0 to 30%, or 0 to 20% based on the total liposomal membrane components.

Examples of the temperature change-sensitive lipid derivative include dipalmitoylphosphatidylcholine. By including the temperature change-sensitive lipid derivative in a liposome, it becomes possible to disrupt the liposome at a particular temperature, to change the surface properties of the liposome, and the like. Furthermore, by combining it with heating of a target site such as tumor, it becomes possible to disrupt the liposome at the target site and have an active compound released at the target site, and the like.

Examples of the pH-sensitive lipid derivative include dioleoylphosphatidylethanolamine By including the pH-sensitive lipid derivative in a liposome, it becomes possible to promote membrane fusion of the liposome and an endosome when the liposome is taken in a cell by endocytosis and improve the delivery of the active compound to the cytoplasm, and the like.

Examples of the glycolipid, antibody-modified lipid, and peptide-modified lipid include lipids linked to a sugar, an antibody, or a peptide having an affinity for a target cell or a target tissue. Using a modified lipid allows to deliver the liposome actively to the target cell or the target tissue.

The composition of membrane components for liposome having a practically acceptable level of membrane permeability can be set by a person skilled in the art as appropriate depending on the active compound, the target tissue, and the like (see Hiroshi Kikuchi et al. "Liposome I—How to prepare and assay—" Cell technology (1983) 2 (9): pp. 1136-1149 and the references cited in the reference, and the like). The liposomal composition may be used not only in targeting at a target tissue such as solid cancer, but also in the delivery of an active compound to blood cancer or the like.

The liposomal membrane components include, in one embodiment, phospholipid, cholesterol, and a methoxy polyethylene glycol condensation product.

[Liposomal Composition]

In the liposomal composition in the present disclosure, Eribulin or the like is encapsulated in a liposome having a lipid membrane. In the liposomal composition, Eribulin or the like may be distributed in the lipid bilayer.

The liposomal composition according to the present disclosure can be obtained by a method described in Patent Literature 7.

If the liposomal composition is solid, it may be dissolved or suspended in a certain solvent described below to prepare a liquid liposomal composition. If the liposomal composition is in the form of frozen solid, it may be thawed by leaving it at room temperature or the like to prepare a liquid liposomal composition.

The liposomal composition according to the present disclosure is not limited, as long as it comprises (1) Eribulin or the like. The liposomal composition according to the present disclosure may further comprise (2) at least one ammonium salt and (3) at least one acid, salt, base, and/or amino acid.

Examples of at least one ammonium salt in (2) include ammonium chloride, ammonium borate, ammonium sulfate, ammonium formate, ammonium acetate, ammonium citrate, ammonium tartrate, ammonium succinate, and ammonium phosphate and, one embodiment thereof is ammonium sulfate, ammonium citrate, and ammonium tartrate.

As for the acid, salt, base, and/or amino acid in (3), examples of the acid include ascorbic acid, benzoic acid, succinic acid, citric acid, glutamic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; examples of the salt include sodium salts of the aforementioned acids, potassium salts of the aforementioned acids, and ammonium salts of the aforementioned acids; examples of the base include trishydroxymethylaminomethane, ammonia, sodium hydroxide, and potassium hydroxide; and examples of the amino acid include arginine, histidine, and glycine.

In one embodiment of the liposomal composition according to the present disclosure, the acid, salt, base, and/or amino acid of (3) in the liposomal inner phase is hydrochloric acid, acetic acid, lactic acid, tartaric acid, succinic acid, citric acid, and phosphoric acid, sodium salts of the aforementioned acids, and sodium hydroxide and ammonia, and, in a particular embodiment, the acid, salt, base, and/or amino acid in (3) is acetic acid, lactic acid, tartaric acid, citric acid, and phosphoric acid, sodium salts of the aforementioned acids, and sodium hydroxide and ammonia.

An example of each component of the liposomal composition is set forth in Table 1. In another specific example, 96 mg/mL sucrose may be used, instead of 9 mg/mL sodium chloride, as an osmotic agent (liposomal outer phase).

TABLE 1

| Component | Concentration | Purpose of inclusion |
| --- | --- | --- |
| Eribulin mesylate | 0.2 mg/mL | Drug |
| HSPC[1] | 7.1 mg/mL | Lipid membrane component |
| Cholesterol | 2.3 mg/mL | Lipid membrane component |
| MPEG2000-DSPE[2] | 2.7 mg/mL | Lipid membrane component |
| Ammonium sulfate | 100 mM | Liposomal inner phase component |
| Citric acid monohydrate | 30 mM | Liposomal inner phase component |
| Sodium chloride | 9 mg/mL | Liposomal outer phase component |
| L-histidine | 1.6 mg/mL | Liposomal outer phase component |
| Sodium hydroxide/hydrochloric acid | q.s. | pH adjuster |

[1]Hydrogenated soy phosphatidylcholine
[2]N-{carbonyl-methoxy polyethylene glycol-2000}-1,2-distearoyl-sn-glycero-3-phosphoethanolamine (MPEG2000-distearoylphosphatidylethanolamine)

TABLE 2

| Component | Concentration | Purpose of inclusion |
| --- | --- | --- |
| Eribulin mesylate | 0.20 mg/mL | Drug |
| HSPC[1] | 7.10 mg/mL | Lipid membrane component |
| Cholesterol | 2.32 mg/mL | Lipid membrane component |
| MPEG2000-DSPE[2] | 2.69 mg/mL | Lipid membrane component |
| Ammonium sulfate | 100 mM | Liposomal inner phase component |
| Citric acid monohydrate | 30 mM | Liposomal inner phase component |
| Sucrose | 96 mg/mL | Liposomal outer phase component |
| L-histidine | 1.55 mg/mL | Liposomal outer phase component |
| Sodium hydroxide/hydrochloric acid | q.s. | pH adjuster |

[1]Hydrogenated soy phosphatidylcholine
[2]N-{carbonyl-methoxy polyethylene glycol-2000}-1,2-distearoyl-sn-glycero-3-phosphoethanolamine (MPEG2000-distearoylphosphatidylethanolamine)

The liposomal composition according to the present disclosure may be administered by injection (intravenous injection, intraarterial injection, topical injection), orally, nasally, transdermally, transpulmonarily, ophthalmically, and the like, and examples thereof include injection such as intravenous injection, subcutaneous injection, intradermal injection, intraarterial injection, as well as topical injection to a target cell and organ. Examples of the dosage form of the liposomal composition for oral administration include tablets, powders, granules, syrups, capsules, and oral solutions. Examples of the dosage form of the liposomal composition for parenteral administration include an injection, drip infusion, ophthalmic liquid, ointment, suppository, suspension, cataplasm, lotion, aerosol, and plaster, and one embodiment thereof is the injection or drip infusion. The liposomal composition according to the present disclosure may be formulated by a method, for example, described in Japanese Pharmacopoeia (JP) 17th edition, United States Pharmacopoeia (USP), or European pharmacopoeia (EP).

If the liposomal composition is a liquid formulation, it may be used as it is. If using the liposomal composition as a medicine, for example, a physician or a patient may inject a solvent into a vial in which a solid formulation is encapsulated to prepare upon use. If a solid formulation obtained by freezing a liquid liposomal composition, it may be stored in a frozen state and thawed by leaving at room temperature or thawed rapidly with heating back into a liquid upon use to be used as a liquid formulation.

The dose upon administration of the liposomal composition alone vary markedly depending on the kind of target disease, or the age, sex, body weight, the severity of symptoms, or the like of the patient. The liposomal composition is administered, for example, at 0.1 to 10 mg/m² (body surface) in terms of Eribulin mesylate per day for an adult. In one embodiment, the liposomal composition is administered at a dose of 0.5 to 3 mg/m² (body surface) in terms of Eribulin mesylate once every 1 week, 2 weeks, or 3 weeks. In a particular embodiment, the liposomal composition is more preferably administered at a dose of 0.5 to 2 mg/m² (body surface) in terms of Eribulin mesylate once every 1 week, 2 weeks, or 3 weeks.

In another embodiment, the liposomal composition is preferably administered at a dose of approximately 1.5 mg/m² (body surface) in terms of Eribulin mesylate once every 1 week, 2 weeks, or 3 weeks.

More specifically, the liposomal composition is administered intravenously at 0.5 to 1.4 mg/m² or 0.5 to 3.0 mg/m² on day 1 of a 21-day cycle or administered intravenously at 0.5 to 1.5 mg/m² or 0.5 to 3.0 mg/m² on day 1 and day 15 of a 28-day cycle in terms of Eribulin mesylate.

Eribulin or the like contained in the liposomal composition may be administered once a day or in several divided daily doses.

The liposomal composition may be a liposomal composition comprising, for example, 0.01 to 300 mg/mL of Eribulin or the like in the liposomal inner phase.

The liposomal composition is formulated, for example, as an injection comprising 0.20 mg/mL Eribulin mesylate (0.18 mg/mL Eribulin) incorporated in a liposome having a lipid membrane consisting of HSPC, cholesterol, and MPEG2000-DSPE. Such an injection may comprise sucrose or sodium chloride as an isotonizing agent, ammonium sulfate, citric acid, and L-histidine, and sodium hydroxide and hydrochloric acid to adjust pH. The injection is directly administered to a patient or diluted with physiological saline to be at the concentration range of 0.0035 mg/mL or higher and lower than 0.2 mg/mL before administration to a patient.

The PD-1 antagonist in the present disclosure may comprise any compound or biological molecule that blocks the binding of PD-L1 expressed in cancer cells to PD-1 expressed in immune cells (T cells, B cells, or natural killer T (NKT) cells), or further blocks the binding of PD-L2 expressed in cancer cells to PD-1 expressed in immune cells. The PD-1 antagonist blocks the binding of human PD-L1 to human PD-1 and, in one embodiment, blocks the binding of both human PD-L1 and PD-L2 to human PD-1. The amino acid sequence of human PD-1 can be found in NCBI Locus No.: NP 005009. The amino acid sequences of human PD-L1 and PD-L2 can be found in NCBI Locus No: NP_054862 and NP_079515, respectively.

The PD-1 antagonist useful in the present disclosure may comprise a monoclonal antibody (mAb) or an antigen-binding fragment thereof that specifically binds to PD-1 or PD-L1 or specifically binds to human PD-1 or human PD-L1. The mAb may be a human antibody, humanized antibody, or chimeric antibody, and may comprise a human constant region. The human constant region is selected from the group consisting of IgG1, IgG2, IgG3, and IgG4 constant regions and, in one embodiment, the human constant region is an IgG1 or IgG4 constant region. The antigen-binding fragment may be selected from the group consisting of Fab, Fab'-SH, F(ab')$_2$, scFv, and Fv fragment.

An example of useful PD-1 antagonists is an anti-PD-1 antibody, which is, in one embodiment, an anti-human PD-1 antibody and, in a particular embodiment, an anti-human PD-1 monoclonal antibody (anti-human PD-1 mAb). Examples of the human PD-1-binding mAb binding are described in U.S. Pat. Nos. 7,488,802, 7,521,051, 8,008,449, 8,354,509, 8,168,757, WO 2004/004771, WO 2004/072286, WO 2004/056875, and US Patent Application Publication No. 2011/0271358. Anti-human PD-1 monoclonal antibodies to be useful as the PD-1 antagonist according to the present disclosure include Nivolumab, Pembrolizumab, Cemiplimab, Sintilimab, and Toripalimab. Anti-PD-1 antibodies to be useful as the PD-1 antagonist according to the present disclosure further include Spartalizumab, Tislelizumab, Dostarlimab, Camrelizumab, Genolimzumab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM388D4, ENUM244C8, GLS010, CS1003, BAT-1306, AK103, BI754091, LZM009, CMAB819, Sym021, SSI-361, JY034, HX008, ISU106 and CX-188.

Another example of useful PD-1 antagonists is an anti-PD-L1 antibody, which is, in one embodiment, an anti-human PD-L1 antibody and, in a particular embodiment, an anti-human PD-L 1 monoclonal antibody (anti-human PD-L1 mAb). Anti-PD-L1 antibodies to be useful as the PD-1 antagonist according to the present disclosure include Atezolizumab, Avelumab, Durvalumab, Manelimab, Pacmilimab, Envafolimab, Cosibelimab, BMS-936559, STI-1014, KNO35, LY3300054, HLX20, SHR-1316, CS1001, MSB2311, BGB-A333 and KL-A16.

The PD-1 antagonist according to the present disclosure may be administered by injection (intravenous injection, intraarterial injection, topical injection), orally, nasally, transdermally, transpulmonarily, ophthalmically, and the like, and examples thereof include injection such as intravenous injection, subcutaneous injection, intradermal injection, intraarterial injection, as well as topical injection to target cells and organ. Examples of the dosage form of the PD-1 antagonist for oral administration include a tablet, powder, granule, syrup, capsule, and oral solution. Examples of the dosage form of the PD-1 antagonist for parenteral administration include an injection, drip infusion, ophthalmic liquid, ointment, suppository, suspension, cataplasm, lotion, aerosol, and plaster, and one embodiment thereof is the injection or drip infusion. The PD-1 antagonist according to the present disclosure may be formulated by a method, for example, described in Japanese Pharmacopoeia (JP) 17th edition, United States Pharmacopoeia (USP), or European pharmacopoeia (EP).

If the PD-1 antagonist according to the present disclosure is an anti-PD-1 antibody, the anti-PD-1 antibody may be provided as a liquid preparation or prepared by rehydrating its freeze-drying powder with sterile water for injection before use.

Upon administration of an anti-human PD-1 mAb alone as the PD-1 antagonist to a patient, the dose thereof varies markedly depending on the kind of target disease, or the age, sex, body weight, the severity of symptoms, or the like of the patient. The anti-human PD-1 mAb is administered, for example, at a dose of 1, 2, 3, 5, or 10 mg/kg at intervals of approximately 14 days (±2 days), approximately 21 days (±2 days), or approximately 30 days (±2 days).

If Pembrolizumab is administered as the PD-1 antagonist, it is administered intravenously, for example, at a dose selected from the group consisting of 1 mg/kg Q2W, 2 mg/kg Q2W, 3 mg/kg Q2W, 5 mg/kg Q2W, 10 mg of Q2W, 1 mg/kg Q3W, 2 mg/kg Q3W, 3 mg/kg Q3W, 5 mg/kg Q3W, and 10 mg/kg Q3W. In another embodiment, Pembrolizumab is administered intravenously at a dose of 200 mg Q3W or 400 mg Q6W. Pembrolizumab is administered as a liquid medicine comprising, for example, 25 mg/ml Pembrolizumab, 7% (w/v) sucrose, and 0.02% (w/v) polysorbate 80 in a 10 mM histidine buffer, pH 5.5, and the medicine at a selected dose is administered by intravenous drip over a period of approximately 30 minutes.

If Nivolumab is administered as the PD-1 antagonist, it is administered intravenously, for example, at a dose selected from the group consisting of 1 mg/kg Q2W, 2 mg/kg Q2W, 3 mg/kg Q2W, 4 mg/kg Q2W, 5 mg/kg Q2W, 6 mg/kg Q2W, 1 mg/kg Q3W, 2 mg/kg Q3W, 3 mg/kg Q3W, 4 mg/kg Q3W, 5 mg/kg Q3W, 6 mg/kg Q3W, 8 mg/kg Q3W and 10 mg/kg Q3W. In another embodiment, Nivolumab is administered intravenously at a dose of 240 mg Q2W, 360 mg Q3W or 480 mg Q4W. For example, Nivolumab is administered by intravenous drip over a period of approximately 30 minutes or longer as a liquid medicine further comprising D-mannitol, sodium citrate hydrate, sodium chloride, diethylenetriaminepentaacetic acid, polysorbate 80 and a pH-adjusting agent.

If Cemiplimab is administered as the PD-1 antagonist, it is administered intravenously, for example, at a dose of 350 mg Q3W.

The doses of the liposomal composition and the PD-1 antagonist in the combined administration of the present disclosure may usually be set at doses lower than the doses when they are administered alone, respectively. Specific doses, administration routes, administration frequencies, administration cycles and the like are determined as appropriate in consideration of the kind of target disease, or the age, sex, body weight the severity of symptoms, or the like of the patient.

The modes of administration of the liposomal composition and the PD-1 antagonist in the present disclosure are not particularly limited, as long as the liposomal composition and the PD-1 antagonist are administered in combination when administered. For example, the liposomal composition and the PD-1 antagonist are administered to a patient simultaneously, separately, continuously, or at a time interval. Here, "simultaneously" means that each component is administered in the same period of time or strictly simultaneously, or via the same administration route. It also means that each component is administered without substantial interval between the both so as to produce an additive effect, preferably a synergistic effect. "Separately" means that each component is administered at different dose intervals or frequencies, or via different administration routes. "Continuously" means that each component is administered via the same or different administration routes in any order within a certain period of time. "At a time interval" means that each component is administered via the same or different administration routes, with each component being administered at a time interval. If the PD-1 antagonist is administered in a period of 1 cycle of the administration of the liposomal composition or a period in which the cycle is repeated, it is considered that both are administered in combination.

The mode of the combination is not particularly limited, and a person skilled in the art can combine the liposomal composition and the PD-1 antagonist in various ways.

In the case of combining a liposomal composition comprising Eribulin mesylate and Nivolumab, for example, Eribulin mesylate is intravenously administered at 1.7 to 2.1 mg/m$^2$ (body surface area) and Nivolumab is intravenously administered at 360 mg on day 1 of a 21-day cycle, or Eribulin mesylate is intravenously administered at 1.1 to 1.4 mg/m$^2$ (body surface area) and Nivolumab is intravenously administered at 240 mg on days 1 and 15 of a 28-day cycle.

A tumor to be treated in the present disclosure is, for example, breast cancer, gastric cancer, esophageal cancer, lung cancer (small cell lung cancer and non-small cell lung cancer), colorectal cancer, renal cancer, thymic carcinoma, biliary tract cancer (intrahepatic cholangiocarcinoma, extrahepatic cholangiocarcinoma, gallbladder carcinoma and duodenal papilla carcinoma) and the like.

A patients to be treated in the present disclosure is, for example, a patient whose disease has progressed during or after a prior chemotherapy. Examples of the chemotherapy include a platinum-based drug, a fluorinated pyrimidine-based drug, a taxane-based drug, and combinations thereof.

A patient to be treated in the present disclosure is, for example, a patient with advanced, unresectable, or recurrent solid tumors without standard therapy or another effective therapy (a patient receiving Nivolumab monotherapy as standard therapy are eligible). In another embodiment, the patient is a patient with unresectable gastric cancer, esophageal cancer or small cell lung cancer, who has had a definitive diagnosis and whose disease progresses at the physician's discretion during or after a primary chemotherapy (or a secondary chemotherapy for gastric cancer) and who has not received other systemic chemotherapies for advanced or recurrent cancer thereof wherein the patient is also a patient with gastric cancer administered with a combination chemotherapy comprising a platinum-based drug and a fluorinated pyrimidine-based drug as a primary chemotherapy and a chemotherapy comprising a taxane-based drug as a secondary chemotherapy, a patient with esophageal cancer administered with a combination chemotherapy comprising a platinum-based drug and a fluorinated pyrimidine-based drug (but not comprising a taxane-based drug) as a primary chemotherapy, or a patient with small cell lung cancer administered with a combination chemotherapy comprising a platinum-based drug as a primary chemotherapy. More specifically, the patient is a patient with intrahepatic cholangiocarcinoma administered with a combination therapy of Gemcitabine and Cisplatin as a primary therapy and a combination therapy of S-1 and Resminostat as a secondary therapy for a prior treatment, or a patient with thymic carcinoma administered with a combination therapy of Carboplatin and Paclitaxel as a primary therapy, S-1 as a secondary therapy and Gemcitabine as a tertiary therapy for a prior treatment.

EXAMPLES

Liposomal compositions comprising Eribulin mesylate were prepared with the components set forth in Table 1 or Table 2 in accordance with the following methods and used in the following Examples.

Method of preparing the liposomal composition in Table 1

<Preparation of Aqueous Solution for Liposomal Inner Phase>

Ammonium sulfate and citric acid monohydrate were dissolved and diluted with pure water to prepare an aqueous solution of 200 mM ammonium sulfate/60 mM citric acid. The aqueous solution of 200 mM ammonium sulfate/60 mM citric acid was adjusted to pH 5.5 with an aqueous ammonium solution and then diluted with pure water to obtain an aqueous solution of 100 mM ammonium sulfate/30 mM citric acid.

<Preparation of Liposomal Preparatory Liquid>

Hydrogenated soy phosphatidylcholine, cholesterol, and MPEG2000-distearoylphosphatidylethanolamine were weighted in accordance with a weight ratio of 71:23:27, respectively. These were dissolved in chloroform, respectively, and these solutions were mixed. Chloroform was then evaporated under reduced pressure in a rotary evaporator to prepare a lipid film To the obtained lipid film, the prepared aqueous solution for liposomal inner phase heated to approximately 80° C. was added and the resulting mixture was stirred to prepare a liposomal preparatory liquid. Sizing was performed using an extruder (a product made by Lipex Biomembranes Inc.) heated to approximately 80° C. to obtain a sized liposomal preparatory liquid.

<Preparation of Liposomal Dispersion Liquid>

By eluting the obtained liposomal preparatory liquid through a Sephadex G-50 column with an aqueous solution of 0.9% sodium chloride/10 mM histidine (pH=7.6), the liposomal outer phase was exchanged into an aqueous solution of 0.9% sodium chloride/10 mM histidine. After exchanging the liposomal outer phase, the liquid was centrifuged at 400,000×g for 30 minutes. After the centrifugation, re-dispersion was performed and the liquid volume was adjusted with an aqueous solution of 0.9% sodium chloride/ 10 mM histidine to obtain a liposomal dispersion liquid.

<Preparation of Eribulin Mesylate Solution>

Eribulin mesylate was dissolved in an aqueous solution of 0.9% sodium chloride/10 mM histidine to obtain an Eribulin mesylate solution.

<Preparation of Liposomal Composition>

The liposomal dispersion liquid and the Eribulin mesylate solution were mixed in a glass container and incubated in a water bath at 60° C. for 3 minutes to obtain a liposomal composition with a liposomal inner phase in which Eribulin mesylate was introduced. An aqueous solution of 0.9% sodium chloride/10 mM histidine was added to the liposomal composition and filter sterilization was performed with a 0.22 μm polyvinylidene fluoride (PVDF) filter to obtain an Eribulin mesylate liposomal composition.

Method 1 of preparing the liposomal composition in Table 2

<Preparation of Aqueous Solution for Liposomal Inner Phase>

Ammonium sulfate and citric acid monohydrate were dissolved in pure water. The solution was adjusted to pH 7.5 with an aqueous solution of 1 mol/L sodium hydroxide, and then diluted with pure water to obtain an aqueous solution of 100 mM ammonium sulfate/30 mM citric acid.

<Preparation of Liposomal Preparatory Liquid>

To a lipid mixture comprising hydrogenated soy phosphatidylcholine, cholesterol and MPEG2000-distearoylphosphatidylethanolamine with a weight ratio of 710: 232:269, were added the prepared aqueous solution for liposomal inner phase heated to approximately 80° C. and the resulting mixture was stirred to prepare a liposomal preparatory liquid. Sizing was performed using an extruder (a product made by Lipex Biomembranes Inc.) heated to approximately 80° C. to obtain a sized liposomal preparatory liquid.

<Preparation of Liposomal Dispersion Liquid>

The liposomal outer phase was replaced with an aqueous solution of 96 mg/mL sucrose/10 mM histidine by tangential flow filtration to obtain a liposomal dispersion liquid.

<Preparation of Eribulin Mesylate Solution>

Eribulin mesylate was dissolved in an aqueous solution of 96 mg/mL sucrose/10 mM histidine to obtain an Eribulin mesylate solution.

<Preparation of Liposomal Composition>

The liposomal dispersion liquid and the Eribulin mesylate solution were mixed and the resulting solution was adjusted to around pH 10 with hydrochloric acid or sodium hydroxide and incubated in a water bath at 60° C. to introduce Eribulin mesylate into a liposomal inner phase. The solution was adjusted to pH 7.5 with hydrochloric acid or sodium hydroxide and an aqueous solution of 9.6% sucrose/10 mM histidine was added thereto to make Eribulin mesylate 0.2 mg/ml to obtain an Eribulin mesylate liposomal composition.

Method 2 of preparing the liposomal composition in Table 2

<Preparation of Aqueous Solution for Liposomal Inner Phase>

105.68 g of ammonium sulfate and 50.40 g of citric acid monohydrate were dissolved in water for injection, and the resulting solution was adjusted to pH 7.5 with hydrochloric acid or sodium hydroxide to obtain an aqueous solution for liposomal inner phase.

<Preparation of Liposomal Preparatory Liquid>

106.5 g of hydrogenated soy phosphatidylcholine, 34.8 g of cholesterol and 40.35 g of MPEG2000-distearoylphosphatidylethanolamine were dissolved in ethanol, and the solution was mixed with the aqueous solution for liposomal inner phase heated to approximately 70° C. To the resulting mixture was added water for injection to make a total weight of 8.26 kg. Sizing was performed to make a particle size of about 80 nm using an extruder (a product made by Lipex Biomembranes Inc.) heated to approximately 70° C. to obtain a liposomal preparatory liquid.

<Preparation of Liposomal Dispersion Liquid>

Pellicon 2 cassette ultrafiltration module Biomax (300 kDa) was used to replace the outer phase of the liposomal preparatory liquid with an aqueous solution of 9.6% sucrose/ 10 mM histidine (pH=7.5) to obtain a liposomal dispersion liquid.

<Preparation of Eribulin Mesylate Solution>

Eribulin mesylate was dissolved in an aqueous solution of 9.6% sucrose/10 mM histidine to obtain an Eribulin mesylate solution.

<Preparation of Liposomal Composition>

The liposomal dispersion liquid and Eribulin mesylate solution were mixed and the resulting solution was adjusted to around pH 10 with hydrochloric acid or sodium hydroxide and incubated in a water bath at 60° C. to introduce Eribulin mesylate into a liposomal inner phase. The solution was adjusted to pH 7.5 with hydrochloric acid or sodium hydroxide and an aqueous solution of 9.6% sucrose/10 mM histidine was added thereto to make 0.2 mg/ml of Eribulin mesylate to obtain an Eribulin mesylate liposomal composition.

Example 1

Antitumor effect of combined administration of Eribulin mesylate at low dose (0.1 mg/kg) or Eribulin mesylate liposomal formulation at low dose (0.1 mg/kg) and anti-mouse PD-1 antibody in transplantation model of murine breast cancer 4T1 cell line with P glycoprotein knock-out (Pgp-KO 4T1)

A P glycoprotein-knockout cell line produced from murine breast cancer 4T1 cells (purchased from ATCC) was cultured using RPMI1640 medium (SIGMA) containing 10% of FBS (fetal bovine serum), 1 mM sodium pyruvate, and antibiotics, under conditions at 37° C. in a 5% carbon dioxide gas incubator. The cells were collected using trypsin-EDTA when the cells reached to approximately 80% confluency. The medium described above (RPMI1640) was added to the collected cells, of which a suspension was prepared at $1.0 \times 10^7$ cells/mL, and 0.1 mL of the suspension was subcutaneously transplanted at the right body side into 6 mice (BALB/cAJcl, CLEA Japan, Inc.) per each group of the control group, the Eribulin mesylate alone administration group, the Eribulin mesylate liposomal formulation alone administration group, the anti-mouse PD-1 antibody (Bio X cell) alone administration group, the combined administration group of Eribulin mesylate and anti-mouse PD-1 antibody, and the combined administration group of Eribulin mesylate liposomal formulation and anti-mouse PD-1 antibody. From day 5 post-transplantation, Eribulin mesylate (0.1 mg/kg, once a week, twice in total, tail vein injection), the Eribulin mesylate liposomal formulation (0.1 mg/kg, once a week, twice in total, tail vein injection), and the anti-mouse PD-1 antibody (200 μg/mouse, once a week, twice in total, tail vein injection) were administered, alone or in combination, to the alone administration groups or the anti-mouse PD-1 antibody combined administration groups, respectively. No drug was administered to the control group. The maximum tolerated dose of Eribulin mesylate liposomal formulation in mice is 2.5 mg/kg and the dose in this experiment was set very low at 0.1 mg/kg, which is ⅟25 of the maximum tolerated dose.

The P-glycoprotein knockout cell line (Pgp-KO 4T1 cells) was prepared as follows. Single guide RNA (sgRNA) sequences were designed from the information of two types of P glycoprotein genes (mouse, Abcb1a and Abcb1b) for knockout, and plasmid DNAs for animal cell expression (U6 promoter) into which the sgRNA for each gene was inserted were prepared (pRGEN_Mouse-Abcb1a_U6_SG_1 and pRGEN_Mouse-Abcb1b_U6_SG_1). In addition, Cas9 expressing plasmid DNA (CMV promoter) was prepared (pRGEN_CMV_Cas9). The prepared plasmid DNAs were purified by NucleoBond Xtra Midi EF and used for transfection. First, pRGEN_CMV_Cas9 and pRGEN_Mouse-Abcb1a_U6_SG_1 were used for gene editing for the first gene (Abcb1a). Mouse breast cancer 4T1 cells (purchased from ATCC) were prepared in RPMI1640 medium (SIGMA) containing 10% FBS (fetal bovine serum) and antibiotics under conditions at 37° C. in a 5% carbon dioxide gas incubator. After culturing, the cells were dissociated and collected using Trypsin-EDTA, and the above plasmid DNAs were transfected by a conventional method using electroporation (neopagan) under conditions of multiple mixing ratios. The cells for transfection were seeded on a 6-well microplate, cultured for 3 days, and then a portion of the cells was collected to determine whether or not genome editing was possible. Using the genomic DNA extracted from the collected cells by a conventional method, cleavage of the genomic DNA was confirmed using T7 Endonuclease I (T7E1) Assay. Cloning was performed from cells under mixing ratio in which more genomic DNA was cleaved in the T7E1 Assay. The cloned cells were appropriately subjected for enlarged culture, and cryopreserved, at the same time, the gene sequence was determined by sequence analysis to confirm the mutation of the target gene. One clone cell line was selected from multiple cloned cells in which mutation was confirmed, and gene editing (using pRGEN_CMV_Cas9 and pRGEN_Mouse-Abcb1b_U6_SG_1) for the second gene (Abcb1b) was performed in the same manner as described above. Finally, a 4T1 cell line (Pgp-KO 4T1 cells) was established in which two types of P-glycoprotein genes (mouse, Abcb1a, and Abcb1b) were knocked out.

On day 3, day 7, day 10, day 13, day 16, day 20, day 23, day 27, day 30, and day 34 after administration, with the starting date of administration being day 0, the longest diameter and the short axis of the tumor grown in each mouse were measured with a digimatic caliper (a product made by Mitutoyo Corporation).

The tumor volume was calculated in accordance with the following formula.

$$\text{Tumor volume (mm}^3\text{)} = \text{longest diameter (mm)} \times \text{short axis (mm}^2\text{)}/2$$

The results of measurement of the tumor volume in each group are illustrated as mean and standard deviation (SD) in FIG. 1. As statistical analysis, repeated measures analysis of variance followed by Dunnett's multiple comparison was conducted in comparison with the control group for tumor volumes on all measurement days in all groups (*: $p<0.05$, ***: $p<0.001$). The statistical comparison between two groups of the combined administration group of Eribulin mesylate and anti-mouse PD-1 antibody and the combined administration group of Eribulin mesylate liposomal formulation and anti-mouse PD-1 antibody was conducted by repeated measures analysis of variance (#: $p<0.05$).

As a result, the combined administration of Eribulin mesylate liposomal formulation at low dose (0.1 mg/kg) and anti-mouse PD-1 antibody exhibited a remarkable antitumor effect in comparison with the control group in the Pgp-KO 4T1 tumor transplantation model. * and *** in FIG. 1 indicate that the combined administration of Eribulin mesylate liposomal formulation and anti-mouse PD-1 antibody statistically significantly inhibited tumor growth in comparison with the control group. # indicates that the combined administration of Eribulin mesylate liposomal formulation and anti-mouse PD-1 antibody statistically significantly inhibited tumor growth in comparison with the combined administration of Eribulin mesylate and anti-mouse PD-1 antibody. In contrast, no antitumor effect was observed in the Eribulin mesylate (0.1 mg/kg) alone administration and the Eribulin mesylate liposomal formulation (0.1 mg/kg) alone administration, which are at low doses, and the anti-mouse PD-1 antibody alone administration, and even in the combined administration of Eribulin mesylate (0.1 mg/kg) and anti-mouse PD-1 antibody.

Figure 2:
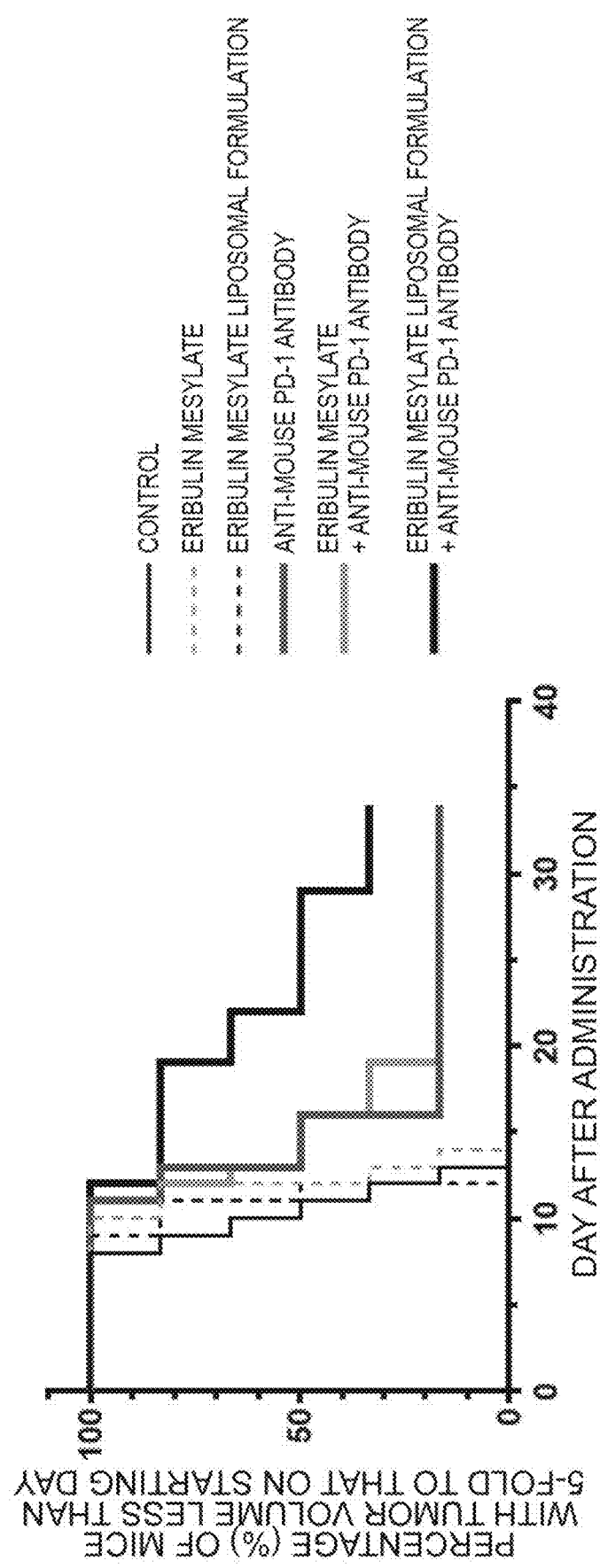
FIG. 2 is a graph illustrating effect of treatment with a combination of a liposomal formulation comprising Eribulin mesylate at a dose of 0.1 mg/kg and an anti-PD-1 antibody on Tx5.

The result of comparison among the groups for the time until the tumor volume exceeds 5 times that on the starting date of administration (Tx5) in the experiment is shown in FIG. 2 and the median of Tx5 in each group and the respective percentages (%) thereof to the control group are set forth in Table 3. For statistical analysis, the Log-rank test was conducted in comparison with the control group to calculate the Bonferroni-corrected p-value (*: p<0.05).

As a result, the combined administration of Eribulin mesylate liposomal formulation (0.1 mg/kg) and anti-mouse PD-1 antibody exhibited the effect of extending (243%) the time of suppressing tumor growth (Tx5) in Pgp-KO 4T1 tumor transplantation model. In contrast, no extension effect was observed in the Eribulin mesylate (0.1 mg/kg) alone administration and the Eribulin mesylate liposomal formulation (0.1 mg/kg) alone administration, which are at low doses, and the anti-mouse PD-1 antibody alone administration, and even in the combined administration of Eribulin mesylate and anti-mouse PD-1 antibody. * in Table 3 indicates that the combined administration of Eribulin mesylate liposomal formulation (0.1 mg/kg) and anti-mouse PD-1 antibody statistically significantly extended the time of tumor growth suppression in comparison with the control group.

TABLE 3

Effect of the combined administration of Eribulin mesylate liposomal formulation (0.1 mg/kg) and anti-mouse PD-1 antibody on Tx5

| Group | Tx5 (days) | Percentage to control |
|---|---|---|
| Control | 10.5 | 100% |
| Eribulin mesylate Alone | 12.0 | 114% |
| Eribulin mesylate liposomal formulation Alone | 11.5 | 110% |
| Anti-mouse PD-1 antibody Alone | 14.5 | 138% |
| Eribulin mesylate + Anti-mouse PD-1 antibody Combined administration | 14.5 | 138% |
| Eribulin mesylate liposomal formulation + Anti-mouse PD-1 antibody Combined administration | 25.5* | 243% |

Example 2

Antitumor effect of combined administration of Eribulin mesylate at low dose (0.3 mg/kg) or Eribulin mesylate liposomal formulation at low dose (0.3 mg/kg) and anti-mouse PD-1 antibody in Pgp-KO 4T1 cell line transplantation model Pgp-KO 4T1 cells were cultured with the RPMI1640 medium containing 10% FBS, 1 mM sodium pyruvate, and antibiotics under conditions at 37° C. in a 5% carbon dioxide gas incubator. The cells were collected using trypsin-EDTA when the cells reached to approximately 80% confluency. The medium described above was added to the collected cells to prepare a suspension at $1.0 \times 10^7$ cells/mL. 0.1 mL of the cell suspension was subcutaneously transplanted at the right body side into 6 mice (BALB/cAJcl, CLEA Japan, Inc.) per each group of the control group, the Eribulin mesylate liposomal formulation alone administration group, the anti-mouse PD-1 antibody (Bio X cell) alone administration group, and the combined administration of Eribulin mesylate liposomal formulation and anti-mouse PD-1 antibody. From day 4 post-transplantation, the Eribulin mesylate liposomal formulation (0.3 mg/kg, once a week, twice in total, tail vein injection) and the anti-mouse PD-1 antibody (200 μg/mouse, once a week, twice in total, tail vein injection) were administered, alone or in combination, to the alone administration groups or the combined administration group, respectively. No drug was administered to the control group.

On day 3, day 7, day 9, day 13, day 17, day 20, day 24, day 27, day 31, day 34, day 38, day 41, day 44, day 48, and day 51 after administration, with the starting date of administration being day 0, the longest diameter and the short axis of the tumor grown in each mouse were measured with a digimatic caliper (a product made by Mitutoyo Corporation).

The tumor volume was calculated in accordance with the following formula.

$$\text{Tumor volume (mm}^3) = \text{longest diameter (mm)} \times \text{short axis (mm}^2)/2$$

Figure 3:
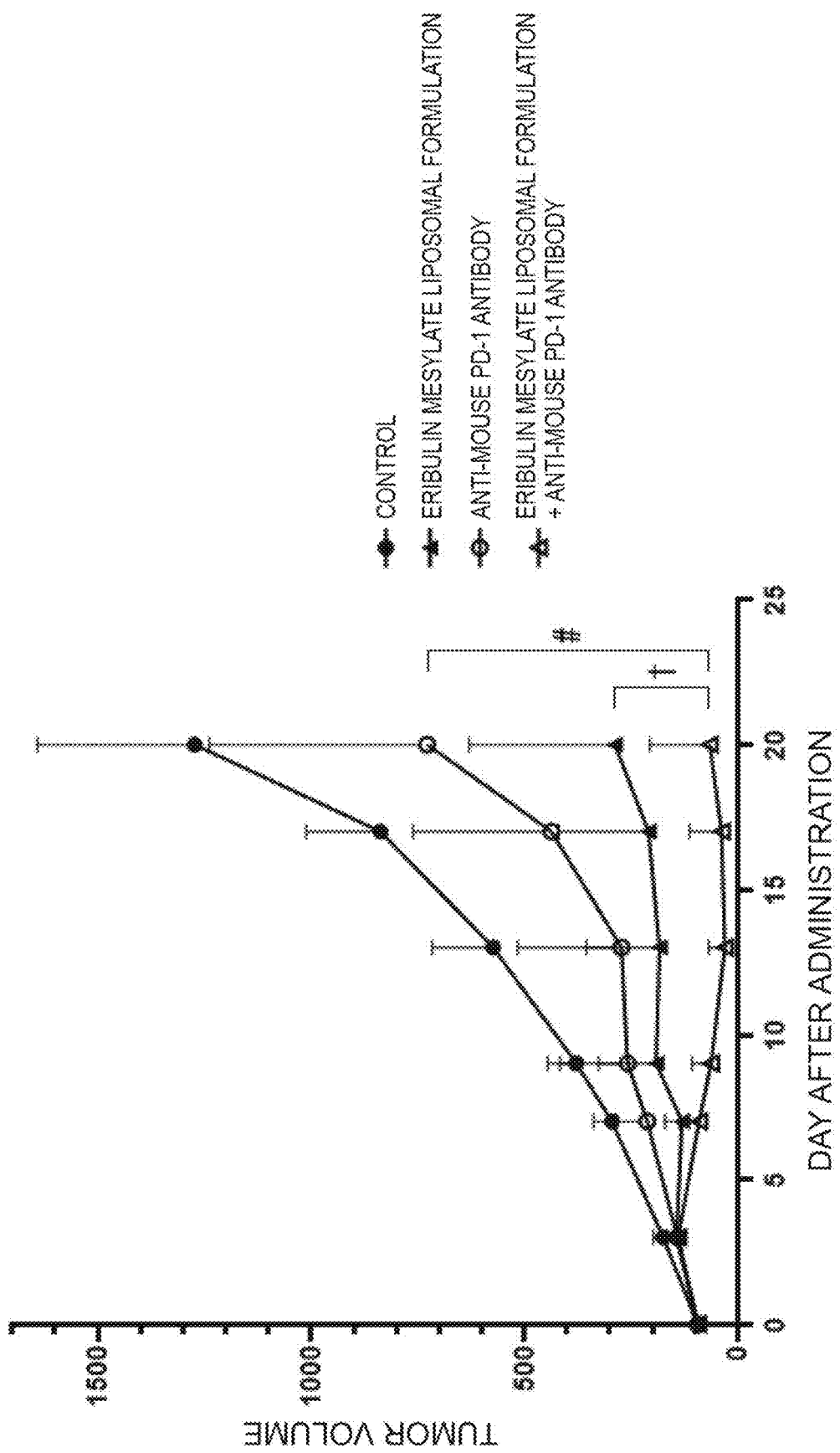
FIG. 3 is a graph illustrating effect of treatment with a combination of a liposomal formulation comprising Eribulin mesylate at a dose of 0.3 mg/kg and an anti-PD-1 antibody on tumor growth.

The mean and standard deviation (SD) of the results of measurement of the tumor volume in each group are illustrated in FIG. 3 and the frequencies of mice with tumor disappearance are set forth in Table 4. For statistical analysis, the statistical comparison between two groups of the Eribulin mesylate liposomal formulation alone administration group or the anti-mouse PD-1 antibody alone administration group and the combined administration group of Eribulin mesylate liposomal formulation and anti-mouse PD-1 antibody was conducted by repeated measures analysis of variance (t, #: p<0.05).

As a result, in the Pgp-KO 4T1 tumor transplantation model, the combined administration of Eribulin mesylate liposomal formulation at low dose (0.3 mg/kg) and anti-mouse PD-1 antibody exhibited excellent antitumor effect in comparison with the Eribulin mesylate liposomal formulation alone administration group or anti-mouse PD-1 antibody alone administration group. In FIG. 3, (t) indicates that the combined administration of Eribulin mesylate liposomal formulation and anti-mouse PD-1 antibody statistically significantly inhibited tumor growth in comparison with the Eribulin mesylate liposomal formulation alone administration and (#) indicates that the combined administration of Eribulin mesylate liposomal formulation and anti-mouse PD-1 antibody statistically significantly inhibited tumor growth in comparison with the anti-mouse PD-1 antibody alone administration. The tumor disappearance was observed in the combined administration group of Eribulin mesylate liposomal formulation (0.3 mg/kg) and anti-mouse PD-1 antibody at a frequency higher than other groups.

TABLE 4

Frequency of appearance of mice with tumor disappearance in each group

| Group | Frequency (%) of mice with tumor disappearance |
|---|---|
| Control | 0/6 (0%) |
| Eribulin mesylate liposomal formulation Alone | 1/6 (17%) |
| Anti-mouse PD-1 antibody Alone | 0/6 (0%) |
| Eribulin mesylate liposomal formulation + Anti-mouse PD-1 antibody Combined administration | 4/6 (67%) |

Figure 4:
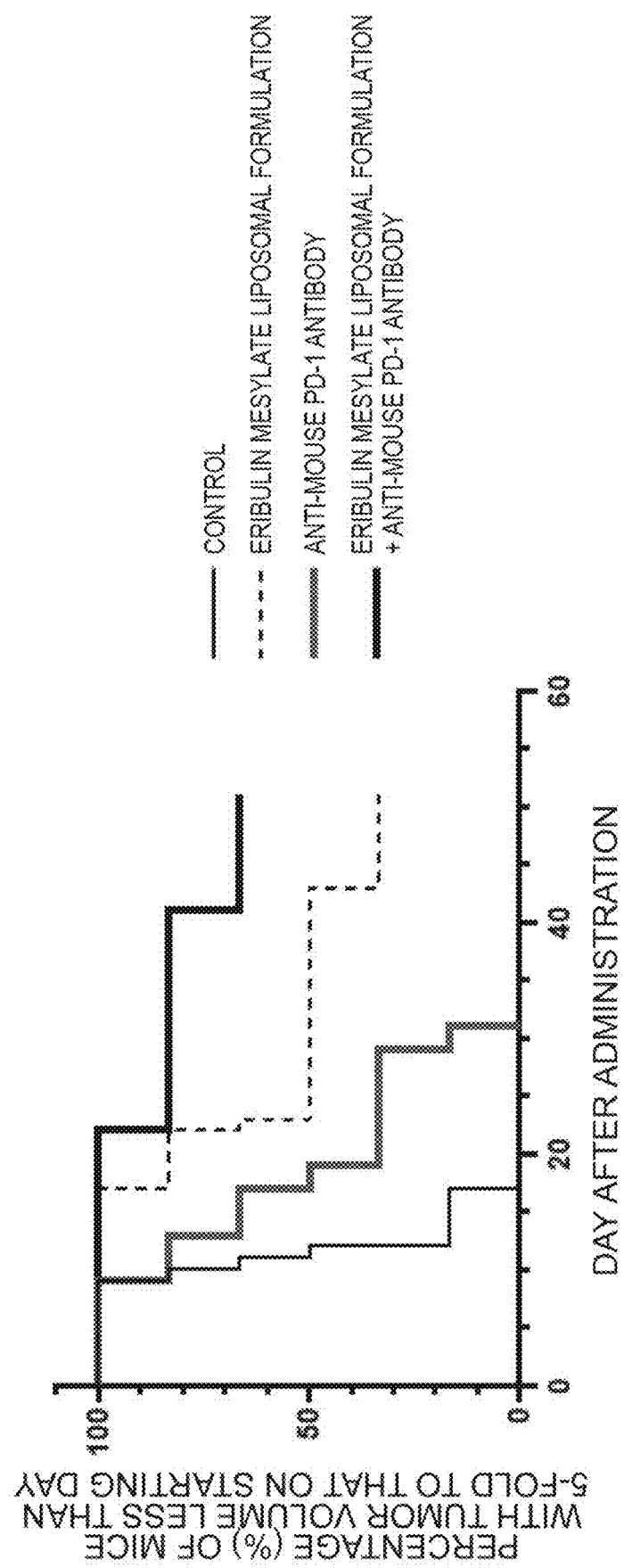
FIG. 4 is a graph illustrating effect of treatment with a combination of a liposomal formulation comprising Eribulin mesylate at a dose of 0.3 mg/kg and an anti-PD-1 antibody on Tx5.

The result of comparison of the groups for the time until the tumor volume exceeds 5 times that on the starting date of administration (Tx5) in the experiment is shown in FIG. 4 and the median of Tx5 in each group and the percentage (%) thereof to the control group are set forth in Table 5. For statistical analysis, the Log-rank test between two groups of the combined administration group of Eribulin mesylate liposomal formulation and anti-mouse PD-1 antibody to the anti-mouse PD-1 antibody alone administration group was conducted (#: p<0.05).

As a result, in the Pgp-KO 4T1 tumor transplantation model, the combined administration of Eribulin mesylate liposomal formulation (0.3 mg/kg) and the anti-mouse PD-1 antibody exhibited the effect of extending suppression time of tumor growth (Tx5) in comparison with the control group, the Eribulin mesylate liposomal formulation alone administration group, and the anti-mouse PD-1 antibody alone administration group. # in Table 5 indicates that the combined administration of Eribulin mesylate liposomal formulation and anti-mouse PD-1 antibody statistically significantly extended suppression time of tumor growth in comparison with the anti-mouse PD-1 antibody alone administration.

TABLE 5

Effect of combined administration of Eribulin mesylate liposomal formulation (0.3 mg/kg) and anti-mouse PD-1 antibody to Tx5

| Group | Tx5 (days) | Ratio to control |
|---|---|---|
| Control | 11.5 | 100% |
| Eribulin mesylate liposomal formulation Alone | 33.0 | 287% |
| Anti-mouse PD-1 antibody Alone | 18.0 | 157% |
| Eribulin mesylate liposomal formulation + Anti-mouse PD-1 antibody Combined administration | >51.0 # | >443% |

Example 3

Antitumor effect of combined administration of Eribulin mesylate at low dose (0.3 mg/kg) or Eribulin mesylate liposomal formulation at low dose (0.3 mg/kg) and anti-mouse PD-1 antibody in transplantation model of murine colorectal cancer CT-26 cell line with P glycoprotein knockout (Pgp-KO CT-26)

From mouse colorectal cancer CT-26 cells (purchased from ATCC), a P glycoprotein knockout cell line (Pgp-KO CT-26) was produced in accordance with the same materials and procedures used in the production of Pgp-KO 4T1 cells. Pgp-KO CT-26 cells were cultured using RPMI1640 medium (FUJIFILM Wako Pure Chemical Corporation) containing 10% of FBS (fetal bovine serum), and antibiotics, under conditions at 37° C. in a 5% carbon dioxide gas incubator. The cells were collected using trypsin-EDTA when the cells reached to approximately 80% confluency. MSS medium was added to the collected cells, of which a suspension was prepared at $2.0 \times 10^7$ cells/mL, and 0.1 mL of the suspension was subcutaneously transplanted at the right body side into 7 mice (BALB/cAJcl, CLEA Japan, Inc.) per each group of the control group, the Eribulin mesylate alone administration group, the Eribulin mesylate liposomal formulation alone administration group, the anti-mouse PD-1 antibody (Bio X cell) alone administration group, the combined administration group of Eribulin mesylate and anti-mouse PD-1 antibody, and the combined administration group of Eribulin mesylate liposomal formulation and anti-mouse PD-1 antibody. From day 15 post-transplantation, Eribulin mesylate (0.3 mg/kg, once a week, three times in total, tail vein injection), Eribulin mesylate liposomal formulation (0.3 mg/kg, once a week, three times in total, tail vein injection), and the anti-mouse PD-1 antibody (200 μg/mouse, once a week, three times in total, tail vein injection) were administered, alone or in combination, to the alone administration groups or anti-mouse PD-1 antibody combined administration groups, respectively. No drug was administered to the control group.

With the starting date of administration being day 0, the longest diameter and the short axis of the tumor grown in each mouse were measured with time to Day 18 with a digimatic caliper (a product made by Mitutoyo Corporation).

The tumor volume was calculated in accordance with the following formula.

Tumor volume $(mm^3)$ = longest diameter (mm)×short axis $(mm^2)/2$

The results of measurement of the tumor volume in each group are illustrated as mean and standard deviation (SD) in Table 6. As statistical analysis, repeated measures analysis of variance followed by Dunnett's multiple comparison was conducted in comparison with the control group for tumor volumes in all groups (*: p<0.05,).

As a result, the combined administration of Eribulin mesylate liposomal formulation at low dose (0.3 mg/kg) and anti-mouse PD-1 antibody exhibited a remarkable antitumor effect in comparison with the control group in the Pgp-KO CT-26 tumor transplantation model. * in Table 6 indicate that the combined administration of Eribulin mesylate liposomal formulation and the anti-mouse PD-1 antibody statistically significantly inhibited tumor growth in comparison with the control group. In contrast, no antitumor effect at low doses with the Eribulin mesylate (0.3 mg/kg) alone administration, the Eribulin mesylate liposomal formulation (0.3 mg/kg) alone administration, the anti-mouse PD-1 antibody alone administration, and even in the combined administration of Eribulin mesylate (0.3 mg/kg) and anti-mouse PD-1 antibody was observed with a significant difference in comparison with the control group.

TABLE 6

Effect of the combined treatment of Eribulin mesylate liposomal formulation (0.3 mg/kg) and anti-mouse PD-1 antibody on tumor growth in Pgp-KO CT-26 tumor transplantation model

| Group | Tumor volume |
|---|---|
| Control | 1851 ± 517 $(mm^3)$ |
| Eribulin mesylate Alone | 1139 ± 733 $(mm^3)$ |
| Eribulin mesylate liposomal formulation Alone | 1012 ± 575 $(mm^3)$ |
| Anti-mouse PD-1 antibody Alone | 1378 ± 632 $(mm^3)$ |
| Eribulin mesylate + Anti-mouse PD-1 antibody Combined administration | 1170 ± 772 $(mm^3)$ |
| Eribulin mesylate liposomal formulation + Anti-mouse PD-1 antibody Combined administration | 770 ± 593 $(mm^3)$* |

Example 4

Antitumor effect of combined administration of Eribulin mesylate liposomal formulation at low dose (0.3 mg/kg) and anti-mouse PD-1 antibody in a mouse renal cancer RAG cell line transplantation model RAG cells (purchased from ATCC) used in the transplant model were conditioned in mice (BALB/cAnNCrlCrlj, Charles River Laboratories, Japan) in advance. RAG cells were suspended in MSS (Wako Pure Chemical Industries, Ltd.) at a concentration of $2 \times 10^8$ cells/mL. To this suspension was added the same volume of Matrigel™ matrix (Nippon Becton Dickinson Co., Ltd.) and mixed well. The mixture was implanted into the subcutaneous region of the right flank of each mouse at 0.1 mL. On day 38 post-transplantation, the generated tumor was removed and cut into small pieces, and Tumor Dissociation Kit, Mouse (Miltenyi) was added thereto, and stirred using Gentle MACS (Miltenyi). After passing through a 70 µm cell strainer, the cells were collected by centrifugation, and cultured in an EMEM medium (Wako Pure Chemical Industries, Ltd.) containing 10% bovine serum under conditions at 37° C. in a 5% carbon dioxide gas incubator and cryopreserved.

The cells obtained by the above treatment were cultured using EMEM medium containing 10% FBS and antibiotics. The cells were collected using trypsin-EDTA when the cells reached to approximately 80% confluency. HBSS was added to the collected cells to prepare a suspension at $2.5 \times 10^7$ cells/mL. 0.1 mL of the cell suspension was subcutaneously transplanted at the right body side into 10 mice (BALB/cAnNCrlCrlj, Charles River Laboratories, Japan) per each group of the control group, the Eribulin mesylate liposomal formulation alone administration group, the anti-mouse PD-1 antibody (Bio X cell) alone administration group, and the combined administration group of Eribulin mesylate liposomal formulation and anti-mouse PD-1 antibody. From day 6 post-transplantation, the Eribulin mesylate liposomal formulation (0.3 mg/kg, once a week, three times in total, tail vein injection) and the anti-mouse PD-1 antibody (200 µg/mouse, once every 3 days, ten times in total, intraperitoneal administration) were administered alone or in combination to the alone administration groups or the combined administration group, respectively. No drug was administered to the control group.

On day 3, day 7, day 10, day 14, day 17, day 21, day 24, day 28, day 31, day 35, day 38 and day 42 after administration, with the starting date of administration being day 0, the longest diameter and the short axis of the tumor grown in each mouse were measured with a digimatic caliper (a product made by Mitutoyo Corporation).

The tumor volume was calculated in accordance with the following formula.

$$\text{Tumor volume (mm}^3\text{)} = \text{longest diameter (mm)} \times \text{short axis (mm}^2\text{)}/2$$

Table 7 shows the frequencies of mice with tumor shrinkage of 50% or more at best in each group as the response rate, and Table 8 shows the frequencies of mice with tumor disappearance. For statistical analysis, the comparison between the Eribulin mesylate liposomal formulation alone administration group, the anti-mouse PD-1 antibody alone administration group, or the combined administration group of Eribulin mesylate liposomal formulation and anti-mouse PD-1 antibody and control group was conducted by 2-sided Fisher's exact test (#: p<0.05).

As a result, in the RAG tumor transplantation model, the combined administration of Eribulin mesylate liposomal formulation at low dose (0.3 mg/kg) and anti-mouse PD-1 antibody exhibited high response in comparison with the Eribulin mesylate liposomal formulation alone administration group or the anti-mouse PD-1 antibody alone administration group. In Table 7, (*) indicates that the combined administration of Eribulin mesylate liposomal formulation and anti-mouse PD-1 antibody statistically significantly responded.

On the other hand, no significant response was observed with the Eribulin mesylate liposomal formulation (0.3 mg/kg) alone administration or the anti-mouse PD-1 antibody alone administration. The tumor disappearance was observed in the combined administration group of Eribulin mesylate liposomal formulation (0.3 mg/kg) and anti-mouse PD-1 antibody at a frequency higher than other groups.

TABLE 7

Response rate in each group

| Group | Number of mice responded/Number of mice in each group (Response rate %) |
|---|---|
| Control | 0/10 (0%) |
| Eribulin mesylate liposomal formulation Alone | 4/10 (40%) |
| Anti-mouse PD-1 antibody Alone | 2/10 (20%) |
| Eribulin mesylate liposomal formulation + Anti-mouse PD-1 antibody Combined administration | 5/10 (50%) |

TABLE 8

Frequency of appearance of mice with tumor disappearance in each group

| Group | Frequency (%) of mice with tumor disappearance |
|---|---|
| Control | 0/10 (0%) |
| Eribulin mesylate liposomal formulation Alone | 2/10 (20%) |
| Anti-mouse PD-1 antibody Alone | 1/10 (10%) |
| Eribulin mesylate liposomal formulation + Anti-mouse PD-1 antibody Combined administration | 4/10 (40%) |

Example 5

Open-label, Phase 1b/2 study of combination of Eribulin mesylate liposomal formulation and Nivolumab in patients with solid tumors The study is multicenter, single-group, and Open-label study. The Phase 1b part of the study is for patients with solid tumors without standard therapy or another effective therapy, and the Phase 2 part is for patients with esophageal cancer having progressed during or after a primary chemotherapy (a combination chemotherapy comprising a platinum-based drug and a fluorinated pyrimidine-based drug), patients with small cell lung cancer having progressed during or after a primary chemotherapy (a combination chemotherapy comprising a platinum-based drug), or patient with gastric cancer having progressed during or after a secondary chemotherapy (a combination chemotherapy comprising a platinum-based drug and a fluorinated pyrimidine-based drug as a primary chemotherapy and a chemotherapy comprising a taxane-based drug as a secondary chemotherapy.

The study consists of three periods: the pre-administration period, the administration period, and the follow-up period (only for Phase 2 part). The pre-administration period includes screening for checking the eligibility and baseline for checking the disease status and it was within 28 days. During the administration period, subjects received administration of Eribulin mesylate liposomal formulation and Nivolumab. Tumor assessment was performed every 6 weeks from the start of administration. The follow-up period (only for Phase 2 part) is initiated after discontinuation of Eribulin mesylate liposomal formulation and Nivolumab to investigate the survival and post-treatment of the subjects.

In the Phase 1b part, two administration methods: Schedule 1 and Schedule 2, were examined. In Schedule 1, Eribulin mesylate liposomal formulation and Nivolumab were administered intravenously on day 1 of 21-day cycle, and the dose of Nivolumab was 360 mg, and the dose of Eribulin mesylate liposomal formulation (as mesylate) was 1.7 or 2.1 mg/m². In Schedule 2, Eribulin mesylate liposomal formulation and Nivolumab were administered intravenously on day 1 and day 15 of 28-day cycle, and the dose of Nivolumab was 240 mg, and the dose of Eribulin mesylate liposomal formulation (as mesylate) was 1.1 or 1.4 mg/m².

In the phase 2 part, the recommended dosage determined in the phase 1b part is used.

The primary objective of the study is to evaluate the safety and tolerability of the combination of Eribulin mesylate liposomal formulation and Nivolumab to determine the recommended dosage for Phase 2 (Phase 1b part), and to evaluate the objective response rate in each cancer at the recommended dosage (Phase 2 part). The secondary objective of the study is to evaluate the safety, pharmacokinetics and progression-free survival of the combination of Eribulin mesylate liposomal formulation and Nivolumab.

Patients who meet all of the following criteria are eligible for the study.

Inclusion Criteria
(1) only for Phase 1b part:
Patients with advanced, unresectable or recurrent solid tumors without standard therapy or another effective therapy (patients receiving Nivolumab monotherapy as standard therapy are eligible)
(2) only for Phase 2 part:
Patient with unresectable gastric cancer, esophageal cancer or small cell lung cancer who have had a definitive diagnosis and whose disease progresses at the physician's discretion during or after a primary chemotherapy (or a secondary chemotherapy for gastric cancer) and who have not received other systemic chemotherapy for advanced or recurrent cancer
(3) only for Phase 2 part:
Patients who received the following chemotherapy as a prior chemotherapy
Gastric cancer: a combination chemotherapy comprising a platinum-based drug and a fluorinated pyrimidine-based drug as a primary chemotherapy and a chemotherapy comprising a taxane-based drug as a secondary chemotherapy
Esophageal cancer: a combination chemotherapy comprising a platinum-based drug and a fluorinated pyrimidine-based drug (but not comprising a taxane-based drug) as a primary chemotherapy
Small cell lung cancer: a combination chemotherapy comprising a platinum-based drug as a primary chemotherapy
(4) Patients with tumor lesions that can be biopsied and who consent to tumor biopsy before and after administration of the investigational drug (If biopsy before administration is not possible due to safety concerns, submission of preserved tumor specimens is permitted)
(5) Patients who are expected to survive for 12 weeks or longer
(6) Patients with ECOG-PS 0-1
(7) Japanese patient aged 20 or above at the time of consent
(8) Patients whose adverse events (excluding hair loss and Grade 2 peripheral neuropathy) due to a prior therapy for cancer have recovered to Grade 0-1 (renal/bone marrow/liver/pancreatic function must be recovered to meets inclusion criteria)
(9) Patients who have passed the following period from the end of a prior therapy to C1D1 (cycle 1 day 1)
a) Non-cytotoxic anti-cancer drug: 4 weeks (or 5 half-lives, whichever shorter) or longer
b) Cytotoxic anti-cancer drug and radiation therapy: 3 weeks or longer
c) Treatment with anti-cancer drug of antibody preparation: 4 weeks or longer
d) Investigative drug or medical device under investigation: 4 weeks or longer
e) Blood transfusion, platelet transfusion or G-CSF preparation: 2 weeks or longer
f) Live or attenuated vaccine: 4 weeks or longer
(10) Patients with appropriate renal function: serum creatinine≤1.5×upper limit of normal (ULN) (in the case of >1.5×ULN, patients having creatinine clearance by the Cockcroft-Gault method≥40 mL/min are eligible)
(11) Patients with appropriate bone marrow function:
a) neutrophil count≥2,000/mm³
b) platelet count≥100,000/mm³
c) hemoglobin≥8.5 g/dL
(12) Patients with appropriate liver function:
a) international normalized ratio (INR) as anticoagulation ability≤1.5
b) total bilirubin≤1.5×ULN (for Gilbert's syndrome patient≤3.0×ULN)
c) alkaline phosphatase (ALP), alanine aminotransferase (ALT) and aspartate aminotransferase (AST)≤3×ULN (for patient having liver lesions≤5×ULN)
(13) Patients with appropriate pancreatic function: amylase and lipase≤1.5×ULN (for patients having pancreatic lesions≤3×ULN)
(14) only for Phase 2 part: Patients with measurable lesions in RECIST 1.1 (when lesions that have undergone radiation therapy or topical therapy are regarded as measurable lesions, the lesions must be aggravated)
(15) Patients who can consent to documents and comply with the clinical trial protocol Patients who meet any of the following criteria will be excluded from the study.

Exclusion Criteria
(1) Patients with any of the following cardiac diseases
New York Heart Association (NYHA) class II or higher cardiac failure
Unstable ischemic heart disease (myocardial infarction within 6 months prior to C1D1, angina requiring at least 2 times a week of nitrovasodilator)
QTcF>480 ms prolonged QT interval
(2) Patients with a history of hypersensitivity reactions to liposomal preparations
(3) Patients who underwent major surgery within 21 days from C1D 1
(4) Patients with a history of Eribulin or Nivolumab
(5) Patients who experienced Grade 3 or higher immune-related adverse events or discontinued treatment with anti-PD-1 antibodies, anti-PD-L 1 antibodies, anti-PD-L2 antibodies, anti-CD137 antibodies, anti-CTLA-4 antibodies, or other antibodies and drugs that target T-cell co-stimulation or checkpoints, or cancer vaccines
(6) Patients who are known to be intolerant to the investigational drug or any of its additives or antibody preparations
(7) Patients with known human immunodeficiency virus (HIV) positive or acquired immunodeficiency syndrome (AIDS)
(8) Patients with active hepatitis B or C (hepatitis B virus surface [HBs] antigen positive, HBs antigen negative and anti-HBs antibody-positive or anti-HBc antibody positive and HBV-DNA positive, or HCV-RNA positive)
(9) Patients with active infections who required systemic treatment within 14 days from C1D1

(10) Patients with membrane carcinomatosis
(11) Patients with brain or subdural metastasis or mvasion. Excluded are Patients who have completed topical treatment and have discontinued corticosteroids 4 weeks before C1D1. Signs (e.g. on radiological examination) and symptoms should be stable for 4 weeks from C1D1.
(12) Patients with pulmonary lymphangitis and respiratory failure who require active treatment (including oxygen inhalation)
(13) Patients with active or known autoimmune diseases or suspected autoimmune diseases. Except:
Patients with vitiligo vulgaris, type I diabetes, recovered childhood asthma, or atopy
Patients with suspected autoimmune thyroid disorders who have normal current thyroid function or who can maintain normal thyroid function with hormone replacement therapy alone for residual hypothyroidism
(14) Patients with or having a history of clinically or image-diagnosed interstitial lung disease or pulmonary fibrosis (patients with radiation pneumonitis with confirmed stable fibrosis and no risk of recurrence are eligible)
(15) Patients having a history of organ transplantation requiring immunosuppressive drug administration
(16) Patients who require systemic administration of corticosteroids (equivalent to more than 10 mg/day of prednisolone) or other immunosuppressive drugs within 14 days from C1D1. Patients using inhaled or topically administered corticosteroids (if less absorbed in the body) can be enrolled in the absence of active autoimmune disease.
(17) Only for Phase 2 part: Patients with active malignancies within 24 months from C1D1 (primary disease, fully treated non-invasive melanoma, basal cell carcinoma of skin/squamous cell carcinoma, non-invasive cervical cancer/bladder cancer and early gastric cancer/colorectal cancer are excluded)
(18) Patients with clinically significant disease/condition (e.g., heart, respiratory, digestive, renal disease) determined by the investigator or subinvestigator to affect subject safety or study evaluation
(19) For women, patients who are lactating or pregnant at screening or at baseline (patients tested positive for human chorionic gonadotropin [hCG] or beta subunit of human chorionic gonadotropin [β-hCG]). If the screening is negative but not within 72 hours of C1D1, the test should be repeated.
(20) In the case of fertile men and women of childbearing potential, patients who do not agree to use medically appropriate contraceptive methods') for the duration of the study and until 5 months (7 months for male subjects) after the administration of the investigational drug.
Note) Double contraception with two of the following: vasectomy, tubal ligation, use of condom*, contraceptive sponge, contraceptive foam, contraceptive gel**, contraceptive diaphragm*, or contraceptive ring*, or use of oral contraceptive* for 28 days or more before the start of administration of this investigational drug (whether or not approval or certification of drugs and medical devices in Japan [*: Yes, **: No])
The administration of Eribulin mesylate liposomal formulation and Nivolumab was decided to continue until disease progression, intolerable side effects occurrence, subject's request for discontinuation, consent withdrawal, or the sponsor's discontinuation of the study.

Interim Results of Phase 1b Part
Case 1
A case of intrahepatic cholangiocarcinoma (Schedule 2, a dose of Eribulin mesylate liposomal formulation is 1.1 mg/m$^2$)
To a patient who had received a combination therapy of Gemcitabine and Cisplatin as a primary therapy, a combination therapy of S-1 and Resminostat as a secondary therapy, and an investigational drug (details unknown) as a tertiary therapy, for a prior treatment, were administered 1.1 mg/m$^2$ of Eribulin mesylate liposomal formulation and 240 mg of Nivolumab once every two weeks in Schedule 2. After administration, at Week 6/12/18/24/30/36, the sum of diameters of the target lesions from the baseline was reduced by 10.3%, 14.7%, 23.5%, 40.8%, 46.2% and 51.4% from the baseline, respectively, and it was considered as a partial response.
Case 2
A case of thymic carcinoma (Schedule 1, a dose of Eribulin mesylate liposomal formulation is 1.7 mg/m$^2$)
To a patient who had received a combination therapy of Carboplatin and Paclitaxel as a primary therapy, S-1 as a secondary therapy, Gemcitabine as a tertiary therapy, an investigational drug (a combination of an unknown drug and a PD-L 1 antibody) as a quaternary therapy and an investigational drug (details unknown) as a quinary therapy, for a prior treatment, were administered 1.7 mg/m$^2$ of Eribulin mesylate liposomal formulation and 360 mg of Nivolumab once every three weeks in Schedule 1. After administration, at Week 6/12/18, the sum of diameters of the target lesions was reduced by 17.8%, 100% and 100% from the baseline, respectively, and it was considered as a partial response.
Case 3
A case of thymic carcinoma (Schedule 1, a dose of Eribulin mesylate liposomal formulation is 1.7 mg/m$^2$)
To a patient who had received a combination therapy of Carboplatin and Paclitaxel as a primary therapy for a prior treatment, were administered 1.7 mg/m$^2$ of Eribulin mesylate liposomal formulation and 360 mg of Nivolumab once every three weeks in Schedule 1. After administration, at Week 6/12/18/24/28/34/38/45, the sum of diameters of the target lesions was reduced by 21.9%, 22.7%, 34.1%, 34.9%, 34.5%, 31.3%, 24.7% and 3.4% from the baseline, respectively, and it was considered as a partial response.
Case 4
A case of small cell lung cancer (Schedule 1, a dose of Eribulin mesylate liposomal formulation is 2.1 mg/m$^2$)
To a patient who had received a combination therapy of Cisplatin and Etoposide as a primary therapy, a combination therapy of Carboplatin, Etoposide and Atezolizumab as a secondary therapy, for locally advanced disease states and Amrubicin as a primary therapy, a combination therapy of Cisplatin and Irinotecan as a secondary therapy, for metastatic disease states, for a prior treatment, were administered 2.1 mg/m$^2$ of Eribulin mesylate liposomal formulation and 360 mg of Nivolumab once every three weeks in Schedule 1. After administration, at Week 6, the sum of diameters of the target lesions was reduced by 46.9% from the baseline, and it was considered as a partial response.
Interim Results of Phase 2 Part in Gastric Cancer
To gastric cancer patients who had received a combination therapy comprising a platinum-based drug and a fluorinated pyrimidine-based drug as a primary therapy, and a combination therapy comprising a taxane-based drug as a secondary therapy, were administered 2.1 mg/m$^2$ of Eribulin mesylate liposomal formulation and 360 mg of Nivolumab once every three weeks in Schedule 1. In 6 cases, partial responses were observed at any tumor assessment time points, with a 30% or greater reduction in the sum of diameters of the target lesions from baseline.

Interim Results of Phase 2 Part in Esophageal Cancers

To esophageal cancer patients who had received a combination therapy comprising a platinum-based drug and a fluorinated pyrimidine-based drug as a primary therapy, were administered 2.1 mg/m$^2$ of Eribulin mesylate liposomal formulation and 360 mg of Nivolumab once every three weeks in Schedule 1. In 5 cases, partial responses were observed at any tumor assessment time points, with a 30% or greater reduction in the sum of diameters of the target lesions from baseline.

Interim Results of Phase 2 Part in Small Cell Lung Cancers

To small cell lung cancer patients who had received a combination therapy comprising a platinum-based drug as a primary therapy, were administered 2.1 mg/m$^2$ of Eribulin mesylate liposomal formulation and 360 mg of Nivolumab once every three weeks in Schedule 1. In 7 cases, partial responses were observed at any tumor assessment time points, with a 30% or greater reduction in the sum of diameters of the target lesions from baseline. Patients had received an anti-PD-L1 antibody as a prior treatment in 5 cases out of the 7 cases.

Case 5

A case of non-small cell lung cancer (registered in Phase 2 part of small cell lung cancer and then the pathological diagnosis was changed to non-small cell lung cancer)

To a patient who had received a combination therapy of Cisplatin and Etoposide as a primary therapy, were administered 2.1 mg/m$^2$ of Eribulin mesylate liposomal formulation and 360 mg of Nivolumab once every three weeks in Schedule 1. After administration, at Week 12/18/24, the sum of diameters of the target lesions was reduced by 39.7%, 48.0%, and 49.0% from the baseline, respectively, and it was considered as a partial response.

Example 6

Antitumor effect of combined administration of Eribulin mesylate liposomal formulation at low dose (0.3 mg/kg) and anti-human PD-1 antibody in tumor-bearing mice of human gastric cancer MKN45 cell line having human immunity Preparation of Human Peripheral Blood Mononuclear Cells Human peripheral blood mononuclear cells were isolated from blood collected from healthy volunteers. An equal amount of Cellotion (ZENOGEN PHARMA CO., LTD.) was added to the blood and mixed, and a human peripheral blood mononuclear cell layer was isolated using a Leucosep lymphocyte separation tube (Greiner Bio-One). The isolated human peripheral blood mononuclear cells were suspended in CELLBANKER 2 (ZENOGEN PHARMA CO., LTD.) and stored at −80° C. until use.

Preparation of human gastric cancer MKN45 tumor-bearing mice Human gastric cancer MKN45 cells (purchased from JCRB cell bank) were cultured in RPMI1640 medium (FUJIFILM Wako Pure Chemical Corporation) containing 10% FBS (fetal bovine serum) and antibiotics under conditions at 37° C. in a 5% carbon dioxide gas incubator. The cells were collected using trypsin-EDTA when the cells reached to approximately 80% confluency. Hank's balanced salt solution (Thermo Fisher Scientific) was added to the collected cells to prepare a suspension at 4.0×10$^7$ cells/mL, and 0.1 mL of the suspension was subcutaneously transplanted to the right body side into 5 to 6 mice (5 mice in the control group, 6 mice in the other groups; NOD/Shi-scid, IL-2RγKO Jic, In-Vivo Science Inc.) in control group, Eribulin mesylate liposomal formulation alone administration group, the anti-human PD-1 antibody (MSD) alone administration group, and the combined administration group of Eribulin mesylate liposomal formulation and anti-human PD-1 antibody.

Preparation of Human Gastric Cancer MKN45 Tumor-Bearing Mice Having Human Immunity The isolated human peripheral blood mononuclear cells were transplanted into the human gastric cancer MKN45 tumor-bearing mice prepared by the above method to prepare human gastric cancer MKN45 tumor-bearing mice having human immunity. Human peripheral blood mononuclear cells stored at −80° C. were thawed, the cells were separated by centrifugation (500×g, 10 minutes), and Hank's balanced salt solution (Thermo Fisher Scientific) was added to prepare a suspension at 2.0×10$^7$ cells/mL. Mice on day 3 after transplantation of human gastric cancer MKN45 cell line were transplanted with 0.2 mL (4.0×10$^6$ cells/mouse) of the human peripheral blood mononuclear cell suspension prepared by the above method by tail vein injection.

Anti-Tumor Effect

Using human gastric cancer MKN45 tumor-bearing mice having human immunity prepared by the above method, the antitumor effect of the combined administration of Eribulin mesylate liposomal formulation at low dose (0.3 mg/kg) and an anti-human PD-1 antibody was evaluated. From day 4 after human peripheral blood mononuclear cell transplantation (day 7 after human gastric cancer MKN45 cell line transplantation), the Eribulin mesylate liposomal formulation (0.3 mg/kg, once a week, twice in total, tail vein injection) and the anti-human PD-1 antibody (10 mg/kg, twice a week, four times in total, intraperitoneal injection) were administered, alone or in combination, to the alone administration groups or the combination administration group, respectively. No drug was administered to the control group.

On day 4, day 8, day 10, day 12, day 15, day 17, day 19, and day 22 after administration, with the starting date of administration being day 1, the longest diameter and the short axis of the tumor grown in each mouse were measured with a digimatic caliper (a product made by Mitutoyo Corporation).

The tumor volume was calculated in accordance with the following formula.

$$\text{Tumor volume (mm}^3\text{)} = \text{longest diameter (mm)} \times \text{short axis (mm}^2\text{)}/2$$

Figure 5:
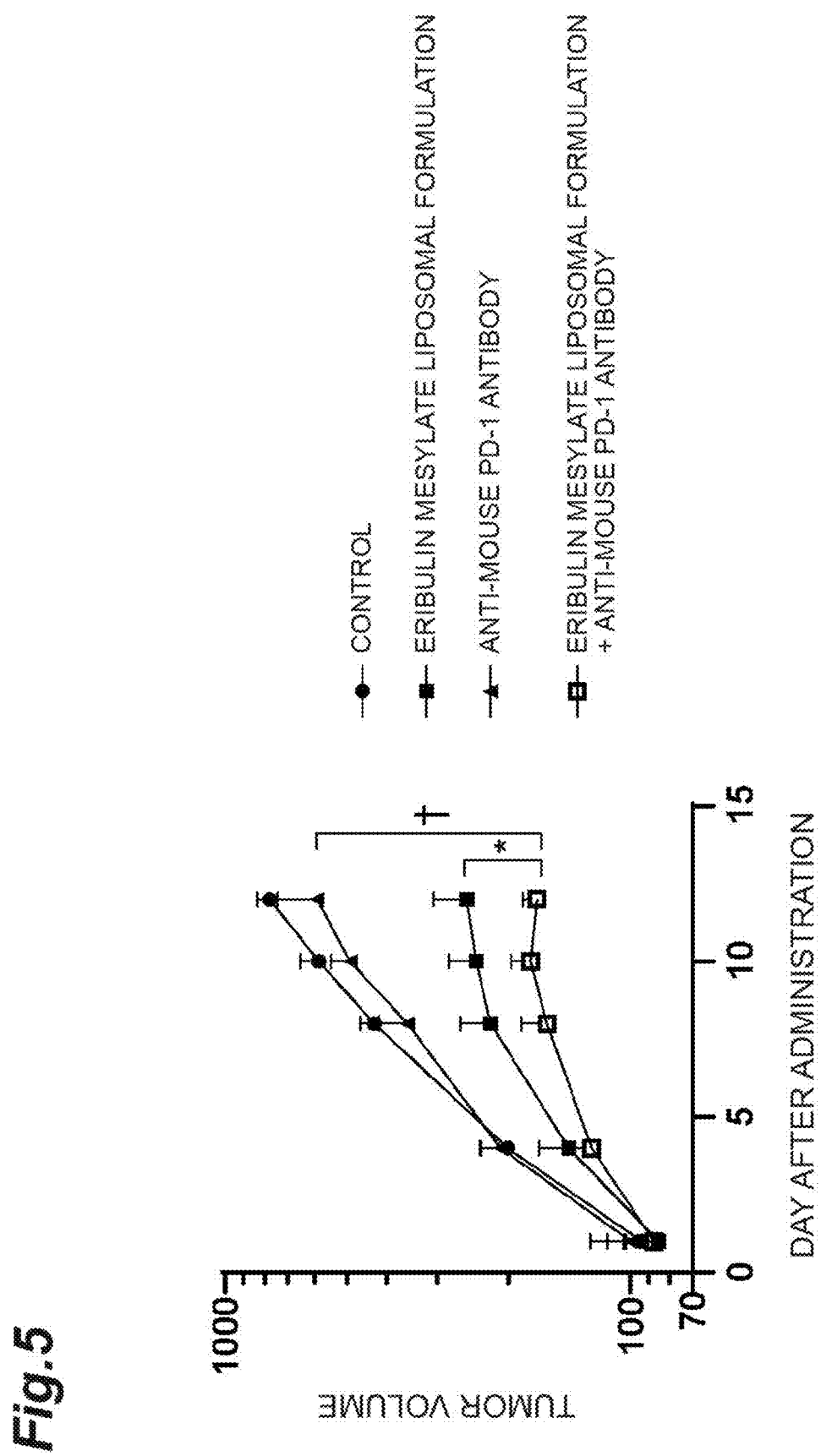
FIG. 5 is a graph illustrating effect of treatment with a combination of a liposomal formulation comprising Eribulin mesylate at a dose of 0.3 mg/kg and an anti-PD-1 antibody on tumor growth.

The mean and standard deviation (SD) of the results of measurement of the tumor volume in each group are illustrated in FIG. 5. For statistical analysis, repeated measures analysis of variance followed by Dunnett's multiple comparison was conducted between the combined administration group of Eribulin mesylate liposomal formulation and anti-human PD-1 antibody and each alone administration group (*, t: $p<0.05$).

As a result, in tumor-bearing mice with human gastric cancer MKN45 tumor having human immunity, the combined administration of Eribulin mesylate liposomal formulation at low dose (0.3 mg/kg) and anti-human PD-1 antibody exhibited excellent antitumor effect in comparison with the Eribulin mesylate liposomal formulation alone administration group or anti-human PD-1 antibody alone administration group. In FIG. 5, (*) indicates that the combined administration of Eribulin mesylate liposomal formulation and anti-human PD-1 antibody statistically significantly inhibited tumor growth in comparison with the Eribulin mesylate liposomal formulation alone administration and (t) indicates that the combined administration of Eribulin mesylate liposomal formulation and anti-human PD-1 antibody statistically significantly inhibited tumor growth in comparison with the anti-human PD-1 antibody alone administration.

Figure 6:
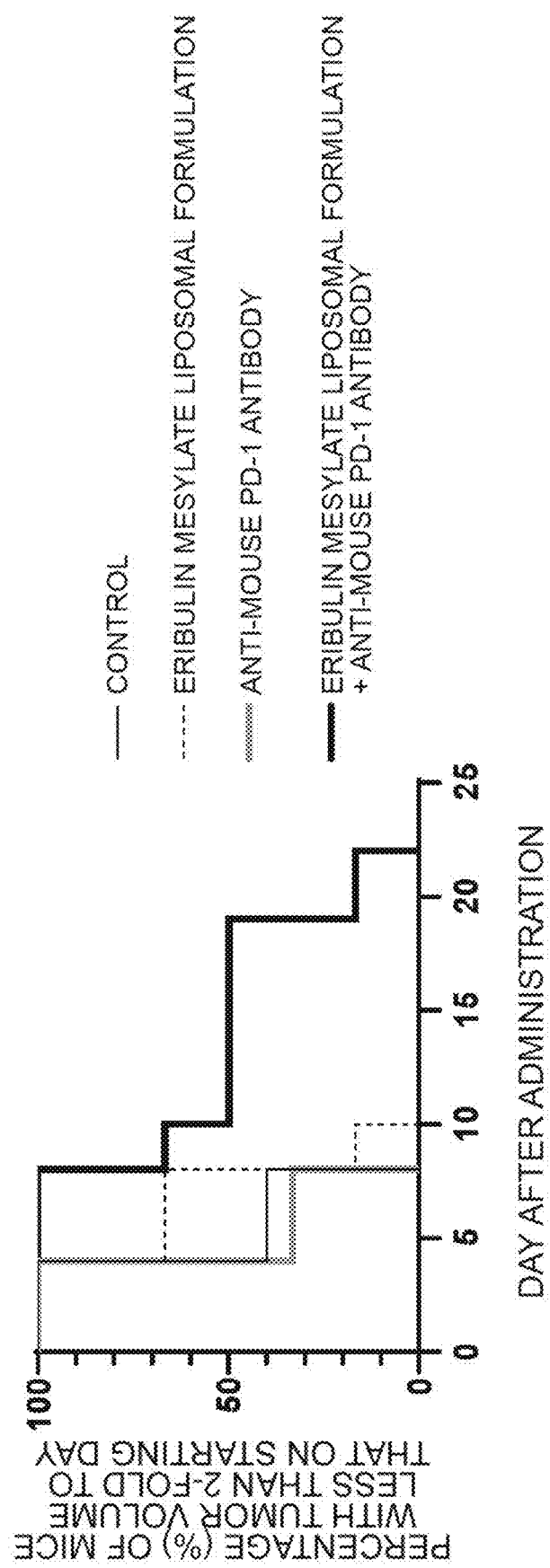
FIG. 6 is a graph illustrating effect of treatment with a combination of a liposomal formulation comprising Eribulin mesylate at a dose of 0.3 mg/kg and an anti-PD-1 antibody on Tx2.

The result of comparison of the groups for the time until the tumor volume exceeds twice that on the starting date of administration (Tx2) in the experiment is shown in FIG. 6 and the median of Tx2 in each group and the percentage (%) thereof to the control group are set forth in Table 9. For statistical analysis, the Log-rank test was conducted in comparison with the control group to calculate the Bonferroni-corrected p-value (#: $p<0.05$).

As a result, in tumor-bearing mice with human gastric cancer MKN45 tumor having human immunity, the combined administration of Eribulin mesylate liposomal formulation (0.3 mg/kg) and the anti-human PD-1 antibody exhibited the effect of extending suppression time (362.5%) of tumor growth (Tx2). On the other hand, administration of Eribulin mesylate liposomal formulation at a low dose (0.3 mg/kg) alone and administration of anti-human PD-1 antibody alone did not show a significant effect of extending suppression time. # in Table 9 indicates that the combined administration group of Eribulin mesylate liposomal formulation and anti-human PD-1 antibody statistically significantly extended suppression time of tumor growth in comparison with the control group.

TABLE 9

Effect of combined administration of Eribulin mesylate liposomal formulation (0.3 mg/kg) and anti-human PD-1 antibody to Tx2

| Group | Tx2 (days) | Ratio to control |
|---|---|---|
| Control | 4.0 | 100% |
| Eribulin mesylate liposomal formulation alone | 8.0 | 200% |
| Anti-human PD-1 antibody alone | 4.0 | 100% |
| Eribulin mesylate liposomal formulation + anti-human PD-1 antibody combined administration | 14.5 # | 362.5% |

Example 7

Antitumor effect of combined administration of Eribulin mesylate at low dose (0.3 mg/kg) or Eribulin mesylate liposomal formulation at low dose (0.3 mg/kg) and anti-human PD-1 antibody in tumor-bearing mice of human gastric cancer MKN45 cell line having human immunity Preparation of Human Peripheral Blood Mononuclear Cells Human peripheral blood mononuclear cells are isolated from blood collected from healthy volunteers. An equal amount of Cellotion (ZENOGEN PHARMA CO., LTD.) is added to the blood and mixed, and a human peripheral blood mononuclear cell layer is isolated using a Leucosep lymphocyte separation tube (Greiner Bio-One). The isolated human peripheral blood mononuclear cells are suspended in CELLBANKER 2 (ZENOGEN PHARMA CO., LTD.) and stored at −80° C. until use.

Preparation of human gastric cancer MKN45 tumor-bearing mice Human gastric cancer MKN45 cells (purchased from JCRB cell bank) are cultured in RPMI1640 medium (FUJIFILM Wako Pure Chemical Corporation) containing 10% FBS (fetal bovine serum) and antibiotics under conditions at 37° C. in a 5% carbon dioxide gas incubator. The cells are collected using trypsin-EDTA when the cells reach to approximately 80% confluency. Hank's balanced salt solution (Thermo Fisher Scientific) is added to the collected cells to prepare a suspension at $4.0 \times 10^7$ cells/mL, and 0.1 mL of the suspension is subcutaneously transplanted to the right body side into 8 mice (NOD/Shi-scid, IL-2RγKO Jic, In-Vivo Science Inc.) per each group, i.e. in the control group, the Eribulin mesylate alone administration group, the Eribulin mesylate liposomal formulation alone administration group, the anti-human PD-1 antibody (MSD) alone administration group, the combined administration group of Eribulin mesylate and anti-human PD-1 antibody and the combined administration group of Eribulin mesylate liposomal formulation and anti-human PD-1 antibody.

Preparation of Human Gastric Cancer MKN45 Tumor-Bearing Mice Having Human Immunity The isolated human peripheral blood mononuclear cells are transplanted into the human gastric cancer MKN45 tumor-bearing mice prepared by the above method to prepare human gastric cancer MKN45 tumor-bearing mice having human immunity. Human peripheral blood mononuclear cells stored at −80° C. are thawed, the cells are separated by centrifugation (500×g, 10 minutes), and Hank's balanced salt solution (Thermo Fisher Scientific) is added to prepare a suspension at $2.0 \times 10^7$ cells/mL. Mice on day 3 after transplantation of human gastric cancer MKN45 cell line are transplanted with 0.2 mL ($4.0 \times 10^6$ cells/mouse) of the human peripheral blood mononuclear cell suspension prepared by the above method by tail vein injection.

Anti-Tumor Effect

Using human gastric cancer MKN45 tumor-bearing mice having human immunity prepared by the above method, the antitumor effects of the combined administration of Eribulin mesylate at low dose (0.3 mg/kg) and an anti-human PD-1 antibody, and the combined administration of Eribulin mesylate liposomal formulation at low dose (0.3 mg/kg) and an anti-human PD-1 antibody are evaluated. From day 4 after human peripheral blood mononuclear cell transplantation (day 7 after human gastric cancer MKN45 cell line transplantation), the Eribulin mesylate (0.3 mg/kg, once a week, twice in total, tail vein injection), the Eribulin mesylate liposomal formulation (0.3 mg/kg, once a week, twice in total, tail vein injection) and the anti-human PD-1 antibody (10 mg/kg, twice a week, four times in total, intraperitoneal injection) are administered, alone or in combination, to the alone administration groups or the combination administration group, respectively. No drug is administered to the control group.

The longest diameter and the short axis of the tumor grown in each mouse are measured with a digimatic caliper (a product made by Mitutoyo Corporation) twice or thrice a week for three weeks with the starting date of administration being day 1.

The tumor volume is calculated in accordance with the following formula.

$$\text{Tumor volume (mm}^3\text{)} = \text{longest diameter (mm)} \times \text{short axis (mm}^2\text{)}/2$$

The mean and standard deviation (SD) of the results of measurement of the tumor volume in each group are calculated. For statistical analysis, repeated measures analysis of variance followed by Dunnett's multiple comparison is conducted between the combined administration group of Eribulin mesylate and anti-human PD-1 antibody and each alone administration group. The statistical comparison between two groups of the combined administration group of Eribulin mesylate and anti-human PD-1 antibody and the combined administration group of Eribulin mesylate liposomal formulation and anti-human PD-1 antibody is conducted by repeated measures analysis of variance.

Comparison of the groups for the time until the tumor volume exceeds twice that on the starting date of administration (Tx2) in the experiment is conducted. For statistical analysis, the Log-rank test is conducted in comparison with the control group to calculate the Bonferroni-corrected p-value. The Log-rank test between two groups of the combined administration group of Eribulin mesylate liposomal formulation and anti-human PD-1 antibody to the combined administration group of Eribulin mesylate and anti-human PD-1 antibody is conducted.

The invention claimed is:

1. A method for treating tumor, comprising administering
   (i) a liposomal composition comprising Eribulin or a pharmaceutically acceptable salt thereof, and
   (ii) a PD-1 antagonist comprising an anti-PD-1 antibody and/or an anti-PD-L1 antibody to a patient in need thereof,
   wherein the tumor is gastric cancer, esophageal cancer, lung cancer, thymic carcinoma or biliary tract cancer.

2. The method of claim 1, wherein the tumor is small cell lung cancer.

3. The method of claim 1, wherein the tumor is the biliary tract cancer that is intrahepatic cholangiocarcinoma.

4. The method of claim 1, wherein the liposomal composition comprising Eribulin or the pharmaceutically acceptable salt thereof and the PD-1 antagonist are administered simultaneously, separately, continuously, or at a time interval.

5. The method of claim 1, wherein Eribulin or the pharmaceutically acceptable salt thereof is Eribulin mesylate.

6. The method of claim 1, wherein the PD-1 antagonist is an anti-PD-1 antibody.

7. The method of claim 6, wherein the anti-PD-1 antibody is selected from the group consisting of Nivolumab, Pembrolizumab, Cemiplimab, Sintilimab and Toripalimab.

8. The method of claim 6, wherein the anti-PD-1 antibody is Nivolumab and wherein Nivolumab is administered at 3 mg/kg (body weight) every 2 weeks, at 240 mg every 2 weeks, at 360 mg every 3 weeks or at 480 mg every 4 weeks.

9. The method of claim 6, wherein Eribulin or the pharmaceutically acceptable salt thereof is Eribulin mesylate and the anti-PD-1 antibody is Nivolumab, wherein Eribulin mesylate is intravenously administered at 1.7 to 2.1 mg/m$^2$ (body surface area) and Nivolumab is intravenously administered at 360 mg on day 1 of a 21-day cycle.

10. The method of claim 6, wherein Eribulin or the pharmaceutically acceptable salt thereof is Eribulin mesylate and the anti-PD-1 antibody is Nivolumab, wherein Eribulin mesylate is intravenously administered at 1.1 to 1.4 mg/m$^2$ (body surface area) and Nivolumab is intravenously administered at 240 mg on days 1 and 15 of a 28-day cycle.

11. The method of claim 1, wherein the tumor excludes non-small cell lung cancer.

12. The method of claim 1, wherein the tumor is the gastric cancer.

13. The method of claim 1, wherein the tumor is the esophageal cancer.

14. The method of claim 1, wherein the tumor is the lung cancer.

15. The method of claim 1, wherein the tumor is non-small cell lung cancer.

16. The method of claim 1, wherein the tumor is the thymic carcinoma.

17. The method of claim 1, wherein the tumor is the biliary tract cancer.

18. The method of claim 1, wherein the PD-1 antagonist is an anti-PD-L1 antibody.

* * * * *